United States Patent
Liu et al.

(10) Patent No.: US 9,951,149 B2
(45) Date of Patent: Apr. 24, 2018

(54) REVERSIBLE HEPARIN MOLECULES AND METHODS OF MAKING AND USING THE SAME

(71) Applicants: The University of North Carolina at Chapel Hill, Chapel Hill, NC (US); Rensselaer Polytechnic Institute, Troy, NY (US); NUTECH VENTURES, Lincoln, NE (US)

(72) Inventors: Jian Liu, Chapel Hill, NC (US); Yongmei Xu, Durham, NC (US); Robert J. Linhardt, Albany, NY (US); Edward Harris, Lincoln, NE (US)

(73) Assignees: The University of North Carolina at Chapel Hill, Chapel Hill, NC (US); Rensselaer Polyechnic Institute, Troy, NY (US); NUtech Ventures, Lincoln, NE (US)

( * ) Notice: Subject to any disclaimer, the term of this patent is extended or adjusted under 35 U.S.C. 154(b) by 0 days.

(21) Appl. No.: 14/898,865

(22) PCT Filed: Jun. 17, 2014

(86) PCT No.: PCT/US2014/042683
§ 371 (c)(1),
(2) Date: Dec. 16, 2015

(87) PCT Pub. No.: WO2014/204929
PCT Pub. Date: Dec. 24, 2014

(65) Prior Publication Data
US 2016/0122446 A1    May 5, 2016

Related U.S. Application Data

(60) Provisional application No. 61/835,875, filed on Jun. 17, 2013.

(51) Int. Cl.
| | | |
|---|---|---|
| A61K 31/727 | (2006.01) | |
| C08B 37/00 | (2006.01) | |
| C12P 19/18 | (2006.01) | |
| C12P 19/04 | (2006.01) | |
| C12P 19/26 | (2006.01) | |
| C08L 5/10 | (2006.01) | |

(52) U.S. Cl.
CPC ........ C08B 37/0075 (2013.01); A61K 31/727 (2013.01); C08B 37/0003 (2013.01); C08L 5/10 (2013.01); C12P 19/04 (2013.01); C12P 19/18 (2013.01); C12P 19/26 (2013.01)

(58) Field of Classification Search
CPC .............. A61K 31/727; C08B 37/0003; C08B 37/0075; C08L 5/10; C12P 19/04; C12P 19/18; C12P 19/26; A01M 7/00
See application file for complete search history.

(56) References Cited

U.S. PATENT DOCUMENTS

| | | |
|---|---|---|
| 4,554,101 A | 11/1985 | Hopp |
| 4,865,870 A | 9/1989 | Hu et al. |
| 5,543,403 A | 8/1996 | Petitou et al. |
| 5,817,487 A | 10/1998 | Kobayashi et al. |
| 5,834,282 A | 11/1998 | Habuchi et al. |
| 5,935,824 A | 8/1999 | Sgarlato |
| 6,255,088 B1 | 7/2001 | Wong et al. |
| 6,861,254 B1 | 3/2005 | Rosenberg et al. |
| 7,531,338 B2 | 5/2009 | Liu |
| 2003/0083294 A1 | 5/2003 | Sullenger et al. |
| 2003/0099967 A1 | 5/2003 | Deangelis |
| 2004/0191870 A1 | 9/2004 | Rosenberg et al. |
| 2005/0101532 A1 | 5/2005 | Yang et al. |
| 2005/0255562 A1 | 11/2005 | Rosenberg et al. |
| 2006/0165673 A1 | 7/2006 | Liu |
| 2006/0172931 A1 | 8/2006 | San Antonio et al. |
| 2008/0109236 A1 | 5/2008 | DeAngelis |
| 2009/0035787 A1 | 2/2009 | Liu |
| 2009/0197308 A1 | 8/2009 | Liu |
| 2010/0125052 A1 | 5/2010 | Lu et al. |
| 2010/0305022 A1 | 12/2010 | Shriver |
| 2011/0054236 A1 | 3/2011 | Yang et al. |
| 2012/0308546 A1 | 12/2012 | Kizhakkedathu et al. |
| 2012/0322114 A1 | 12/2012 | Liu et al. |
| 2012/0322760 A1 | 12/2012 | Fier et al. |
| 2013/0022647 A1 | 1/2013 | Kizhakkedathu et al. |
| 2013/0296540 A1* | 11/2013 | Xu ....................... C12N 9/1051 536/21 |

FOREIGN PATENT DOCUMENTS

| | | |
|---|---|---|
| EP | 0 394 971 | 10/1990 |
| EP | 0 565 863 | 10/1993 |
| WO | WO 96/14425 | 5/1996 |
| WO | WO2003018598 | 3/2003 |
| WO | WO 2004/005475 | 1/2004 |
| WO | WO 2004/009642 | 1/2004 |
| WO | WO 2004-017910 | 3/2004 |
| WO | WO 2004/017910 A2 * | 3/2004 |
| WO | WO 2006/124801 | 11/2006 |
| WO | WO2012088416 | 6/2012 |
| WO | WO 2012/088416 A2 * | 8/2012 |
| WO | WO 2012/116048 | 8/2012 |
| WO | WO2014/204929 | 12/2014 |

OTHER PUBLICATIONS

Schroeder et al. Anal. Bioanal. Chem. (2011) 399: 763-771.*
(Continued)

*Primary Examiner* — Susan M Hanley
(74) *Attorney, Agent, or Firm* — Jenkins, Wilson, Taylor & Hunt, P.A.

(57) ABSTRACT

Methods and systems for synthesizing heparin compounds are provided. The chemoenzymatic synthesis of structurally homogeneous low molecular weight heparins that have a reversible anticoagulant activity is provided. Also disclosed are heparin compounds having anticoagulant activity, including a binding affinity to antithrombin and an anti-Xa activity, but no detectable anti-IIa activity. Additionally, provided are synthetic, low-molecular weight heparin compounds with reversible anticoagulant activity, where the anticoagulant activity is reversible by protamine.

21 Claims, 8 Drawing Sheets

(56) References Cited

OTHER PUBLICATIONS

Pempe et al. J. Biol. Chem. (Jun. 15, 2012) 287(25): 20774-20783.*
British J. Haemotology (2002) 116: 178-186.*
Crowther et al. British J. Haemotology (2002) 116: 178-186.*
Chen, M. PhD dissertation, University of North Carolina, Chapel Hill NC; deposited Oct. 11, 2010.*
Devenport, A. Nephrology (2009) 14: 455-461.*
Aikawa et al., "Molecular Cloning and Expression of a Third Member of the Heparan Sulfate/Heparin GlcNAc N-Deacetylase/N-Sulfotransferase Family," The Journal of Biological Chemistry, vol. 274, No. 5, pp. 2690-2695 (Jan. 29, 1999).
Aikawa et al., "Multiple Isozymes of Heparan Sulfate/Heparin GlcNAc N-Deacetylase/GlcN N-Sulfotransferase," The Journal of Biological Chemistry, vol. 276, No. 8, pp. 5876-5882 (Feb. 23, 2001).
Alexander et al., "Syndecan-1 is required for Wnt-1-induced mammary tumorigenesis in mice," Nat. Genet., vol. 25, pp. 329-332 (2000).
Altschul et al., "Basic Local Alignment Search Tool," J. Mol. Bio., vol. 1215, pp. 403-410 (1990).
Balagurunathan et al., J. Biol. Chem., vol. 278, pp. 52613-52621 (2003).
Balagurunathan et al., Nat. Biotechnol., vol. 21, pp. 1343-1346 (2003).
Baleux et al., (2009) Nat. Chem. Biol., 5, 743-748.
Bitter et al., (1962) Anal. Biochem. 4, 330-334.
Bowman et al., Carbohydrate sulfotransferases: medliators of extracellular Communication, Chemistry & Biology, vol. 6, pp. R9-R22 (Jan. 1999).
Broun et al., "Catalytic plasticity of fatty acid modification enzymes underlying chemical diversity of plant lipids," Science, vol. 282, pp. 1315-1317 (1998).
Brown et al., Drug Research, "Cardenolide analogues. 11. Improved method for the use of Fetizon's reagent in the synthesis of cardiac glycosides", 1981, vol. 31, No. 7, pp. 1059-1064.
Burkart et al., "Regeneration of PAPS for the Enzymatic Synthesis of Sulfated Oligosaccharides," J. Org. Chem., vol. 65, pp. 5565-5574 (2000).
Cai et al., "Towards the chemoenzymatic synthesis of heparan sulfate oligosaccharides: Oxidative cleavage of p-nitrophenyl group with ceric ammonium salts," Tetra. Lett., vol. 54, No. 33, pp. 4471-1471 (2013).
Carfi et al., "Herpes Simplex Virus Glycoprotein D Bound to the Human Receptor HveA," Molecular Cell, vol. 8, pp. 169-179 (Jul. 2001).
Casu et al. Carbohydrate Research 263 (1994) 271-28.
Chen et al., "Enzymatic redesigning of biologically active haparan sulfate," JBC, vol. 280, No. 52, pp. 42817-42825 (2005).
Chen, M., et al. (2006) Biochemistry, 45, 12358-12365.
Chen et al., "Using an Enzymatic Combinatorial Approach to Identify Anticoagulant Heparan Sulfate Structures," Chemistry and Biology, Current Biology, London, GB, vol. 14, No. 9, pp. 986-993 (Sep. 19, 2007).
Chen, Maio, Towards De Novo Synthesis of Structure-Defined Oligosaccharides with Heparan Sulfate Biosynthetic Enzymes, PhD dissertation, Date Created: Aug. 2008; Date Desposited: Oct. 11, 2010.
Copeland et al., "Using a 3-O-Sulfated Heparin Octasaccharide to Inhibit the Entry of Herpes Simplex Virus Type 1," Biochemistry, vol. 47, pp. 5774-5783 (2008).
Dooley, T., "Cloning of the human phenol sulfotransferase gene family: three genes implicated in the metabolism of catecholamines, thyroid hormones and drugs," Chemico-Biological Interactions, vol. 109, pp. 29-41 (1998).
Duncan et al., Biochim. Biophys. Acta, vol. 1671, pp. 34-43 (2004).
Edens, R.E., et al., (1992) J. Pharm. Sci., 81, 823-827.
Esko et al., "Molecular diversity of heparan sulfate," J. Clin. Invest., vol. 108, pp. 169-173 (2001).
Esko et al., Annu. Rev. Biochem., vol. 71, pp. 435-471 (2002).

Falany, C., "Introduction: Changing view of sulfation and the cytosolic Sulfotransferases," vol. 11, The FASEB Journal, pp. 1-2 (Jan. 1997).
Feyerabend et al., (2006) Nat. Chem. Biol. 2, 195-196.
Fukuta et al., "Molecular cloning and expression of human chondroitin 6-sulfotransferase," Biochimica et Biophysica Acta, vol. 1399, pp. 57-61 (1998).
Guerrini et al., (2008) Nat. Biotechnol., 26, 669-675.
Habuchi et al., J. Biol. Chem., vol. 275, pp. 2859-2868 (2000).
Habuchi et al., "Molecular Characterization and Expression of Heparan-sulfate 6-Sulfotransferase—Complete cDNA Cloning in Human and Partial Cloning in Chinese Hamster Ovary Cells," The Journal of Biological Chemistry, vol. 273, No. 15, pp. 9208-9213 (Apr. 10, 1998).
Hirsch et al. (2004) CHEST, vol. 126, pp. 188S-203S.
Hirsch et al. (2007) Circulation, 116, 552-560.
International Preliminary Report on Patentability corresponding to International Application No. PCT/US2014/042683 dated Dec. 30, 2015.
International Preliminary Report on Patentability corresponding to International Application No. PCT/US2011/066843 dated Jul. 4, 2013.
International Search Report corresponding to International Application No. PCT/US2014/042683 dated Oct. 9, 2014.
Jemth et al., "Oligosaccharide library-based assessment of heparan sulfate 6-0-sulfotransferase substrate specificity," Journal of Biological Chemistry, vol. 278, No. 27, pp. 24371-24376 (Jul. 4, 2003).
Kakkar et al. (2004) J. Clin. Oncol., vol. 22, pp. 1944-1948.
Kisselev, L., "Polypeptide release factors in prokaryotes and eukaryotes: same function, different structure," Structure, vol. 10, pp. 8-9 (2002).
Laurent et al. (1978) Biochem. J., vol. 175, pp. 691-701.
Lee, M.K., and Lander, A.D., (1991) Proc. Natl. Acad. Sci. USA 88, 2768-2772.
Lindahl et al., "Regulated Diversity of Heparan Sulfate," The Journal of Biological Chemistry, vol. 273, No. 39, pp. 24979-24982 (Sep. 25, 1998).
Lindahl et al., J. Med. Chem., vol. 48, pp. 349-352 (2005).
Linhardt et al. (1999) Seminars in Thrombosis and Hemostasis, vol. 25, Suppl.3, pp. 5-16.
Linhardt, R. J., J. Med. Chem., vol. 46, pp. 2551-2564 (2003).
Liu et al., "Cell SurfaceHeparan Sulfate and its Roles in AssistingViral Infections," Medicinal Research Reviews, vol. 22, No. 1, pp. 1-25 (2002).
Liu et al., "Characterization of a Heparan Sulfate Octasaccharide that Binds to Herpes Simplex Virus Type 1 Glycoprotein D," The Journal of Biological Chemistry, vol. 277, No. 36, pp. 33456-33467 (Sep. 6, 2002).
Liu et al., "Expression of Heparan Sulfate D-Glucosaminyl 3-O-Sulfotransferase Isoforms Reveals Novel Substrate Specificities," The Journal of Biological Chemistry, vol. 274, No. 8, pp. 5185-5192 (Feb. 19, 1999).
Liu et al., "Heparan Sulfate D-Glucosaminyl 3-O-Sulfotransferase-3A Sulfates N-Unsubstituted Glucosamine Residues," The Journal of Biological Chemistry vol. 274, No. 53, pp. 38155-38162 (Dec. 31, 1999).
Liu et al., "Purification of Heparan Sulfate D-Glucosaminyl 3-O-Sulfotransferase," The Journal of Biological Chemistry, vol. 271, No. 43, pp. 27072-27082 (Oct. 25, 1996).
Liu et al. (2009) Nat. Prod. Rep., 26, 313-321.
Liu et al., "Anticoagulant heparan sulfate: structural specificity and biosynthesis," Appl Microbiol Biotechnol., vol. 74, pp. 263-272 (2007).
Liu, R. et al. J Biol Chem 285, 34240-34249 (2010).
Loganathan et al. (1990) Biochemistry, 29, 4362-4368.
Maccarana et al., J. Biol. Chem., vol. 268, pp. 23898-23905 (1993).
Martinez-Gonzalez and Rodriguez (2010) Expert Rev. Cardiovasc. Ther., 8, 625-634.
Mazany et al., "Human chondroitin 6-sulfotransferase: cloning, gene structure, and chromosomal localization," Biochimica et Biophysica Acta, vol. 1407, pp. 92-97 (1998).
Mousa (2010) Meth. Mol. Biol., 663, 1-28.
Mousa (2010), Meth. Mol. Biol., 663, 29-107.

(56) References Cited

OTHER PUBLICATIONS

Mousa S.A. in Drug Discovery and Evaluation: Pharmacological Assays (ed. Vogel, H.), 393-456 (Springer-Verlag Berlin, Heidelberg, New York, 2008).
Munoz et al., "Enzymatic synthesis of heparin related polysaccharides on sensor chips: Rapid screening heparin-protein interactions," Biochemical and Biophysical Research Communications, Academic Press Inc., Orlando, FL, US, vol. 339, No. 2, pp. 597-602 (Jan. 13, 2006).
Nastuk et al., "Expression Cloning and Characterization of NSIST, a Novel Sulfotransferase Expressed by a Subset of Neurons and Postsynaptic Targets," The Journal of Neuroscience, vol. 18, No. 18, pp. 7167-7177 (Sep. 15, 1998).
Noti and Seeberger, (2005) Chemistry & Biology, 12, 731-756.
Notification Concerning of Transmittal of International Preliminary Report on Patentability for International Application No. PCT/US2006/018778 (dated Nov. 22, 2007).
Notification of Transmittal of the International Search Report and the Written Opinion of the International Searching Authority, or the Declaration for International Application No. PCT/US06/18778 (Feb. 21, 2007).
Notification of Transmittal of the International Search Report and the Written Opinion of the International Searching Authority, or the Declaration corresponding to International Application No. PCT/US2008/008945 dated Feb. 20, 2009.
Notification of Transmittal of the International Search Report and the Written Opinion of the International Searching Authority, or the Declaration corresponding to International Application No. PCT/US2011/066843 dated Aug. 22, 2012.
Office Action corresponding to U.S. Appl. No. 13/996,930, filed Oct. 8, 2015.
Office Action corresponding to U.S. Appl. No. 12/178,434, filed Oct. 28, 2011.
Office Action corresponding to U.S. Appl. No. 12/178,434, filed Apr. 19, 2011.
Office Action corresponding to U.S. Appl. No. 12/178,434, filed Jan. 26, 2011.
Official Action corresponding to U.S. Appl. No. 11/920,319, filed Apr. 28, 2010.
Ong et al., "Expression Cloning of a Human Sulfotransferase that Directs the Synthesis of the HNK-1 Glycan on the Neural Cell Adhesion Molecule and Glycolipids," The Journal of Biological Chemistry, vol. 273, No. 9, pp. 5190-5195 (Feb. 27, 1998).
Ouyang et al., "Molecular Cloning and Expression of Human and Mouse Tyrosylprotein Sulfotransferase-2 and a Tyrosylprotein Sulfotransferase Homologue in Caenorhabditis elegans," The Journal of Biological Chemistry, vol. 273, No. 38, pp. 24770-24774 (Sep. 18, 1998).
Petitou et al., Angew. Chem. Int. Ed., vol. 43, pp. 3118-3133 (2004).
Razi et al., Biochem. J. (1995) 389, 465-472.
Rosenberg et al., "Heparan Sulfate Proteogylcans of the Cardiovascular System Specific Structures Emerge But How Is Synthisis Regulated?" J. Clin. Invest., vol. 99, No. 9, pp. 2062-2070 (May 1997).
Saeki et al., "Molecular Cloning, Expression, and Characterization of a Novel Mouse Liver SULT1B1 Sulfotransferase," J. Biochem., vol. 124, pp. 55-64 (1998).
Sala, R. F. et al., Carbohydrate Research, "UDP-N-trifluoroacetylglucosamine as an alternative substrate in Nacetylglucosaminyltransferase reactions", 1998, vol. 306, pp. 127-136.
Saribas et al., "Production of N-sulfated 1-38 polysaccharides using yeast-expressed N-deacetylase/N-sulfotransferase-1 (NDST-I)," Glycobiology, vol. 14, pp. 1217-1228 (2004).
Shworak et al., "Molecular Cloning and Expression of Mouse and Human cDNAs Encoding Heparan Sulfate D-Glucosaminyl 3-O-Sulfotransferase," The Journal of Biological Chemistry, vol. 272, No. 44, pp. 28008-28019, (Oct. 31, 1997).
Shriver et al., (2004) Nat. Rev. Drug Discov. 863-873.

Shukla et al., "A Novel Role for 3-O-Sulfated Heparan Sulfate in Herpes Simplex Virus 1 Entry," Cell, vol. 99, pp. 13-22 (Oct. 1, 1999).
Shukla et al., "Herpes viruses and heparan sulfate: an intimate relationship in aid of viral entry," The Journal of Clinical Investigation, vol. 108, No. 4, pp. 503-510 (Aug. 2001).
Sismey-Ragatz, et al. (2007) J. Biol. Chem., 282, 28321-28327.
Tohu et al. (2004) Clin. Appl. Thrombos Hemostas, 10, 301-309.
Uchimura et al., "Molecular Cloning and Characterization of an N-Acetylglucosamine-6-O-sulfotransferase," The Journal of Biological Chemistry, vol. 273, No. 35, pp. 22577-22583 (Aug. 28, 1998).
Wang et al. (2010) Biotechnol. Bioeng 107, 968-977.
Weitz (2010) Thromb. Res., 125 (Suppl 2), S30-S35.
Weitz and Linkins, (2007) Exert Opin. Investig. Drugs, 16, 271-282.1.
Willis et al., J. Virol., vol. 72, pp. 5938-5947 (1998) . . . Not material, cumulative and/or irrelevant—all material references cited in spec were provided by inventor and disclosed.
Wishart et al., "A single mutation converts a novel phosphotyosine binding domain into a dual-specificity phosphatase," J. Biol. Chem., vol. 270, No. 45, pp. 26782-26785 (1995).
Witkowski et al., "Conversion of b-ketoacyl synthase to a Malonyl Decarboxylase by replacement of the active cysteine with glutamine" Biochemistry, vol. 38, pp. 11643-11650 (1999).
WuDunn et al., J. Virol., vol. 63, pp. 52-58 (1989).
Xu, D. et al., Nat Chem Biol 4, 200-202 (2008).
Xu, Y. et al. Science 334, 498-501 (2011).
Yoshinari et al., "Molecular Cloning, Expression, and Enzymatic Characterization of Rabbit Hydroxysteroid Suffotransferase AST-RB2 (ST2A8)," J. Biochem., vol. 123, pp. 740-746 (1998).
Zhang, L., et al., (2001) J. Biol. Chem. 276, 42311-42321.
Zhang et al. (2008) J. Am. Chem. Soc., 130, 12998-13007.
Zhou et al. "Expression of heparin sulfate sulfotransferases in Kluyveromyces lactis and preparation of 3'-phsphoadenosie-5'-phosphosulfate" (2011) Glycobiology, 21(6),771-780.
Advisory Action corresponding to U.S. Appl. No. 13/996,930, filed Dec. 9, 2016.
Communication of the extended European search report corresponding to European Application No. 14812890.3 dated Dec. 21, 2016.
Communication of European publication number and information on the application of Article 67(3) EPC corresponding to European Application No. 14812890.3 dated Mar. 31, 2016.
Applicant-Initiated Interview Summary corresponding to U.S. Appl. No. 13/996,930 dated Jan. 23, 2017.
Office Action corresponding to U.S. Appl. No. 13/996,930, filed May 26, 2016.
Atha et al., "Contribution of Monossaccharide Residues in Heparin Binding to Antithrombin III," Biochemistry, vol. 24, pp. 6723-6729 (1985).
Avci et al., "Synthetic oligosaccharides as heparin-mimetics displaying anticoagulant properties," Curr. Pharm. Des., vol. 9, pp. 2323-2335 (2003).
Bjornsson, Simultaneous Preparation and Quantitation of Proteoglycans by Preciptation with Alcian Blue, Anal. Biochem., vol. 210, pp. 282-291 (1993).
Chen et al., "Biosynthesis of 3-O-sulfated heparan sulfate: unique substrate specificity of heparan sulfate 3-O-sulfotransferase isoform 5," Glycobiology, vol. 13, No. 11, pp. 785-794 (Nov. 2003).
Chen et al., "Tyrosine-Ester Sulfotransferase from Rat Liver: Bacterial Expression and Identificationn," Protein Expression Purif., vol. 3, pp. 421-426 (1992).
Conrad, Heparin-Binding Proteins, J. of Medicinal Chemistry, vol. 42, No. 4, pp. 777-778 (1998).
Das et al., "Synthesis of Conformationally Locked I-Iduronic Acid Derivatives: Direct Evidence for a Critical Role of the Skew-Boat 2S0 Conformer in the Activation of Antithrombin by Heparin," Chem. Eur. J., vol. 7, No. 22, pp. 4821-4834 (2001).
Dou et al., "Role of Deacetylase Activity of N-Deacetylase/N-Sulfotransferase 1 in Forming N-Sulfated Domain in Heparan Sulfate", The Journal of Biological Chemistry, vol. 290, No. 33, pp. 20427-20437 (Aug. 14, 2015).

(56) References Cited

OTHER PUBLICATIONS

Edavettal et al.,, "Crystal Structure and Mutational Analysis of Heparan Sulfate 3-O-Sulfotransferase Isoform 1," J. Biol. Chem., vol. 279, No. 24, pp. 25789-25797 (Jun. 11, 2004).
Fuster et al., The sweeta nd sour of cancer: glycans as novel therapeutic tragets, Nat. Rev. Cancer, vol. 5, No. 7, pp. 1-27 (Jul. 2005).
Gallagher, "Heparan sulfate: growth control with a restricted sequence menu," J. Clin. Invest., vol. 108, pp. 357-361 (2001).
Gama et al., "Sulfation patterns of glycosaminoglycans encode molecular recognition and activity," Nat. Chem. Biol., vol. 2, No. 9, pp. 467-473 (Sep. 2006).
Guimond et al., "Fibroblast growth factor receptor signaling in dictated by specific heparin sulphate saccharides," Curro. Biol., vol. 9, No. 22 pp. 1343-1346 (1999).
Lin et al., "Enzymatic Synthesis and Regeneration of 3'-Phosphoadenosine 5'Phosphosulfate (PAPS) for Regioselective Sulfation of Oligosaccharides," J. Am. Chem. So., vol. 117, pp. 8031-8032 (1995).
Nicola et al., Structure-Function Analysis of Soluble Forms of Herpes Simplex Virus Glycoprotein D, J. Virol., vol. 70, No. 6, pp. 3815-3822 (1996).
Ozawa et al., "Nucleotide sequences of a full-length cDNA (PST-1) for aryl sulfotransferase from rat liver," Nucleic Acidse Res., vol. 18, No. 13, p. 4001 (1990).
Pinhal et al., "Enyme interactions in heparan sulfate biosynthesis: Uronosyl 5-epimerase and 2-O-sulfotransferase interact in vivo.," Proc. Natl. Acad. Sci. U.S.A., vol. 98, No. 23, pp. 12984-12989 (Nov. 6, 2001).
Sundaram, M. et al., "Rational design of low-molecular weight heparins with improved in vivo activity," Proc. Natl. Acad. Sci., vol. 100, No. 2, pp. 651-656 (Jan. 21, 1003).
Xia et al., "Heparan Sulfate 3-O-Sulfotransferase Isoform 5 Generates Both an Antithrombin-binding Site and an Entry Receptor for Herpes Simplex Virus, Type 1," J. Biol. Chem., vol 277, No. 40, pp. 37912-37919 (2002).
Xu et al., "Characterization of heparan sulphate 3-O-sulphotransferase isoform 6 and its role in assisting the entry of herpes simplex virus type 1," Biochem. J., vol. 385, pp. 451-459 (2005),
Yang et al. Effects of 3'-phosphoadenosine 5'-phosphate on the activity and folding of phenol sulfotransferase. Chem.-Biol. Interact. 109: 129-135 (1998).
Yang et al., "Two Phenol Sulfotransferase Species from One cDNA: Nature of the Differences," Protein Expression Purif, vol. 8, pp. 423-429 (1996).
Zhao et al. "Enzymatic route to preparative-scale synthesis of UDP-GlcNAc/GalNAc, their analogues and GDP-fucose," Nat. Protoc., vol. 5, No. 4, pp. 636-646 (2010).
Guimond et al., "Fibroblast growth factor receptor signaling is dictated by specific heparin sulphate saccharides," Curro. Biol., vol. 9, No. 22 pp. 1343-1346 (1999).
Guo et al., "Changes in substrate specificity of the recombinant form of phenol sulfotransferase IV (tyrosine-ester sulfotransferase)," Chem.-Biol. Interact., vol. 92, pp. 25-31 (1994).
Harris et al., Endocytic Function, Glycosaminoglycan Specificity, and Antibody Sensitivity of the Recombinant Human 190-kDa Hyaluronan Receptor for Endocytosis (HARE), J. Biol. Chem., vol. 279, No. 35, pp. 36201-36209 (Aug. 27, 2004).
Hernaiz et al., "Enzymatic Modification of Heparan Sulfate on a Biochip Promotes Its Interaction with Antithrombin III," Biochem. Biophys. Res. Commun., vol. 276, pp. 292-297 (2000).
Holmborn et al., "Heparan Sulfate Synthesized by Mouse Embryonic Stem Cells Deficient in NDST1 and NDST2 Is 6-O-Sulfated but Contains No N-Sulfate Groups," J. Biol. Chem., vol. 279, No. 41, pp. 42355-42358 (2004).
Ibrahimi et al., "Kinetic Model for FGF, FGFR, and Proteoglycan Signal Transduction Complex Assembly," Biochemistr, vol. 43, pp. 4724-4730 (2004).

Kakuta et al, "Heparan sulphate N-sulphotransferase activity: reaction mechanism and substrate recognition," Biochem. Soc. Trans., vol 31 (pt2), pp. 331-334 (2003).
Kreuger et al., Interactions between heparan sulfate and proteins: the concept of specificity, J. Cell Biol., vol. 174, No. 3, pp. 323-327 (Jul. 31, 2006).
Krummenacher et al., "The First Immunoglobulin-Like Domain of HveC Is Sufficient To Bind Herpes Simplex Virus gD with Full Affinity, While the Third Domain Is Involved in Oligomerization of HveC," J. Virol., vol. 73, pp. 8127-8137 (Oct. 1999).
Kuberan et al., "Rapid Two-Step Synthesis of Mitrin from Heparosan: A Replacement for Heparin," J. Am. Chem. Soc., vol. 125, pp. 12424-12425 (2003).
Ledin et al., "Heparan Sulfate Structure in Mice with Genetically Modified Heparan Sulfate Production," J. Biol. Chem., vol. 279, No. 41, pp. 42732-42741 (2004).
Li et al., "Biosynthesis of Heparin/Heparan Sulfate cDNA Cloning and Expression of D-Glucuronyl C5-Epimerase From Bovine Lung," J. Biol. Chem., vol. 272, No. 4, pp. 28158-28163 (Oct. 31, 1997).
Lin et al., "Colorimetric Determination of the Purity of 39-Phospho Adenosine 59-Phosphosulfate and Natural Abundance of 39-Phospho Adenosine 59-Phosphate at Picomole Quantities," Anal. Biochem., vol. 264, pp. 111-117 (1998).
Lin et al., "Enzymatic Synthesis and Regeneration of 3'-Phosphoadenosine 5'Phosphosulfate (PAPS) for Regioselective Sulfation of Oligosaccharides," J. Am. Chem. So., vol. 117, pp. 8031-8032 (1995).
Mackman, "Triggers, targets and treatments for thrombosis," Nature, vol. 451, No. 21, pp. 914-918 (Feb. 21, 2008).
Marshall et al., "Control of Activity through Oxidative Modification at the Conserved Residue Cys66 of Aryl Sulfotransferase IV," J. Biol. Chem., vol. 272, No. 14, pp. 9153-9160 (Apr. 14, 1997).
Marshall et al., "A review of the effects of manipulation of the cysteine residues of rat aryl sulfotransferase IV," Chem. Biol. Interact., vol. 109, pp. 107-116 (1998).
Moon et al., "Structural Analysis of the Sulfotransferase (3-O-Sulfotransferase Isoform 3) Involved in the Biosynthesis of an Entry Receptor for Herpes Simplex Virus 1," J. Biol. Chem., vol. 279, No. 43, pp. 45185-45193 (2004).
Moon et al., "Dissecting the substrate recognition of 3-0-sulfotransferase for the biosynthesis of anticoagulant heparin," Proceedings of the National Academy of Sciences, vol. 109, No. 14, pp. 5265-5270 (2012).
Needleman et al., "A General Method Applicable to the Search for Similarities in the Amino Acid Sequence of Two Proteins," J. Mol. Biol., vol. 48, pp. 443-453 (1970).
Nicola et al., Structure-Function Analysis of Soluble Forms of Herpes Simplex Virus Glycoprotein D., J. Virol., vol. 70, No. 6, pp. 3815-3822 (1996).
Ornitz et al., "Receptor Specificity of the Fibroblast Growth Factor Family," J. Biol. Chem., vol. 271, No. 25, pp. 15292-15297 (1996).
Ozawa et al., "Nucleotide sequence of a full-length cDNA (PST-1) for aryle sulfotransferase from rat liver," Nucleic Acids Res., vol. 18, No. 13, p. 4001 (1990).
Petitou et al., "Synthesis of thrombin-inhibiting heparin mimetics without side effects." Nature, vol. 398 pp. 417-422 (Apr. 1, 1990).
Pinhal et al., "Enzyme interactions in heparan sulfate biosynthesis: Uronosyl 5-epimerase and 2-O-sulfotransferase interact in vivo.," Proc. Natl. Acad. Sci. U.S.A., vol. 98, No. 23, pp. 12984-12989 (Nov. 6, 2001).
Pye et al., "Heparan Sulfate Oligosaccharides Require 6-O-Sulfation for Promotion of Basic Fibroblast Growth Factor Mitogenic Activity," J. Biol. Chem., vol. 273, No. 36, pp. 22936-22942 (Sep. 4, 1998).
Reizes et al., "Transgenic Expression of Syndecan-1 Uncovers a Physiological Control of Feeding Behavior by Syndecan-3," Cell, vol. 106, pp. 105-116 (Jul. 13, 2001).
Sasisekharan et al., "Roles of Heparan-Sulphate Glycosaminoglycans in Cancer," Nat. Rev. Cancer, vol. 2, pp. 521-528 (Jul. 2002).

(56) References Cited

OTHER PUBLICATIONS

Schroeder et al., "Protamine neutralization of low molecular weight heparins and their oligosaccharide components," Anal Bioanal Chem, vol. 399, pp. 763.771 (2011).

Schwartz et al., "Virogenic BrdU and BrdU-sensitive DNA sequences are disproportionately concentrated in the template-active chromatin of rat embryo cells," Nuc Acids Res., vol. 6, No. 2, pp. 745-755 (Feb. 1979).

Sheng et al., "Influenced of Phenylalanines 77 and 138 on the Stereospecifity of Aryl Sulfotransferase IV," Drug Metabol. Dispos., vol. 32, No. 5, pp. 559-565 (2004).

Sheng et al., "The Dominating Role of N-Deacetylase/N-Sulfotransferase 1 in Forming Domain Structures in Heparan Sulfate," The Journal of Biological Chemistry, vol. 286, No. 22, pp. 19768-19776 (Jun. 3, 2011).

Shively et al., "Formation of Anhydrosugars in the Chemical Depolymerization of Heparin," Biochemistry, vol. 15, No. 18, pp. 3932-3942 (1876).

Smeds et al., "Substrate specificities of mouse heparan sulphate glucosaminyl 6-O-sulphotransferases," Biochem. J, vol. 372, pp. 371-380 (2003).

Smith et al., "Comparison of Biosequences," Adv. Appl. Math, vol. 2, pp. 482-489 (1981).

Sundaram, M. et al., "Rational design of low-molecular weight heparins with improved in vivo activity," Proc. Natl. Acad. Sci., vol. 100, No. 2, pp. 651-656 (Jan. 21, 2003).

Thompson et al., "Clustal W: improving the sensitivity of progressive multiple sequence alignment through sequence weighting, position-specific gap penalties and weight matrix choice," Nucleic Acids Res., vol. 22, No. 22, pp. 4673-4680 (1994).

Vann et al., "The Structure of the Capsular Polysaccharide (K5 Antigen) of Urinary-Tract-Infective Escherichia coli 010 : K5 : H4 A Polymer Similar to Desulfo-Heparin," Eur. J. Biochem, vol. 116, pp. 359-364 (1981).

Xia et al., "Heparan Sulfate 3-O-Sulfotransferase Isoform 5 Generates Both an Antithrombin-binding Site and an Entry Receptor for Herpes Simplex Virus, Type 1," J. Biol. Chem., vol. 277, No. 40, pp. 37912-37919 (2002).

Xu et al., "Characterization of heparan sulphate 3-O-sulphotransferase isoform 6 and its role in assisting the entry of herpes simplex virus type 1," Biochem. J., vol. 385, pp. 451-459 (2005).

Xu, et. al., "Homogeneous low-molecular-weight heparins with reversible anticoagulant activity," Nat. Chem. Biol., vol. 10, pp. 248-252 (2014).

Yang et al. Effects of 3'-phosphoadenosine 5'-phosphate on the activity and folding of phenol sulfotransferase. Chem.-Biol. Interact. 109: 129-135 (1998).

Yang et al., "Two Phenol Sulfotransferase Species from One cDNA: Nature of the Differences,"Protein Expression Purif, vol. 8, pp. 423-429 (1996).

Zhang et al., "The Effect of Precursor Structures on the Action of Glucosaminyl 3-O-Sulfotransferase-1 and the Biosynthesis of Anticoagulant Heparan Sulfate," J. Biol. Chem., vol. 276, No. 31, pp. 28806-28813 (2001).

Zhao et al. "Enzymatic route to preparative-scale synthesis of UDP-GlcNAc/GalNAc, their analogues and GDP-fucose, " Nat. Protoc., vol. 5, No. 4, pp. 636-646 (2010).

\* cited by examiner

REVERSIBLE HEPARIN MOLECULES AND METHODS OF MAKING AND USING THE SAME

CROSS REFERENCE TO RELATED APPLICATION

This application claims the benefit of U.S. Provisional Patent Application Ser. No. 61/835,875, filed Jun. 17, 2013, the disclosure of which is incorporated herein by reference in its entirety.

GRANT STATEMENT

This invention was made with government support under Grant No. 1R01HL094463 awarded by the National Institutes of Health. The government has certain rights in the invention.

TECHNICAL FIELD

The subject matter disclosed herein relates generally to synthesis of heparin compounds. More particularly, the subject matter disclosed herein relates to chemoenzymatic synthesis of structurally homogeneous low molecular weight heparins that have a reversible anticoagulant activity.

BACKGROUND

Heparan sulfate (HS) is a ubiquitous component of the cell surface and extracellular matrix. It regulates a wide range of physiologic and pathophysiologic functions, including embryonic development and blood coagulation, and can facilitate viral infection (Esko and Selleck (2002) *Annu. Rev. Biochem.* 71, 435-471; Liu and Thorp (2002) *Med. Res. Rev.* 22, 1-25). HS exerts its biological effects by interacting with the specific proteins involved in a given process (Capila and Lindhardt (2002) *Angew. Chem. Int Ed.* 41, 390-412). HS is a highly charged polysaccharide comprising 1→4-linked glucosamine and glucuronic/iduronic acid units that contain both N- and O-sulfo groups. Unique saccharide sequences within HS can determine the specificity of the binding of HS to its target proteins (Linhardt (2003) *J. Med. Chem.* 46, 2551-2564). Heparin, a specialized form of HS, is a commonly used anticoagulant drug. Thus, new methods for the synthesis of heparin compounds and HS attract considerable interest for those developing anticoagulant and other HS-related drugs having improved pharmacological effects.

Heparin has been successfully used as an anticoagulant drug for over 50 years (Mackman, 2008). It is currently marketed in three forms: unfractionated (UF) heparin ($MW_{avg}$ ~14000 Da); a low molecular weight heparin ($MW_{avg}$ ~6000 Da); and the synthetic ULMW heparin pentasaccharide ARIXTRA® (MW 1508.3 Da). UF heparin is used in surgery and kidney dialysis due to its relatively short half-life and its safety for renal impaired patients (Hirsh et al., 2007). LMW heparins and the ULMW heparin ARIXTRA®, introduced over a decade ago, have played an increasingly important role for preventing venous thrombosis among high risk patients (Tohu et al, 2004; Weitz, 2010) because of their more predictable anticoagulant dose, long half-lives and their reduced risk of osteoporosis (Weitz and Linkins, 2007). Recent research on LMW heparin has resulted in the European approval of Bemiparin sodium (Martinez-Gonzalez and Rodriguez, 2010), a second-generation LMW heparin, and the United States approval of a generic LMW heparin, M-Enoxaparin.

UF heparin is isolated from porcine intestine or bovine lung, and LMW heparins are prepared through the chemical or enzymatic degradation of this animal-sourced UF heparin. A worldwide outbreak of contaminated heparin has raised concerns over the reliability and safety of animal sourced heparins and LMW heparins (Guerrini et al., 2008; Liu et al., 2009). As a result, a cost-effective method for preparing new synthetic heparins is highly desirable (Peterson et al., 2009).

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments methods of synthesizing heparin compounds are provided. Such methods can in some embodiments comprise providing a saccharide substrate, elongating the saccharide substrate to a saccharide of a desired or predetermined length, performing an epimerization reaction, and performing one or more sulfation reactions, whereby a heparin compound is synthesized. In some embodiments, the elongation step can comprise employing a glycosyl transferase. In some embodiments, the glycosyl transferase is selected from the group consisting of N-acetyl glucosaminyl transferase of *E. coli* K5 (KfiA) and/or heparosan synthase-2 (pmHS2) from *Pasteurella multocida*. In some embodiments, the elongation step can comprise employing one or more monosaccharides selected from the group consisting of: glucuronic acid (GlcUA), N-acetylated glucosamine (GlcNAc), and N-trifluoroacetyl glucosamine (GlcNTFA).

In some embodiments, methods of synthesizing heparin compounds can further comprise converting an N-sulfotransferase substrate residue on the hexasaccharide or heptasaccharide to a N-sulfo glucosamine (GlcNS) residue, comprising employing N-sulfotransferase (NST) and 3'-phosphoadenosine 5'-phosphosulfate (PAPS). In some embodiments, methods of synthesizing heparin compounds can further comprise employing a base in one or more converting reactions, wherein the base is optionally a lithium hydroxide or a mixture of triethylamine, $CH_3OH$, and/or $H_2O$.

In some embodiments, the epimerization reaction comprises employing $C_5$-epimerase ($C_5$-epi). In some embodiments, the sulfation reaction comprises employing 2-O-sulfotransferase (2-OST). In some embodiments, the sulfation reaction comprises employing 6-O-sulfotransferase (6-OST), optionally 6-OST-1 and/or 6-OST-3. In some embodiments, the sulfation reaction comprises employing 3-O-sulfotransferase (3-OST), optionally 3-OST-1 and/or 3-OST-5.

In some embodiments, the methods of synthesizing heparin compounds can have a yield of greater than 30%. In some embodiments, provided herein are heparin compounds synthesized by the disclosed methods of synthesis. In some embodiments, the heparin compounds can have a molecular weight ranging from about 1500 daltons (Da) to about 6000 Da. In some embodiments, the heparin compounds can have anticoagulant activity. In some embodiments, the heparin compounds can have a binding affinity to antithrombin ranging from about 5 nM to about 30 nM. In some embodiments, the heparin compounds can have anti-Xa activity ranging from about 10 ngml$^{-1}$ to about 40 ngml$^{-1}$ IC$_{50}$ under conditions described herein. In some embodiments, the heparin compounds can have no detectable anti-IIa activity.

In some embodiments, provided herein are methods of synthesizing a heparin compound, comprising providing a monosaccharide substrate, elongating the monosaccharide substrate to a hexasaccharide using enzymes N-acetyl glucosaminyl transferase and heparosan synthase-2, and substrates glucuronic acid (GlcUA) and N-trifluoroacetyl glucosamine (GlcNTFA), converting N-trifluoroacetyl glucosamine (GlcNTFA) residue(s) on the heptasaccharide to N-sulfo glucosamine (GlcNS) residue(s) using N-sulfotransferase (NST), 3'-phosphoadenosine 5'-phosphosulfate (PAPS), and a base, epimerizing the hexasaccharide using C$_5$-epimerase (C$_5$-epi), sulfating the hexasaccharide using 2-O-sulfotransferase (2-OST) and 3'-phosphoadenosine 5'-phosphosulfate (PAPS), sulfating the hexasaccharide using a 6-O-sulfotransferase (6-OST), optionally 6-O-sulfotransferase 1 and/or 3 (6-OST-1 and/or 6-OST-3), and 3'-phosphoadenosine 5'-phosphosulfate (PAPS), and sulfating the hexasaccharide using a 3-O-sulfotransferase (3-OST), optionally 3-O-sulfotransferase 1 (3-OST-1), and 3'-phosphoadenosine 5'-phosphosulfate (PAPS), wherein a heparin compound is synthesized. In some embodiments, the monosaccharide substrate is 1-O-(paranitrophenyl) glucuronide (GlcA-pnp).

In some embodiments, the heparin compound produced by this method has anticoagulant activity. In some embodiments, the heparin compound has a binding affinity to antithrombin ranging from about 5 nM to about 9 nM. In some embodiments, the heparin compound has anti-Xa activity of about 10 ngml$^{-1}$ IC$_{50}$ to about 20 ngml$^{-1}$ IC$_{50}$, optionally about 14 ngml$^{-1}$ IC$_{50}$, under conditions described herein.

In some embodiments, provided herein are methods of synthesizing a heparin compound, comprising providing a monosaccharide substrate, elongating the monosaccharide substrate to a hexasaccharide using enzymes N-acetyl glucosaminyl transferase and heparosan synthase-2, and substrates glucuronic acid (GlcUA) and N-trifluoroacetyl glucosamine (GlcNTFA), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, epimerizing the hexasaccharide using C$_5$-epimerase (C$_5$-epi), sulfating the hexasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, elongating the hexasaccharide substrate to a heptasaccharide using heparosan synthase-2 and the substrate glucuronic acid (GlcUA), elongating the heptasaccharide substrate to a octasaccharide using N-acetyl glucosaminyl transferase and substrate and N-trifluoroacetyl glucosamine (GlcNTFA), epimerizing the octasaccharide using C$_5$-epimerase (C$_5$-epi), sulfating the octasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, sulfating the octasaccharide using a 6-O-sulfotransferase (6-OST), optionally 6-O-sulfotransferase 1 and/or 3 (6-OST-1 and/or 6-OST-3), and 3'-phosphoadenosine 5'-phosphosulfate (PAPS), and sulfating the octasaccharide using a 3-O-sulfotransferase (3-OST), optionally 3-O-sulfotransferase 1 (3-OST-1), and 3'-phosphoadenosine 5'-phosphosulfate (PAPS), wherein a heparin compound is synthesized.

In some embodiments, the heparin compound produced by this method has anticoagulant activity. In some embodiments, the heparin compound has a binding affinity to antithrombin ranging from about 5 nM to about 11 nM. In some embodiments, the heparin compound has anti-Xa activity of about 12 ngml$^{-1}$ IC$_{50}$ to about 22 ngml$^{-1}$ IC$_{50}$, optionally about 17 ngml$^{-1}$ IC$_{50}$, under conditions described herein.

In some embodiments, provided herein are methods of synthesizing a heparin compound, comprising providing a monosaccharide substrate, elongating the monosaccharide substrate to a hexasaccharide using enzymes N-acetyl glucosaminyl transferase and heparosan synthase-2, and substrates glucuronic acid (GlcUA) and N-trifluoroacetyl glucosamine (GlcNTFA), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, epimerizing the hexasaccharide using C$_5$-epimerase (C$_5$-epi), sulfating the hexasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, elongating the hexasaccharide substrate to a heptasaccharide using heparosan synthase-2 and the substrate glucuronic acid (GlcUA), elongating the heptasaccharide substrate to a octasaccharide using N-acetyl glucosaminyl transferase and substrate and N-trifluoroacetyl glucosamine (GlcNTFA), epimerizing the octasaccharide using C$_5$-epimerase (C$_5$-epi), sulfating the octasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), a base, optionally lithium hydroxide, elongating the octasaccharide substrate to a decasaccharide using heparosan synthase-2 and N-acetyl glucosaminyl transferase, and using the substrates glucuronic acid (GlcUA) and N-trifluoroacetyl glucosamine (GlcNTFA), epimerizing the decasaccharide using C$_5$-epimerase (C$_5$-epi), sulfating the decasaccharide using 2-O-sulfotransferase (2-OST) and 3'-phosphoadenosine 5'-phosphosulfate (PAPS), converting N-trifluoroacetyl glucosamine (GlcNTFA) residue(s) on the decasaccharide to N-sulfo glucosamine (GlcNS) residues using N-sulfotransferase (NST), 3'-phosphoadenosine 5'-phosphosulfate (PAPS), and a base, optionally lithium hydroxide, sulfating the decasaccharide using a 6-O-sulfotransferase (6-OST), optionally 6-O-sulfotransferase 1 and/or 3 (6-OST-1 and/or 6-OST-3), and 3'-phosphoadenosine 5'-phosphosulfate (PAPS), and sulfating the decasaccharide using a 3-O-sulfotransferase (3-OST), optionally 3-O-sulfotransferase 1 (3-OST-1), and 3'-phosphoadenosine 5'-phosphosulfate (PAPS), wherein a heparin compound is synthesized.

In some embodiments, the heparin compound produced by this method has anticoagulant activity. In some embodiments, the heparin compound has a binding affinity to antithrombin ranging from about 4 nM to about 6 nM. In some embodiments, the heparin compound has anti-Xa activity of about 10 ngml$^{-1}$ IC$_{50}$ to about 20 ngml$^{-1}$ IC$_{50}$, optionally about 15 ngml$^{-1}$ IC$_{50}$, under conditions described herein. In some embodiments, the heparin compound is susceptible to Stablin-2 mediated endocytosis, wherein a heparin compound that is endocytosed at a rate of 15% or more is susceptible to Stablin-2 mediated endocytosis.

In some embodiments, provided herein are methods of synthesizing a heparin compound, comprising providing a monosaccharide substrate, elongating the monosaccharide substrate to a hexasaccharide using enzymes N-acetyl glucosaminyl transferase and heparosan synthase-2, and substrates glucuronic acid (GlcUA) and N-trifluoroacetyl glucosamine (GlcNTFA), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, epimerizing the hexasaccharide using C$_5$-epimerase (C$_5$-epi), sulfating the hexasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, elongating the hexasaccharide substrate to a heptasaccharide using heparosan synthase-2 and the substrate glucuronic acid (GlcUA), elongating the heptasaccharide substrate to a octasaccharide using N-acetyl glucosaminyl transferase and substrate and N-trifluoroacetyl glucosamine (GlcNTFA), epimerizing the octasaccharide using C$_5$-epimerase (C$_5$-epi), sulfating the octasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, elongating the octasaccharide substrate to a decasaccharide using heparosan synthase-2 and N-acetyl glucosaminyl transferase, and using the substrates glucuronic acid (GlcUA) and N-trifluoroacetyl glucosamine (GlcNTFA), epimerizing the decasaccharide using C$_5$-epimerase (C$_5$-epi), sulfating the decasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, elongating the decasaccharide substrate to a dodecasaccharide using heparosan synthase-2 and N-acetyl glucosaminyl transferase, and using the substrates glucuronic acid (GlcUA) and N-trifluoroacetyl glucosamine (GlcNTFA), epimerizing the dodecasaccharide using C$_5$-epimerase (C$_5$-epi), sulfating the dodecasaccharide using 2-O-sulfotransferase (2-OST) and 3'-phosphoadenosine 5'-phosphosulfate (PAPS), sulfating the dodecasaccharide using a 6-O-sulfotransferase (6-OST), optionally 6-O-sulfotransferase 1 and/or 3 (6-OST-1 and/or 6-OST-3), and 3'-phosphoadenosine 5'-phosphosulfate (PAPS), and sulfating the dodecasaccharide using a 3-O-sulfotransferase (3-OST), optionally 3-O-sulfotransferase 1 (3-OST-1), and 3'-phosphoadenosine 5'-phosphosulfate (PAPS), wherein a heparin compound is synthesized.

In some embodiments, the heparin compound produced by this method has anticoagulant activity. In some embodiments, the heparin compound has a binding affinity to antithrombin ranging from about 23 nM to about 37 nM. In some embodiments, the heparin compound has anti-Xa activity of about 25 ngml$^{-1}$ IC$_{50}$ to about 45 ngml$^{-1}$ IC$_{50}$, optionally about 35 ngml$^{-1}$ IC$_{50}$, under conditions described herein. In some embodiments, the heparin compound is susceptible to Stablin-2 mediated endocytosis at a rate of 15% or more. In some embodiments, the anticoagulant activity of the heparin compound is partially reversible by protamine, wherein a heparin compound having anticoagulant activity that is reversible at a rate of 50% or more in the presence of 20 ug/ml or less of protamine is partially reversible.

In some embodiments, provided herein are methods of synthesizing a heparin compound, comprising providing a monosaccharide substrate, elongating the monosaccharide substrate to a hexasaccharide using enzymes N-acetyl glucosaminyl transferase and heparosan synthase-2, and substrates glucuronic acid (GlcUA) and N-trifluoroacetyl glucosamine (GlcNTFA), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, epimerizing the hexasaccharide using C$_5$-epimerase (C$_5$-epi), sulfating the hexasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, to provide the hexasaccharide:

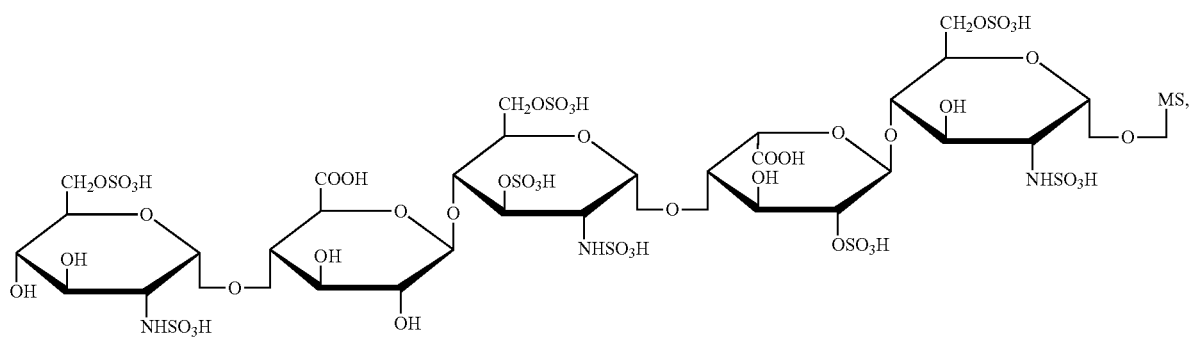

where MS means monosaccharide, elongating the hexasaccharide substrate to a heptasaccharide using heparosan synthase-2 and the substrate glucuronic acid (GlcUA), elongating the heptasaccharide substrate to a octasaccharide using N-acetyl glucosaminyl transferase and substrate and N-trifluoroacetyl glucosamine (GlcNTFA), epimerizing the octasaccharide using $C_5$-epimerase ($C_5$-epi), sulfating the octasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, elongating the octasaccharide substrate to a decasaccharide using heparosan synthase-2 and N-acetyl glucosaminyl transferase, and using the substrates glucuronic acid (GlcUA) and N-trifluoroacetyl glucosamine (GlcNTFA), epimerizing the decasaccharide using $C_5$-epimerase ($C_5$-epi), sulfating the decasaccharide using 2-O-sulfotransferase (2-OST) and 3'-phosphoadenosine 5'-phosphosulfate (PAPS), converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), and a base, optionally lithium hydroxide, elongating the decasaccharide substrate to a dodecasaccharide using heparosan synthase-2 and N-acetyl glucosaminyl transferase, and using the substrates glucuronic acid (GlcUA) and N-trifluoroacetyl glucosamine (GlcNTFA), epimerizing the dodecasaccharide using $C_5$-epimerase ($C_5$-epi), sulfating the dodecasaccharide using 2-O-sulfotransferase (2-OST) and 3'-phosphoadenosine 5'-phosphosulfate (PAPS), sulfating the dodecasaccharide using a 6-O-sulfotransferase (6-OST), optionally 6-O-sulfotransferase 1 and/or 3 (6-OST-1 and/or 6-OST-3), and 3'-phosphoadenosine 5'-phosphosulfate (PAPS), sulfating the dodecasaccharide using a 3-O-sulfotransferase (3-OST), optionally 3-O-sulfotransferase 1 (3-OST-1), and 3'-phosphoadenosine 5'-phosphosulfate (PAPS), and sulfating the dodecasaccharide using a 3-O-sulfotransferase (3-OST), optionally a 3-O-sulfotransferase-5 (3-OST-5), and 3'-phosphoadenosine 5'-phosphosulfate (PAPS), wherein a heparin compound is synthesized.

In some embodiments, the heparin compound produced by this method has anticoagulant activity. In some embodiments, the heparin compound has a binding affinity to antithrombin ranging from about 12 nM to about 44 nM. In some embodiments, the heparin compound has anti-Xa activity of about 10 $ngml^{-1}$ $IC_{50}$ to about 30 $ngml^{-1}$ $IC_{50}$, optionally about 21 $ngml^{-1}$ $IC_{50}$, under conditions described herein. In some embodiments, the heparin compound is susceptible to Stablin-2 mediated endocytosis at a rate of 15% or more. In some embodiments, the anticoagulant activity of the heparin compound is reversible by protamine at a rate of 50% or more in the presence of 20 ug/ml or less of protamine.

In some embodiments, provided herein are methods of treating a subject, the methods comprising providing a subject to be treated, administering to the subject a heparin compound having anticoagulant activity, wherein the heparin compound comprises a heparin compound as disclosed herein, or wherein the heparin compound comprises a synthetic, low-molecular weight heparin compound with reversible anticoagulant activity, wherein the anticoagulant activity of the heparin compound is reversible by protamine, wherein the anticoagulant activity is reversed by about 50% or more in the presence of 1 ug/ml of protamine. In some embodiments, the subject can suffer from venous thromboembolism. In some embodiments, the subject can be renal-impaired. In some embodiments, the subject can be a human subject.

In some embodiments, provided herein are methods of treating a subject in need of anticoagulant therapy, the method comprising providing a subject in need of anticoagulant therapy, administering to the subject a heparin compound having anticoagulant activity, monitoring the subject for heparin-induced thrombocytopenia, and administering to the subject an antidote to reverse the anticoagulant activity of the heparin compound if the subject suffers from heparin-induced thrombocytopenia. In some embodiments, the subject suffers from venous thromboembolism. In some embodiments, the subject is renal-impaired. In some embodiments, the subject is a human subject. In some embodiments, the antidote to reverse the anticoagulant activity of the heparin compound is protamine.

In some embodiments, provided herein are synthetic, low-molecular weight heparin compounds with reversible anticoagulant activity, wherein the anticoagulant activity of the heparin compound is reversible by protamine, wherein the anticoagulant activity is reversed by about 50% or more in the presence of 1 ug/ml of protamine.

In some embodiments, provided herein are synthetic, low-molecular weight heparin compounds susceptible to liver-mediated clearance from circulation. In some embodiments, the heparin compound can be susceptible to Stablin-2 mediated endocytosis at a rate of 15% or more. In some embodiments, the heparin compound is suitable for administration to renal-impaired patients. In some embodiments, the heparin compound comprises at least one 3-O sulfate. In some embodiments, the heparin compound is a dodecamer.

Accordingly, it is an object of the presently disclosed subject to provide low molecular weight heparins that have a reversible anticoagulant activity and methods for synthesizing the same.

An object of the presently disclosed subject matter having been stated hereinabove, and which is achieved in whole or in part by the presently disclosed subject matter, other objects will become evident as the description proceeds when taken in connection with the accompanying drawings and examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to embodiments set forth in the illustrations of the accompanying drawings. Although the illustrated embodiments are merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIG. 1B, Compound 2; FIG. 1C, Compound 3; FIG. 1D, Compound 4; FIG. 1E, Compound 5; FIG. 1F, Compound 6; FIG. 1G, Compound 7; FIG. 1H, Compound 8; FIG. 1I, Compound 9);

FIG. 4A is a histogram of the percentage of $^{35}$S-labeled synthetic LMWHs that was retained in the liver in a mouse model. In comparison to compound 1, all tested compounds, with the exception of compound 2 and enoxaparin, showed significantly higher retention in liver (****P<0.0001). FIG. 4B plots FXa activity of synthetic LMWHs in the presence of different concentrations of protamine under in vitro conditions. FIG. 4C is a histogram of ex vivo reversibility of anti-FXa activity by protamine. The inhibition of FXa activity by the test compounds was significantly affected in the presence of protamine (*P<0.05 and **P<0.0001). Data presented in FIGS. 4A-4C are the average of three to five determinations±s.d. FIG. 4D plots the effect of Compound 5 and protamine on tail-bleeding time after tail transection. Protamine significantly shortened the primary bleeding time (P<0.01) that was induced by compound 5. Each data point represents the measured value from an individual mouse in the test group;

DETAILED DESCRIPTION

Figure 1:
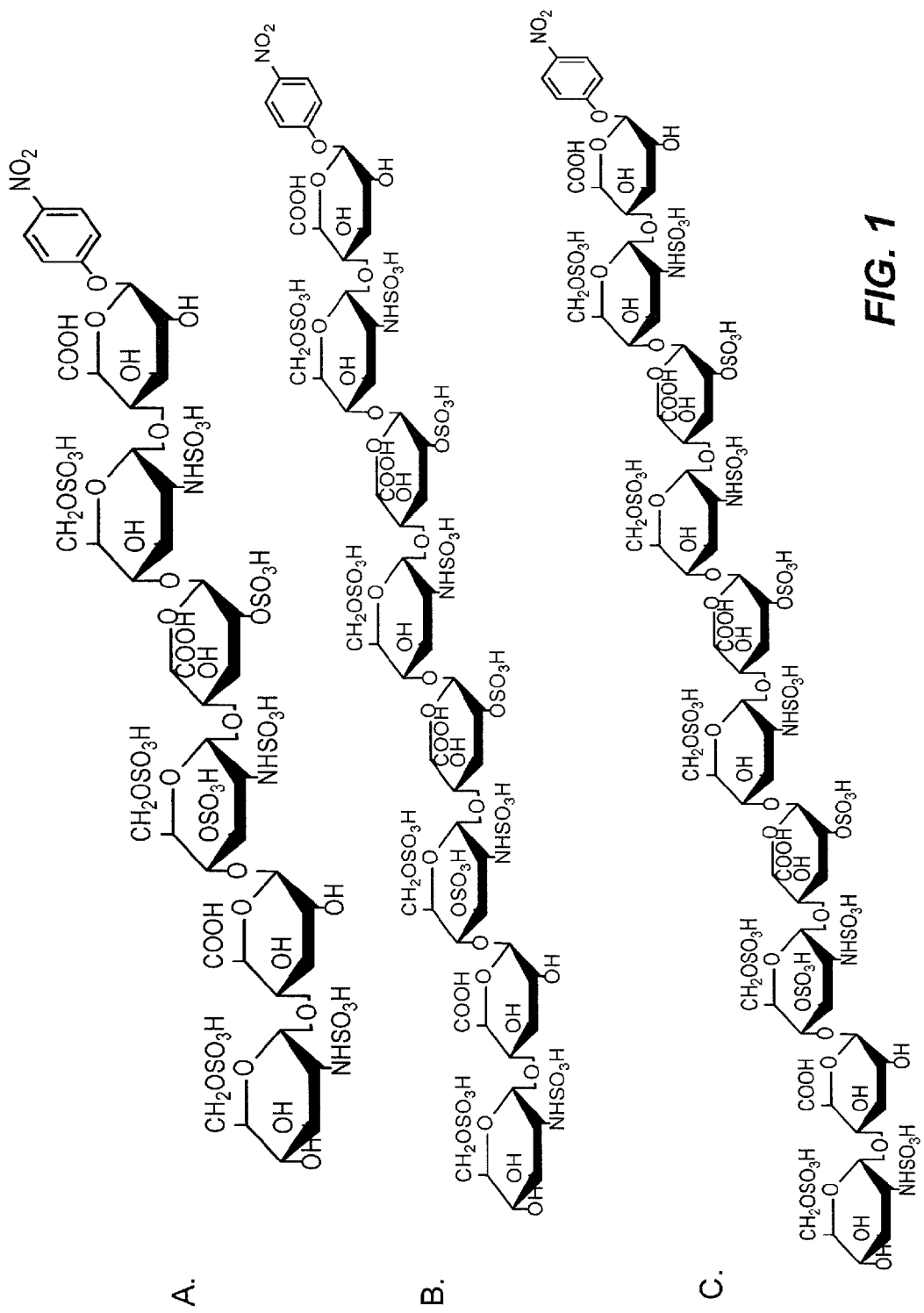
FIGS. 1A-1I illustrate the chemical structures of Compounds 1-9 (FIG. 1A, Compound 1.
Figure 1:
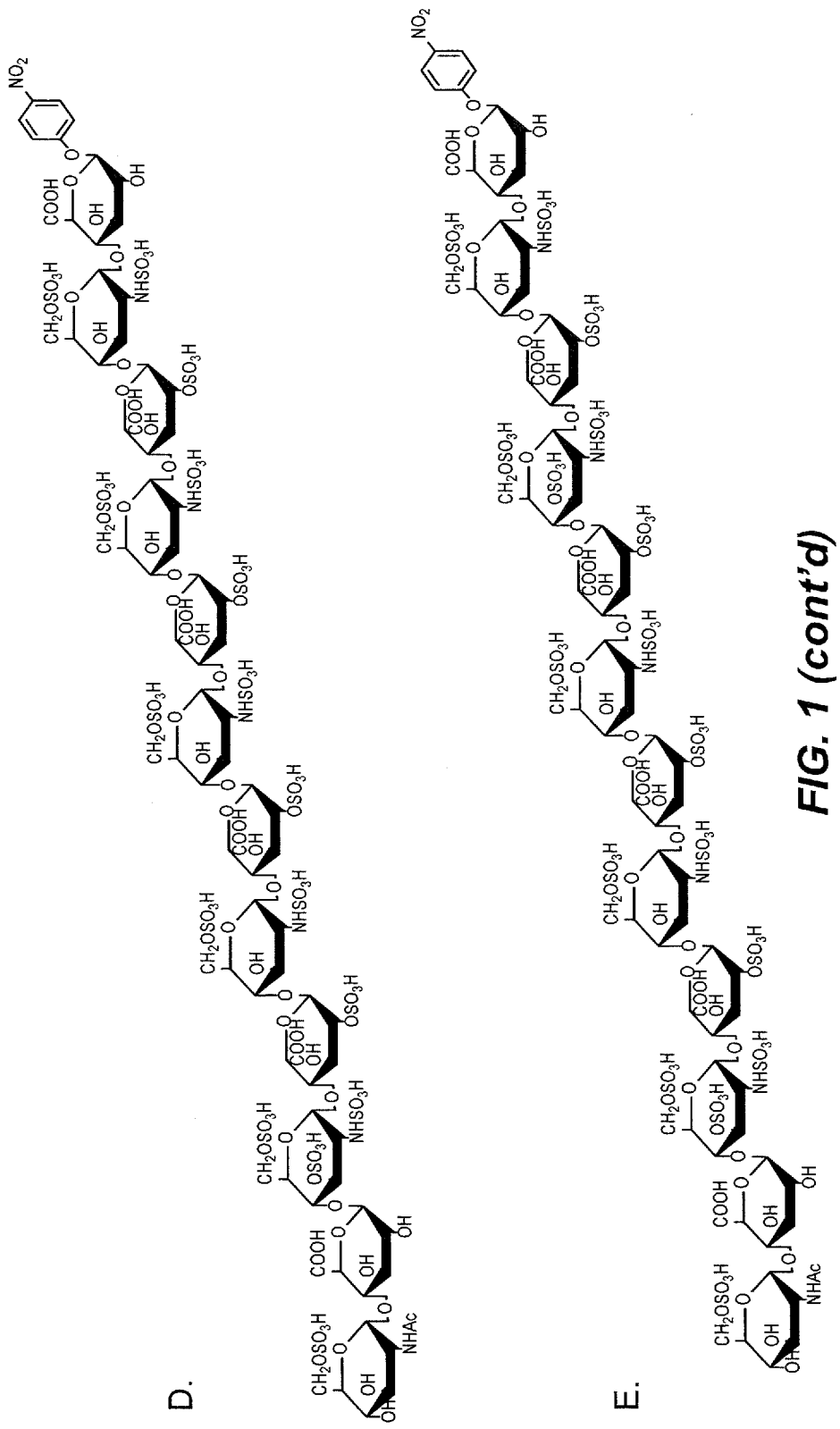
Figure 1:
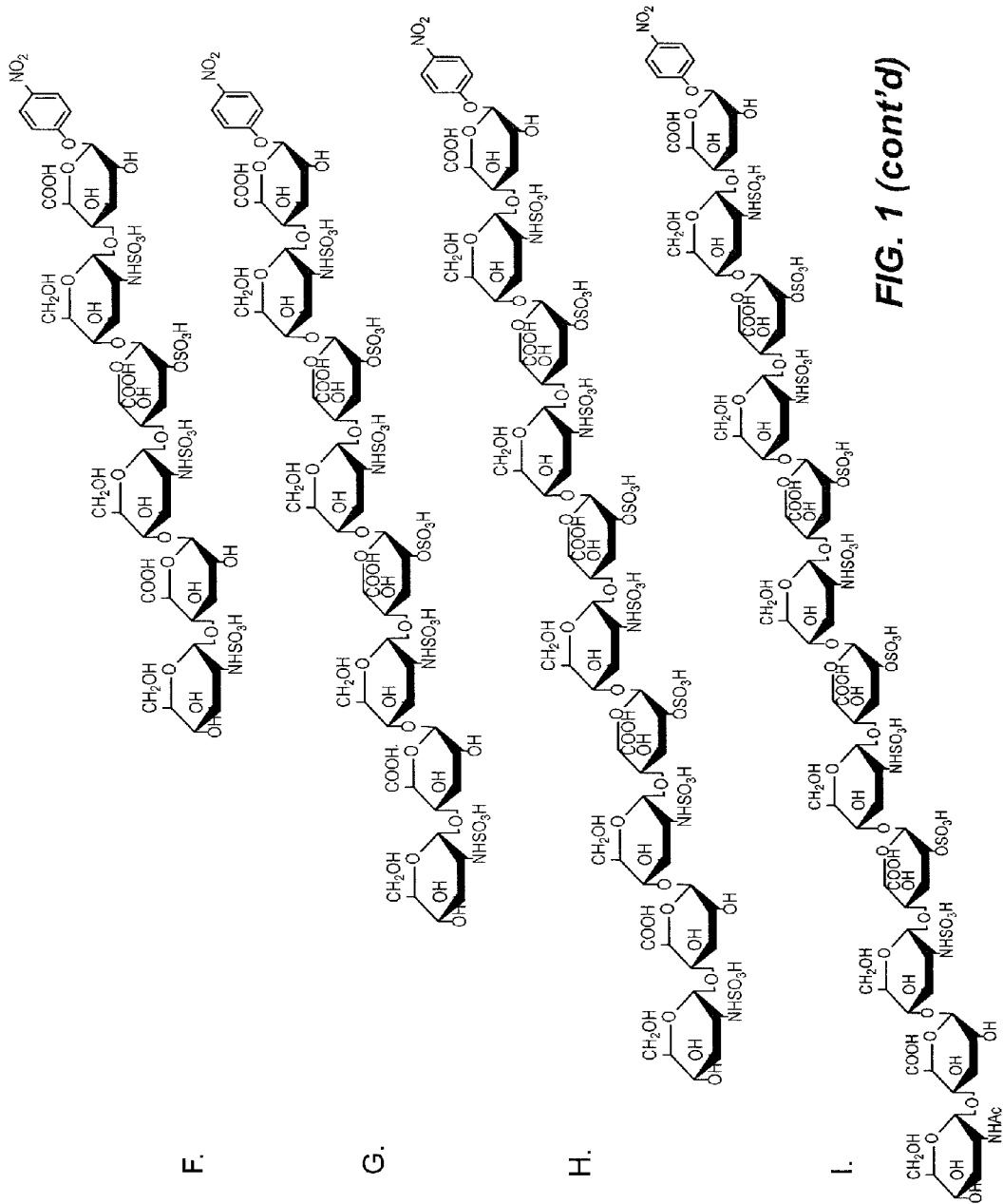

Throughout the specification and claims, a given chemical formula or name shall encompass all optical isomers and stereoisomers, as well as racemic mixtures where such isomers and mixtures exist.

I. Definitions

Unless otherwise indicated, all numbers expressing quantities of ingredients, reaction conditions, and so forth used in the specification of the presently disclosed subject matter are to be understood as being modified in all instances by the term "about". The term "about", as used herein when referring to a measurable value such as an amount of mass, weight, time, volume, temperature, pressure, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods. Accordingly, unless indicated to the contrary, the numerical parameters set forth in this specification of the presently disclosed subject matter are approximations that can vary depending upon the desired properties sought to be obtained by the presently disclosed subject matter.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a Compound or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the terms "heparins", "heparin compound", "HS", "HS-like compound", and "HS-like molecule" are intended to refer to synthetically sulfated polysaccharides possessing one or more structural and/or functional properties of heparan sulfates. In some embodiments, heparin compounds can contain glucuronic acid or iduronic acid and glucosamine with or without sulfo groups. As such, heparin compounds include, but are not limited to, synthetic HSs, sulfated polysaccharides and heparins.

II. Abbreviations

HS heparan sulfate
LMWH low molecular weight heparin
NST N-sulfotransferase
PmHS2 heparosan synthase 2 from *Pasteurella multocida*
KfiA N-acetylglucosaminyl transferase from *E. coli* K5 strain
$C_5$-epi glucuronyl $C_5$-epimerase
2-OST 2-O-sulfotransferase
6-OSTs 6-O-sulfotransferase isoform 1 and isoform 3
3-OST-1 3-O-sulfotransferase isoform 1
3-OST-5 3-O-sulfotransferase isoform 5
NTFA N-trifluoroacetyl
GlcNTFA N-trifluoroacetylated glucosamine
GlcA glucuronic acid
IdoA2S 2-O-sulfated iduronic acid
GlcNS N-sulfoglucosamine
GlcNAc N-acetylated glucosamine
UFH Unfractionated heparin

III. General Considerations

Heparan sulfates (HSs) are highly sulfated polysaccharides present on the surface of mammalian cells and in the extracellular matrix in large quantities. HS is a highly charged polysaccharide comprising 1→4-linked glucosamine and glucuronic/iduronic acid units that contain both N- and O-sulfo groups. Heparin, a specialized form of HS, is a commonly used anticoagulant drug. Thus, "heparan sulfate", as used herein, includes heparin.

Figure 2:
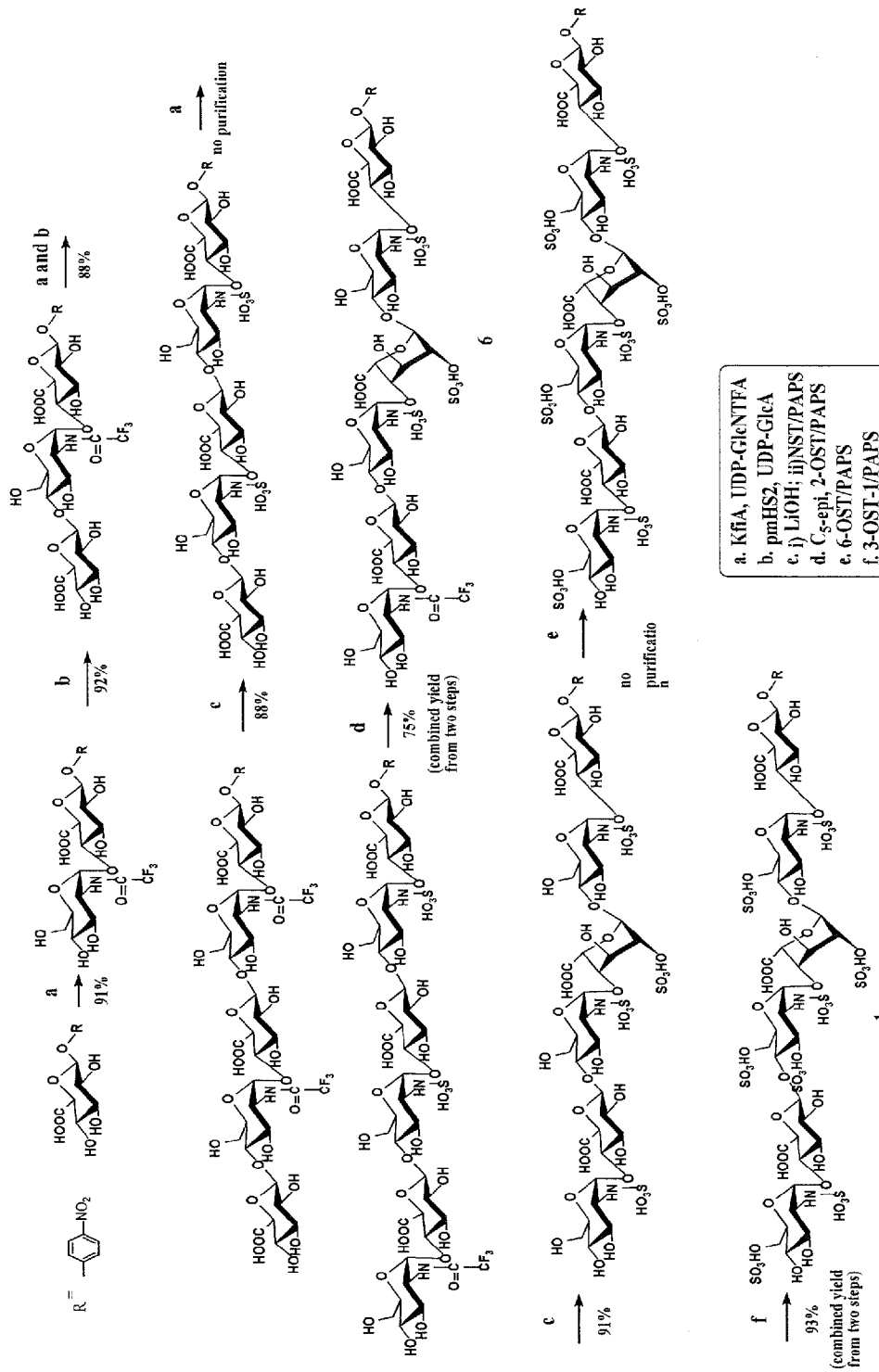
FIG. 2 is schematic illustration of the synthesis of Compound 1 and 6.

Heparin is a polysaccharide that comprises a disaccharide-repeating unit of either iduronic acid (IdoA) or glucuronic acid (GlcA) and glucosamine residues, each capable of carrying sulfo groups. The locations of the sulfo groups, IdoA and GlcA dictate the anticoagulant activity of heparin. In vivo, heparin is synthesized by a series of heparan sulfate (HS) biosynthetic enzymes (FIG. 2). HS polymerase catalyzes the formation of the polysaccharide backbone, a repeating disaccharide of GlcA and N-acetylated glucosamine (GlcNAc). This backbone is then modified by N-deacetylase/N-sulfotransferase (NDST), $C_5$-epimerase ($C_5$-epi), 2-O-sulfotransferase (2-OST), 6-O-sulfotransferase (6-OST), and 3-O-sulfotransferase (3-OST). The availability of recombinant forms of HS biosynthetic enzymes offers a new strategy to prepare heparin polysaccharides and oligosaccharides. Traditionally, heparin oligosaccharides have been chemically synthesized through lengthy routes. Although several synthetic strategies have been reported, the chemical synthesis of heparin oligosaccharides is extremely challenging, especially for oligosaccharides larger than octasaccharides having a high content of sulfo groups. Chemoenzymatic methods have significantly simplified the synthesis, offering a practical approach to prepare synthetic LMWHs.

Heparin compounds of the presently disclosed subject matter can comprise a synthetically sulfated polysaccharide possessing one or more structural and/or functional properties of heparan sulfates. Although exemplary embodiments of particular heparin compounds have been disclosed herein, the presently disclosed subject matter is not intended to be limited to the disclosed examples, but rather heparin compounds include all comparable synthetically sulfated polysaccharides as would be apparent to one of ordinary skill. Indeed, one of ordinary skill in the art, upon a review of the instant disclosure, is capable of producing numerous heparin compounds based upon the disclosed methods and compounds.

Heparins play roles in a variety of important biological processes, including assisting viral infection, regulating blood coagulation and embryonic development, suppressing tumor growth, and controlling the eating behavior of test subjects by interacting with specific regulatory proteins (Liu, J., and Thorp, S. C. (2002) Med. Res. Rev. 22:1-25; Rosenberg, R. D., et al., (1997) J. Clin. Invest. 99:2062-2070; Bernfield, M., et al., (1999) Annu. Rev. Biochem. 68:729-777; Alexander, C. M., et al., (2000) Nat. Genet. 25:329-332; Reizes, O., et al., (2001) Cell 106:105-116). The unique sulfated saccharide sequences can determine to which specific proteins heparins bind, thereby regulating biological processes.

The biosynthesis of heparin occurs in the Golgi apparatus. It can initially be synthesized as a copolymer of glucuronic acid and N-acetylated glucosamine by D-glucuronyl and N-acetyl-D-glucosaminyltransferase, followed by various modifications (Lindahl, U., et al., (1998) J. Biol. Chem. 273:24979-24982). These modifications can include N-deacetylation and N-sulfation of glucosamine, $C_5$ epimerization of glucuronic acid to form iduronic acid residues, 2-O-sulfation of iduronic and glucuronic acid, as well as 6-O-sulfation and 3-O-sulfation of glucosamine. Several enzymes that are responsible for the biosynthesis of HS have been cloned and characterized (Esko, J. D., and Lindahl, U. (2001) J. Clin. Invest. 108:169-173).

The expression levels of various HS biosynthetic enzyme isoforms contribute to the synthesis of specific saccharide sequences in specific tissues. HS N-deacetylase/N-sulfotransferase, 3-O-sulfotransferase, and 6-O-sulfotransferase are present in multiple isoforms. Each isoform is believed to recognize a saccharide sequence around the modification site in order to generate a specific sulfated saccharide sequence (Liu, J., et al., (1999) J. Biol. Chem. 274:5185-5192; Aikawa, J.-I., et al., (2001) J. Biol. Chem. 276:5876-5882; Habuchi, H., et al., (2000) J. Biol. Chem. 275:2859-2868). For instance, HS D-glucosaminyl 3-O-sulfotransferase (3-OST) isoforms generate 3-O-sulfated glucosamine residues that are linked to different sulfated iduronic acid residues. 3-OST isoform 1 (3-OST-1) transfers sulfate to the 3-OH position of an N-sulfated glucosamine residue that is linked to a glucuronic acid residue at the nonreducing end (GlcUA-GlcNS±6S). However, 3-OST isoform 3 (3-OST-3) transfers sulfate to the 3-OH position of an N-unsubstituted glucosamine residue that is linked to a 2-O-sulfated iduronic acid at the nonreducing end (IdoUA2S-GlcNH$_2$±6S) (Liu, J., et al., (1999) J. Biol. Chem. 274:38155-38162). The difference in the substrate specificity of 3-OSTs results in distinct biological functions. For example, the HS modified by 3-OST-1 binds to antithrombin (AT) and possesses anticoagulant activity (Liu, J., et al., (1996) J. Biol. Chem. 271:27072-27082). However, the HS modified by 3-OST-3 (3-OST-3A and 3-OST-3B) binds to glycoprotein D (gD) of herpes simplex virus, type 1, (HSV-1) thus mediating viral entry (Shukla, D., et al., (1999) Cell 99:13-22).

Cell surface HS also assists HSV-1 infection (WuDunn, D., and Spear, P. G. (1989) J. Virol. 63:52-58). One report (Shukla, D., et al., (1999) Cell 99:13-22) suggests that a specific 3-O-sulfated HS is involved in assisting HSV-1 entry. The 3-O-sulfated HS is generated by 3-OST-3 but not by 3-OST-1. In addition, the 3-O-sulfated HS provides binding sites for HSV-1 envelope glycoprotein D, which is a key viral protein involved in the entry of HSV-1 (Shukla, D., et al., (1999) Cell 99:13-22). Because 3-OST-3-modified HS is rarely found in HS from natural sources, the study suggests that HSV-1 recognizes a unique saccharide structure. Indeed, the result from the structural characterization of a gD-binding octasaccharide revealed that the octasaccharide possesses a specific saccharide sequence (Liu, J., et al., (2002) J. Biol. Chem. 277:33456-33467). In addition, the binding affinity of the 3-O-sulfated HS for gD is about 2 µM (Shukla, D., et al., Cell 99:13-22). This affinity is similar to that reported for the binding of gD to the protein receptors, suggesting that HSV-1 utilizes both protein and HS cell surface receptors to infect target cells (Willis, S. H., et al., (1998) J. Virol. 72:5938-5947; Krummenacher, C., et al., (1999) J. Virol. 73:8127-8137). It is believed that the interaction between gD and the 3-O-sulfated protein entry receptors somehow triggers the fusion between the virus and the cell in the presence of other viral envelope proteins, including gB, gH, and gL (Shukla, D., and Spear, P. G. (2001) J. Clin. Invest. 108:503-510). A study of the co-crystal structure of gD and herpes entry receptor HveA suggests that the binding of HveA to gD induces conformational changes in gD (Carfi, A., et al., (2001) Mol. Cell 8:169-179).

HS-regulated anticoagulation mechanisms have been studied extensively. It is now known that HS, including heparin, interact with AT, a serine protease inhibitor, to inhibit the activities of thrombin and factor Xa in the blood coagulation cascade (Rosenberg, R. D., et al., (1997) *J. Clin. Invest.* 99:2062-2070). Anticoagulant-active HS ($HS^{act}$) and heparin contain one or multiple AT-binding sites per polysaccharide chain. This binding site contains a specific pentasaccharide sequence with a structure of -GlcNS(or Ac)6S-GlcUA-GlcNS3S(±6S)-IdoUA2S-GlcNS6S-. The 3-O-sulfation of glucosamine for generating GlcNS3S(±6S) residue, which is carried out by 3-OST-1, plays a role in the synthesis of $HS^{act}$ (Liu, J., et al., (1996) *J. Biol. Chem.* 271:27072-27082; Shworak, N. W., et al., (1997) *J. Biol. Chem.* 272:28008-28019).

IV. Heparin Compounds

In accordance with some embodiments, heparin compounds of the presently disclosed subject matter can have a strong binding affinity for AT. By way of non-limiting example, the binding constant ($K_d$) of heparin compounds of the presently disclosed subject matter can range from about 3 to about 100 nM. In some embodiments, the binding constant ($K_d$) of a heparin compound of the presently disclosed subject matter can range from about 5 to about 40 nM. Any suitable approach to determine binding affinity can be employed as would be appreciated by one of ordinary skill in the art upon review of the instant disclosure.

In some embodiments, heparin compounds disclosed herein can have a molecular weight ranging from about 1,500 daltons (Da) to about 6,000 Da. In some embodiments, the term low molecular weight (LMW) heparin, is intended to refer to a heparin compound ranging in size from 3,500 to 6,000 Da and having from about 12 to 20 saccharide units, and in some embodiments having anticoagulant activity. In some embodiments, a LMW heparin of the presently disclosed subject matter can be about 3,500 Da, about 4,000 Da, about 4,500 Da, about 5,000 Da, about 5,500 Da, or about 6,000 Da. In some embodiments, a LMW heparin of the presently disclosed subject matter can have 12, 14, 16, 18 or 20 saccharide units. In some embodiments, a LMW heparin of the presently disclosed subject matter can have anticoagulant activity that is reversible in the presence of an antidote, such as for example protamine.

In some embodiments the anticoagulant activity can be measured by determining anti-Xa and anti-IIa activities. In some embodiments, the anti-Xa and anti-IIa activities can be determined in the presence of antithrombin. Heparin compounds with a strong binding affinity for AT and/or a high anticoagulant activity can have high anti-Xa and anti-IIa activities. In some embodiments, heparin compounds with high anticoagulant activity can have $IC_{50}$ values for anti-Xa activity ranging from about 1 to about 20 nM. In some embodiments, heparin compounds with high anticoagulant activity can have $IC_{50}$ values for anti-Xa activity ranging from about 1 to about 10 nM. In some embodiments, heparin compounds with high anticoagulant activity can have $IC_{50}$ values for anti-Xa activity ranging from about 1 to about 5 nM. In some embodiments, heparin compounds with high anticoagulant activity can have $IC_{50}$ values for anti-Xa activity ranging from about 10 $ngml^{-1}$ to about 40 $ngml^{-1}$, under the conditions disclosed herein. In some embodiments, heparin compounds with high anticoagulant activity can have $IC_{50}$ values for anti-Xa activity ranging from about 15 $ngml^{-1}$ to about 35 $ngml^{-1}$, under the conditions disclosed herein. As would be appreciated by one of ordinary skill in the art, $IC_{50}$ values are relative to the conditions under which the measurements are taken. As such, the $IC_{50}$ values expressed herein are relative to the conditions under which the measurements were taken and can therefore be adjusted accordingly as would be understood by one of ordinary skill in the art. Any suitable approach to determine anticoagulant activity can be employed as would be appreciated by one of ordinary skill in the art upon review of the instant disclosure.

In some embodiments, the disclosed heparin compounds can have an anticoagulant activity that is reversible in the presence of a reversing agent, such as for example protamine. In some embodiments, a heparin compound can have an anticoagulant activity that is completely reversible, substantially completely reversible, or at least partially reversible by protamine. In some embodiments, a heparin compound having anticoagulant activity that is reversible at a rate of 50% or more in the presence of 20 ug/ml or less of protamine is partially reversible. In some embodiments, a heparin compound having anticoagulant activity that is reversible at a rate of 50% or more in the presence of 100 ug/ml or less, 50 ug/ml or less, 30 ug/ml or less, 20 ug/ml or less, 15 ug/ml or less, 10 ug/ml or less, 5 ug/ml or less, or 1 ug/ml or less of protamine is partially reversible. In some embodiments, a heparin compound of the present disclosure is considered to have a reversible anticoagulant activity if the anticoagulant activity of the heparin compound is reversible at a rate similar to that of unfractionated heparin, as would be appreciated by one of ordinary skill in the art upon a review of the instant disclosure.

An important clinical benefit of the disclosed heparin compounds is their ability to be cleared from the circulation through the liver, allowing these agents to be used in renal-impaired patients. Unfractionated heparin (UFH) and larger chained heparin compounds can bind to stabilin-2, a scavenger receptor present on liver sinusoidal endothelial cells that mediates their clearance. In some embodiments, the disclosed heparin compounds displayed significant endocytosis mediated by Stabilin-2 as measured in a cell-based assay.

As shown by Pempe et al, 2012, heparin compounds with a 3-O sulfation can be more efficiently taken up and cleared by liver. See also Yu et al, 2014. In accordance with some aspects of the presently disclosed subject matter, the sulfation pattern of the presently disclosed heparin compounds can impact the clearance of such compounds through the liver. Thus, in some embodiments, a synthetic, low-molecular weight heparin compound susceptible to liver-mediated clearance from circulation comprises a 3-O sulfation. In some aspects, heparin compounds disclosed herein that are dodecamers or longer with a 3-O sulfation can have such enhanced liver clearance. In some embodiments, provided is a sulfation pattern, such as a 3-O sulfation pattern, in a synthetic, low-molecular weight heparin compound, such as a dodecamer or larger synthetic oligosaccharide, which matches the requirements for rapid liver clearance.

Thus, in some embodiments, heparin compounds of the presently disclosed subject matter can be susceptible to Stablin-2 mediated endocytosis, wherein a heparin compound that is endocytosed at a rate of 15% or more is susceptible to Stablin-2 mediated endocytosis. In some embodiments, a heparin compound that is endocytosed at a rate of 20%, 25%, 30%, 35%, 40%, 45%, 50%, 75%, 90% or more is susceptible to Stablin-2 mediated endocytosis. Thus, provided in some aspects are synthetic, low-molecular weight heparin compounds susceptible to liver-mediated clearance from circulation. In some embodiments, the heparin compounds can be susceptible to Stablin-2 mediated endocytosis at a rate of 15% or more. Due to these characteristics, in some aspects the disclosed heparin compounds can be suitable for administration to renal-impaired patients.

In some aspects, such heparin compounds that are susceptible to liver-mediated clearance from circulation comprises a sulfation pattern, such as a 3-O sulfation pattern, such at least one 3-O sulfate, and in some aspects can be a dodecamer.

Five homogenous LMWHs (Compounds 1-5, FIGS. 1A-1E, respectively), ranging from hexa- to dodeca-saccharide, can be synthesized. The structures of Compounds 1-4 differ at their reducing ends, containing a different number of -IdoA2S-GlcNS6S- repeating units. Dodecasaccharide 5 differs from 4, as it has two 3-O-sulfo groups (FIGS. 1D and 1E). The synthesis of Compound 1 can in some embodiments be initiated from a commercially available monosaccharide, 1-O-(para-nitrophenyl) glucuronide (GlcA-pnp) (FIG. 2). Elongation of GlcA-pnp to a hexasaccharide can be accomplished using two bacterial glycosyltransferases: KfiA (N-acetylglucosaminyl transferase from E. coli K5 strain) and heparosan synthase 2 (pmHS2) from Pasteurella multocida. The subsequent N-sulfation, O-sulfations and epimerization steps permitted to prepare Compound 1. The approach can also afford for the synthesis of hexasaccharide 6, an intermediate for subsequent syntheses.

Figure 3:
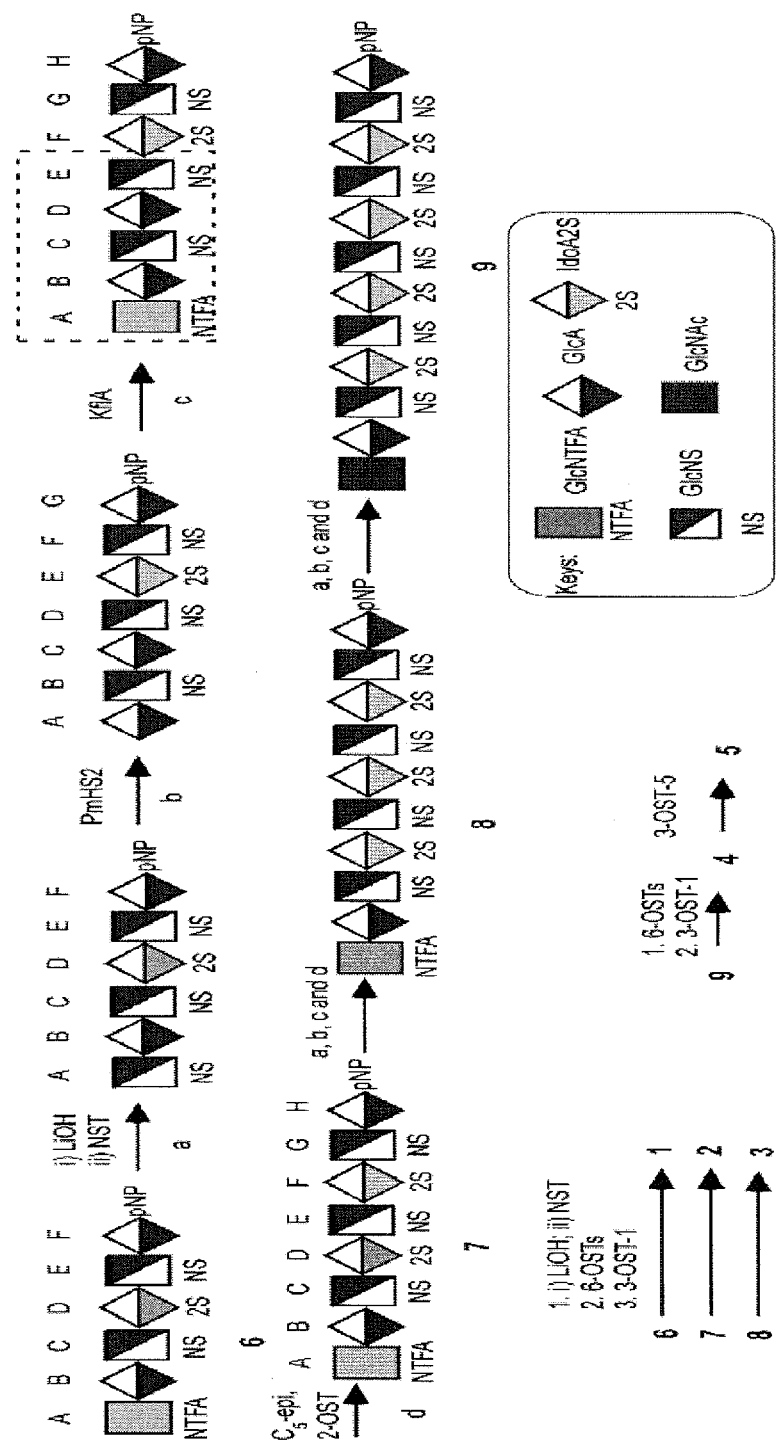
FIG. 3 is a schematic illustration of the synthesis of synthetic LMWHs as disclosed herein. The synthesis can in some aspects be initiated from a hexasaccharide (Compound 6), which can be converted to an octasaccharide (Compound 7), decasaccharide (Compound 8) and dodecasaccharide (Compound 9) to synthesize Compounds 2, 3, and 4, respectively. The conversion of Compound 4 to 5 can be achieved by 3-OST-5 modification.

The synthesis of Compounds 2, 3, and 4 can be initiated from hexasaccharide 6 through intermediates 7, 8 and 9, respectively (FIG. 3). These intermediates contain multiple -IdoA2S-GlcNS6S- repeating units, posing a synthetic challenge due to the substrate specificity of $C_5$-epi[25].

FIG. 3 is a schematic illustration of the synthesis of synthetic LMWHs as disclosed herein, and particularly the synthesis of Compounds 2 to 5. The synthesis can be initiated from a hexasaccharide 6. The hexasaccharide can be converted to an octasaccharide (7), decasaccharide (8) and dodecasaccharide (9) to synthesize Compounds 2, 3, and 4, respectively. The conversion of Compounds 4 to 5 can be achieved by 3-OST-5 modification.

The synthesis of intermediates, including Compounds 7, 8 and 9, can in some aspects follow this scheme to avoid yielding mixtures of products. When mixtures are formed, the synthetic efficiency will decrease dramatically. Because many steps involved in the synthesis, only symbols are presented to represent the synthesis. The chemical structures of Compounds 1-9 are shown in FIGS. 1A-1I, respectively.

A carefully designed sequence of enzymatic steps can be employed for high purity and yields. The conversion of GlcA to IdoA2S involves two steps: the $C_5$-epi catalyzed epimerization of a GlcA to an IdoA; and 2-OST transferred a sulfo group to the IdoA residue. $C_5$-epi catalyzes both the forward and reverse reactions, leading to the incomplete conversion of GlcA to IdoA2S[26] and a complex mixture of products[27]. The placement of a pentasaccharide domain, GlcN-trifluoroacetyl(TFA)-GlcA-GlcNS-GlcA-GlcNS-, into the substrate, directs $C_5$-epi to irreversibly react only with one GlcA residue (shown in bold) and avoids incomplete conversion.

The conversion of Compound 6 to 7, involving the compound of the pentasaccharide domain recognized by $C_5$-epi, can be completed in four steps. The GlcNTFA residue (Residue F) of hexasaccharide 6 can first be converted to a GlcNS residue (Step a, FIG. 3). The hexasaccharide can then elongated to an octasaccharide in two enzymatic steps (step b and c, FIG. 3), to obtain the desired pentasaccharide domain, as depicted in the dashed box (FIG. 3). The conversion of GlcA (Residue E) to IdoA2S to yield 7 can then achieved by $C_5$-epi and 2-OST (step d, FIG. 3). The formation of IdoA2S residue can remove its reactivity towards further $C_5$-epi modification. Repeating these steps (step a to d, FIG. 3) once or twice can afford 8 and 9, respectively.

In some embodiments, the products of the disclosed and illustrated reactions can contain a pnp tag with a strong absorbance at 310 nm, facilitating purity analysis by high performance liquid chromatography (HPLC). Structures were determined by electrospray ionization mass spectrometry (ESI-MS), one-dimensional (1D) and two-dimensional (2D) nuclear magnetic resonance (NMR) analysis. Diethylaminoethyl (DEAE)-HPLC analysis demonstrates that 5 is of high purity, MS affords an observed mass of 3562.8755, very close to the calculated exact mass of 3562.9087 and observed isotopic distribution for $C_{80}H_{121}N_7O_{115}S_{17}$ matches the simulated distribution. $^1$H-NMR spectrum of 5 depicts the presence of 12 anomeric protons. Additional 1-D NMR and 2-D NMR analysis confirmed the correct glycosidic linkages and led to the spectral assignment of 5. MS-assisted sequence analysis pinpointed the residues carrying 3-O-sulfo groups.

Figure 4:
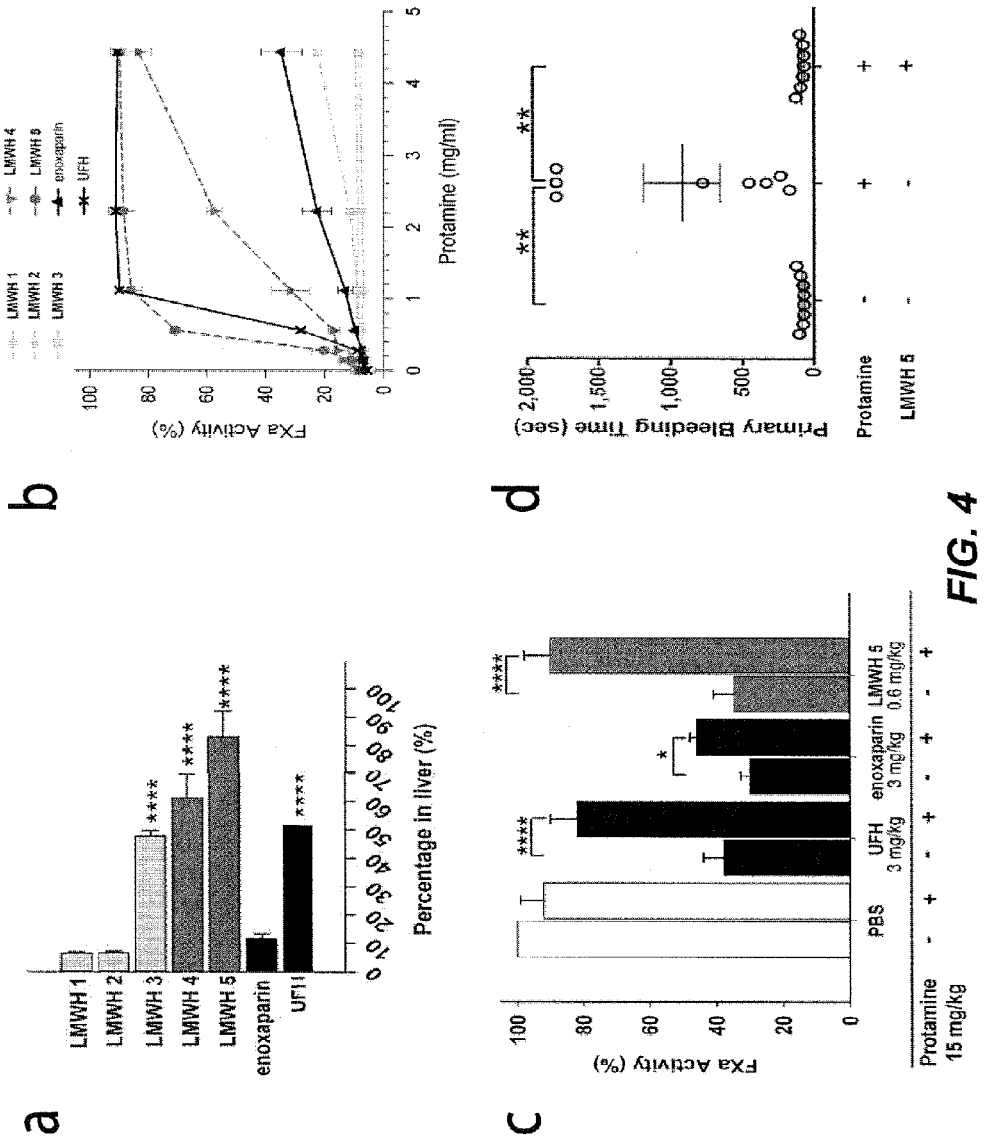
FIGS. 4A-4D are graphical depictions of the data for the determination of the clearance, anti-FXa activity and sensitivity to protamine neutralization of synthetic LMWHs.
Figure 5:
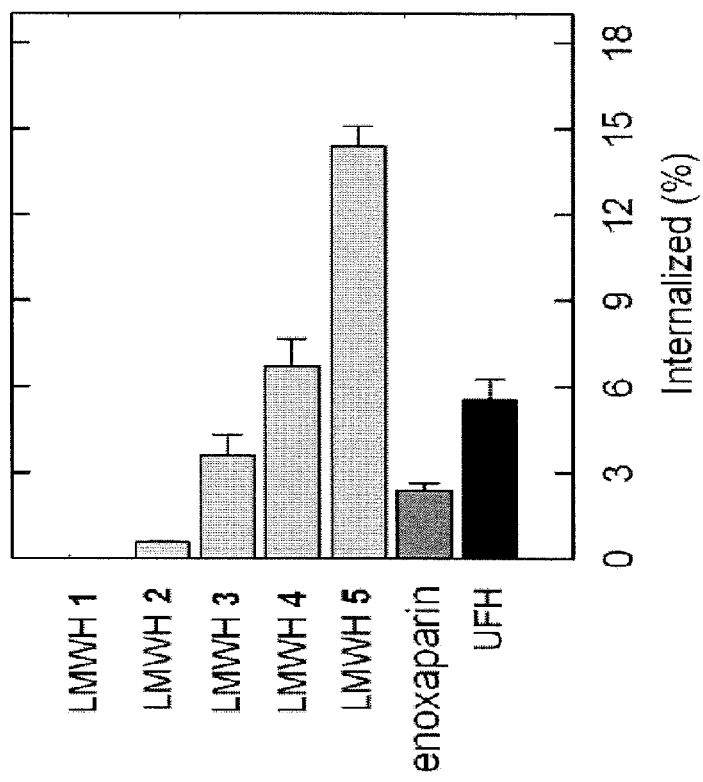
FIG. 5 is a histogram of endocytosis of $^{35}$S-labeled synthetic LMWHs in Flp-In-293 cells. The cells were stably transfected with the plasmid expressing the Stabilin-2 receptor (190-HARE). The internalization value was calculated by subtracting the nonspecific internalization background from the total internalization of a $^{35}$S-labeled Compound. The background was determined by mixing the $^{35}$S-labeled Compound with at least 100-fold molecular excess of unlabeled UFH. All tested compounds, when compared with Compound 1, have significantly higher tendency to endocytosis (****=p<0.0001)

An important clinical benefit of UFH and some LMWH chains is their ability to be cleared from the circulation through the liver, allowing these agents to be used in renal-impaired patients. Synthetic LMWHs were examined to determine if they displayed similar clearance profiles. UFH and larger chains in LMWH are known to bind to stabilin-2, a scavenger receptor present on liver sinusoidal endothelial cells that mediates their clearance. Like UFH and LOVENOX®, Compounds 3, 4 and 5 displayed significant endocytosis mediated by Stabilin-2 as measured in a cell-based assay, while Compounds 1 and 2 displayed very low internalization (FIG. 5). Using a mouse model, the retention of synthesized homogeneous LMWHs in the liver was compared with that of UFH and LOVENOX® (FIG. 4A). Larger Compounds (Compounds 3, 4 and 5) were retained in the liver, while smaller size Compounds (Compounds 1 and 2) showed very low level of retention in the liver (FIG. 5).

Figure 6:
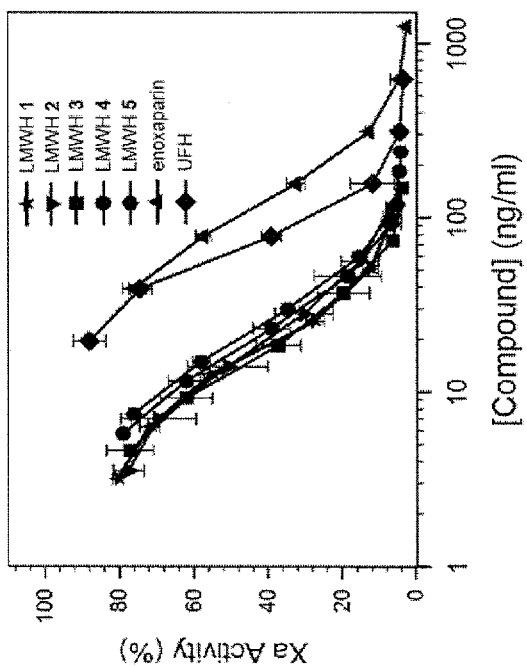
FIG. 6 is a line chart of anti-Xa activity of Compounds 1-5, enoxaparin and UFH.

The anticoagulant activity of synthetic LMWHs was also determined. All compounds (1-5) displayed strong antithrombin (AT)-binding affinity ($K_d$ 5-30 nM) (Table 1). Results of anti-Xa activity assays showed lower $IC_{50}$ values for Compounds 1-5 than UFH and LOVENOX®, confirming their potent anti-Xa activity (FIG. 6 and Table 1). Unlike UFH and LOVENOX®, synthetic LMWHs have no detectable anti-IIa activity, and thus, these compounds are Xa-specific inhibitors. The European Medicines Agency (EMA) recently approved a "second-generation" LMWH, Bemiparin. Bemiparin has significantly lower anti-IIa activity than other LMWH drugs, but has very similar clinical utility, suggesting that the anti-IIa activity of LMWHs is less critical.

Next, the reversibility of the anticoagulant activity by protamine was determined. The in vitro protamine reversibility of five synthetic LMWHs (FIG. 4B) was compared. Unlike Compounds 1, 2, and 3, Compound 4 was partially reversed by protamine. Moreover, Compound 5 showed the same protamine reversibility as UFH and greater reversibility than LOVENOX® (FIG. 4B). Using an ex vivo mouse model, it was confirmed that Compound 5 has similar sensitivity to protamine neutralization as UFH; as expected only partial protamine neutralization was observed for LOVENOX® (FIG. 4C). Finally, using a mouse tail bleeding model, it was demonstrated that protamine shortened the primary bleeding time and reduced the blood loss that was induced by Compound 5 (FIG. 4D), confirming the sensitivity of Compound 5 to protamine neutralization in vivo.

Summarily, FIGS. 4A-4D illustrate that Compounds 3, 4 and 5 are internalized in mice liver, and that the anti-Xa activity of Compound 5 can be reversed by protamine in an in vitro experiment, while the anti-Xa activity of other compounds, including enoxaparin (brand name LOVENOX), is not reversible by protamine. UFH and Compound 5 have similar sensitivity to protamine neutralization. The anti-Xa activity of Compound 5 is reversible in an ex vivo experiment. Enoxaparin is only partially reversible, but UFH is fully reversible. And, the anti-Xa activity of Compound 5 can be reversed in an in vivo experiment.

Heparin and LMWHs are critical for the practice of modern medicine yet their production still depends on a long supply chain, which is vulnerable to contamination and adulteration. After the heparin contamination crisis, the US FDA and EMA have implemented a series of new approaches to monitor the purity of heparin drugs. Although these efforts have stopped the influx of contaminated heparin into the market, a long term solution to secure the safety of the heparin supply chain should be to manufacture synthetic heparin under highly regulated processes, eliminating the needs for animal-sourced heparin. Chemoenzymatic synthesis offers an approach for this goal. The entire synthesis of homogenous LMWHs requires about 20 synthetic steps and is potentially amenable to large-scale manufacturing. We also demonstrate that the synthetic LMWHs have added pharmacological/clinical benefits. The chemoenzymatic synthesis of LMWHs provides avenues for the next generation of heparin therapeutics.

TABLE 1

Summary of the synthesized LMWHs

| Compound | Amount (mg) | Purity (%)[1] | Affinity to antithrombin ($K_d$)[2] | Anti-FXa activity ($IC_{50}$, ngml$^{-1}$)[3] |
|---|---|---|---|---|
| 1 | 5 | ≥99 | 7 + 2 nM | 14 |
| 2 | 6 | ≥99 | 8 + 3 nM | 17 |
| 3 | 6 | ≥99 | 5 + 1 nM | 15 |
| 4 | 70 | ≥99 | 30 + 7 nM | 19 |
| 5 | 17 | ≥99 | 28 + 16 nM | 21 |
| 6 | 461 | ≥99% | —[4] | — |
| 7 | 344 | ≥95% | — | — |
| 8 | 263 | ≥99% | — | — |
| 9 | 183 | ≥99% | — | — |

[1]The purity was determined by DEAE-HPLC analysis.
[2]The $K_d$ values are the average of two or three determinations. The $K_d$ value for fondaparinux was previously reported to be 5.9 + 1.5 nM (Xu, Y. et al. *Science* 334, 498-501, 2011).
[3]$IC_{50}$ represents half maximal inhibitory concentration to inhibit the activity of factor FXa. The $IC_{50}$ value for fondaparinux was previously reported to be 4.5 ngml$^{-1}$ (Xu, Y. et al. *Science* 334, 498-501, 2011). The lower $IC_{50}$ value observed for fondaparinux is ascribed to the different protocols used in the two experiments.
[4]Compound 6-9 have no binding to antithrombin and do not inhibit FXa activity.

V. Chemoenzymatic Synthesis of Ultra-Low Molecular Weight Heparins

In some embodiments the presently disclosed subject matter provides enzymatic approaches to heparin compounds, including structurally homogeneous low molecular weight heparin compounds. The heparin compounds disclosed herein can be synthesized from a monosaccharide building block using an enzymatic approach as disclosed herein.

In some embodiments, the synthesis of heparin compounds according to the presently disclosed subject matter can include backbone elongation and saccharide modification. In some embodiments, the presently disclosed subject matter provides a method of synthesizing a heparin compound, comprising providing a saccharide substrate, elongating the saccharide substrate to a saccharide of a desired or predetermined length, performing an epimerization reaction, and performing one or more sulfation reactions, whereby a heparin compound is synthesized. Alternatively, in some embodiments, the presently disclosed subject matter provides a method of synthesizing a heparin compound, comprising providing a monosaccharide or disaccharide substrate, elongating the monosaccharide or disaccharide substrate to a tetrasaccharide, elongating the tetrasaccharide to a hexasaccharide, wherein the hexasaccharide comprises a N-sulfotransferase substrate residue, converting the N-sulfotransferase substrate residue on the hexasaccharide to a N-sulfo glucosamine (GlcNS) residue performing an epimerization reaction, and performing one or more sulfation reactions selected from the group consisting of a 2-O-sulfation reaction, a 6-O-sulfation reaction, a 3-O-sulfation reaction, and combinations thereof. These steps can be repeated to form a octasaccharide, decasaccharide and/or dodecasaccharide to thereby synthesize a heparin compound as disclose herein.

In some embodiments, the elongation step can comprise employing a glycosyl transferase. By way of example and not limitation, the glycosyl transferase can be N-acetyl glucosaminyl transferase of *E. coli* K5 (KfiA) or heparosan synthase-2 (pmHS2) from *Pasteurella multocida*. In some embodiments, the elongation step can comprise employing one or more monosaccharides, which can comprise, for example, glucuronic acid (GlcUA), N-acetylated glucosamine (GlcNAc), and N-trifluoroacetyl glucosamine (GlcNTFA).

In some embodiments, the step of converting the N-sulfotransferase substrate residue on the hexasaccharide or heptasaccharide to a N-sulfo glucosamine (GlcNS) residue can comprise employing N-sulfotransferase (NST) and 3'-phosphoadenosine 5'-phosphosulfate (PAPS).

To elaborate further, in some embodiments the epimerization reaction can comprise employing $C_5$-epimerase ($C_5$-epi), the 2-O-sulfation reaction can comprise employing 2-O-sulfotransferase (2-OST), the 6-O-sulfation reaction can comprise employing 6-O-sulfotransferase (6-OST), and the 3-O-sulfation reaction can comprise employing 3-O-sulfotransferase (3-OST).

In some embodiments, the elongation steps can comprise using a glycosyl transferase. In some aspects, the glycosyl transferase can be N-acetyl glucosaminyl transferase of *E. coli* K5 (KfiA).

In some embodiments, a sequence of enzymatic steps are provided for synthesizing a dodecasaccharide as disclosed herein in a highly efficient manner. In some embodiments, heparin compound synthesis can be initiated from hexasaccharide and continue through several intermediates until the final heparin compound. These intermediates contain multiple—IdoA2S-GlcNS6S- repeating units, posing a synthetic challenge due to the substrate specificity of $C_5$-epi. A designed sequence of enzymatic steps can be employed for high purity and yields. Particularly, the conversion of GlcA to IdoA2S involves two steps: the $C_5$-epi catalyzed epimerization of a GlcA to an IdoA; and 2-OST transferred a sulfo group to the IdoA residue. $C_5$-epi catalyzes both the forward and reverse reactions, leading to the incomplete conversion of GlcA to IdoA2S[26] and a complex mixture of products. Such reactions can produce substantial amounts of byproducts thereby rendering the process highly inefficient. The placement of a pentasaccharide domain, GlcN-trifluoroacetyl(TFA)-GlcA-GlcNS-GlcA-GlcNS-, into the substrate, directs $C_5$-epi to irreversibly react only with one GlcA residue (shown in bold) and reduces or avoids incomplete conversion.

The conversion of GlcA to IdoA2S can be achieved by $C_5$-epi and 2-OST. The formation of IdoA2S residues between the elongation steps between octasaccharide, decasaccharide, and dodecasaccharide removes its reactivity towards further $C_5$-epi modification. Repeating these steps allows for the elongation up to a dodecasaccharide, and the synthesis of low-molecular weight heparin compounds disclosed herein, while maintaining high efficiency of synthesis. For example, using the synthetic process as disclosed herein can heparin compounds, e.g. a dodecasaccharide, as depicted herein at efficiency rates of 50%, 60%, 70%, 80%, 90% or more. This is in contrast to alternative approaches where a heparin compound is elongated to a desired length, e.g. a dodecasaccharide, and then sulfated, which can yield significantly lower efficiencies, e.g. 2% to 5%.

In some embodiments, a heparin Compound of the presently disclosed subject matter can have an R group that is detectable, for example, has UV or visible light absorbance. Designing and synthesizing a heparin Compound that is detectable, for example has an R group that absorbs UV or visible light, can facilitate product purity detection and isolation. Compounding a heparin compound with a UV or visible light "tag" can facilitate the monitoring of the chemoenzymatic reactions and Compound synthesis. As would be appreciated by one of ordinary skill in the art, detecting a UV or visible light "tag" on a Compound during or after synthesis can be achieved using any number of available spectrophotometric devices. In some embodiments, the "tag" can comprise a para-nitrophenyl.

Alternatively, or in addition, in some embodiments the detectable R group can be a hydrophobic R group. As would be appreciated by one of ordinary skill in the art, a hydrophobic R group can allow the product to bind to a C18-column, which can allow for the purification of the synthesized heparins.

In some embodiments, an R group, such as an R group that has UV or visible light absorbance, or a hydrophobic R group, can be removable when the synthesis of the heparin is completed. As would be appreciated by one of ordinary skill in the art, removing the R group once its utility is achieved can facilitate the final processing of the heparin Compound. For example, in some aspect it might be desirable to remove the R group to avoid potential toxic functional groups entering into a heparin drug compound.

V.A. Enzymes Employed in Chemoenzymatic Synthesis of Heparin Compounds

In some embodiments, the presently disclosed subject matter can utilize sulfotransferases, epimerases, glycosyltransferases, and/or heprosan synthases, among other enzymes as would be appreciated by one of ordinary skill in the art. These enzymes, and others that would be employed by one of ordinary skill in the art, are referred to herein as "the enzymes", "these enzymes", and/or "enzymes". In some embodiments the chemoenzymatic syntheses can employ NST, $C_5$-epimerase ($C_5$-epi), 2-OST, 6-OST-1, 6-OST-3, 3-OST-1, 3-OST-5, N-acetyl glucosaminyl transferase of *E. coli* K5 (KfiA), and/or heparosan synthase-2 (pmHS2). In some embodiments these and other enzymes employed in the chemoenzymatic syntheses can be expressed in *E. coli* and purified by appropriate affinity chromatography as described previously (Liu et al., 2010).

In some embodiments, one or more of the converting reactions can employ a base compound or solution as would be appreciated by one of ordinary skill in the art. Such bases can include for example lithium hydroxide or a mixture of triethylamine, $CH_3OH$, and/or $H_2O$.

In some embodiments, the chemoenzymatic syntheses employ sulfotransferases, such as O-sulfotransferases (OSTs), to sulfate polysaccharides. Sulfotransferases comprise a family of enzymes that catalyze the transfer of a sulfonate or sulfuryl group ($SO_3$) from a sulfo donor compound, i.e. an $SO_3$-donor molecule, to an acceptor molecule. By way of non-limiting example, the sulfo donor compound or $SO_3$-donor molecule can be the cofactor 3'-phosphoadenosine-5'-phosphosulfate (PAPS). Even though it is more accurate to call these sulfonation reactions, the term sulfation is still widely used. Therefore, the term "sulfation" as used herein refers to a transfer of a sulfonate or sulfuryl group from one molecule to another.

Sulfotransferases mediate sulfation of different classes of substrates such as carbohydrates, oligosaccharides, peptides, proteins, flavonoids, and steroids for a variety of biological functions including signaling and modulation of receptor binding (Bowman et al., (1999) *Chem. Biol.* 6, R9-R22; and Falany (1997) *FASEB J.* 11, 1-2). Many new sulfotransferases have been identified and cloned (Aikawa et al., (1999) *J. Biol. Chem.* 274, 2690; Dooley (1998) *Chemico-Biol. Interact.* 109, 29; Fukuta et al. (1998) *Biochim. Biophys. Act.* 1399, 57; Habuchi et al., (1998) *J. Biol. Chem.* 273, 9208; Mazany et al., (1998) *Biochim. Biophys. Act.* 1407, 92; Nastuk et al. (1998) *J. Neuroscience* 18, 7167; Ong et al., (1998) *J. Biol. Chem.* 273, 5190; Ouyang et al., (1998) *J. Biol. Chem.* 273, 24770; Saeki et al. (1998) *J. Biochem.* 124, 55; Uchimura et al. (1998) *J. Biol. Chem.* 273, 22577; and Yoshinari et al., (1998) *J. Biochem.* 123, 740).

As used herein, the term "O-sulfotransferase (OST)" includes polypeptides and nucleic acids encoding HS O-sulfotransferases, such as for example "2-OST" (e.g., mouse 2-OST, GENBANK® Accession No. AAC40135; "3-OST-1" (e.g., human 3-OST-1, GENBANK® Accession No. NP_005105; "3-OST-3" (e.g., human 3-OST-3A, GENBANK® Accession No. NP_006033 and human 3-OST-3B, GENBANK® Accession No. NP_006032; and "6-OST" (e.g., mouse 6-OST-1, GENBANK® Accession No. NP_056633, mouse 6-OST-2, GENBANK® Accession No. BAA89247, and mouse 6-OST-3, GENBANK® Accession No. NP_056635), which are HS 2-O-sulfotransferase, HS 3-O-sulfotransferase isoform 1, HS 3-O-sulfotransferase isoform 3, and HS 6-O-sulfotransferase, respectively. In some embodiments, an OST can comprise 3-OST-5.

The term "OST" includes invertebrate and vertebrate homologs of the O-sulfotransferases (e.g., mammalian (such as human and mouse), insect, and avian homologs). As such, although exemplary embodiments of particular OSTs have been disclosed herein, the presently disclosed subject matter is not intended to be limited to the disclosed examples, but rather "OST", including particular OSTs (e.g., 2-OST, 3-OST-1, 3-OST-3, and 6-OST), includes all comparable OSTs known to the skilled artisan.

In some embodiments the disclosed chemoenzymatic syntheses can employ $C_5$-epimerase ($C_5$-epi). As such, although exemplary embodiments of particular epimerases have been disclosed herein, the presently disclosed subject matter is not intended to be limited to the disclosed examples, but rather "epimerase", including $C_5$-epi, includes all comparable epimerases known to the skilled artisan. Indeed, other epimerases, or compounds having epimerase activity, can be employed without departing from the scope of the presently disclosed subject matter.

In some embodiments the disclosed chemoenzymatic syntheses can employ N-acetyl glucosaminyl transferase of *E. coli* K5 (KfiA). As such, although exemplary embodiments of particular glucosaminyl transferase have been disclosed herein, the presently disclosed subject matter is not intended to be limited to the disclosed examples, but rather "glucosaminyl transferase", including KfiA, includes all comparable glucosaminyl transferases known to the skilled artisan. Indeed, other glucosaminyl transferases, or compounds having similar transferase activity, can be employed without departing from the scope of the presently disclosed subject matter.

In some embodiments the disclosed chemoenzymatic syntheses can employ heparosan synthase-2 (pmHS2). As such, although exemplary embodiments of particular heparosan synthases have been disclosed herein, the presently disclosed subject matter is not intended to be limited to the disclosed examples, but rather "heparosan synthase", including pmHS2, includes all comparable heparosan synthases known to the skilled artisan. Indeed, other heparosan synthases, or compounds having similar synthase activity, can be employed without departing from the scope of the presently disclosed subject matter.

The terms "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" refer to peptides having amino acid sequences which are substantially identical to native amino acid sequences from the organism of interest and which are biologically active in that they comprise all or a part of the amino acid sequence of an O-sulfotransferase, epimerase, glucosaminyl transferase, or heprosan synthase, or cross-react with antibodies raised against such enzymes, or retain all or some of the biological activity of the native amino acid sequence or protein of such enzymes. Such biological activity can include immunogenicity.

The terms "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" also include analogs of the enzymes. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or Compound analogs of these enzymes. There is no need for a "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" to comprise all or substantially all of the amino acid sequence of a native enzyme gene product. Shorter or longer sequences are anticipated to be of use in the presently disclosed subject matter, shorter sequences are herein referred to as "segments." Thus, the terms "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" also include fusion or recombinant polypeptides and proteins comprising sequences of the enzyme protein. Methods of preparing such proteins are known in the art.

The terms "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" refer to any DNA sequence that is substantially identical to a polynucleotide sequence encoding an enzyme isoform gene product, protein or polypeptide as defined above, and can also comprise any combination of associated control sequences. The terms also refer to RNA, or antisense sequences, complementary to such DNA sequences. As used herein, the term "DNA segment" refers to a DNA molecule that has been isolated free of total genomic DNA of a particular species. Furthermore, a DNA segment encoding a polypeptide of one of these enzymes refers to a DNA segment that contains coding sequences for one of these enzymes, yet is isolated away from, or purified free from, total genomic DNA of a source species, such as for example *Homo sapiens*. Included within the term "DNA segment" are DNA segments and smaller fragments of such segments, and also recombinant vectors, including, for example, plasmids, cosmids, phages, viruses, and the like.

The term "substantially identical", when used to define either a gene product of one of these enzymes or amino acid sequence, or an enzyme gene or nucleic acid sequence, means that a particular sequence varies from the sequence of a natural enzyme by one or more deletions, substitutions, or additions, the net effect of which is to retain at least some of biological activity of the natural gene, gene product, or sequence. Such sequences include "mutant" sequences, or sequences in which the biological activity is altered to some degree but retains at least some of the original biological activity.

Alternatively, DNA analog sequences are "substantially identical" to specific DNA sequences disclosed herein if: (a) the DNA analog sequence is derived from coding regions of the natural enzyme gene; or (b) the DNA analog sequence is capable of hybridization of DNA sequences of (a) under stringent conditions and which encode biologically active enzyme gene products; or (c) the DNA sequences are degenerate as a result of alternative genetic code to the DNA analog sequences defined in (a) and/or (b). Substantially identical analog proteins will be equal to or greater than about 60%, 70%, 80%, 90%, 95%, 96%, 97%, 98%, or 99% identical to the corresponding sequence of the native protein. Sequences having lesser degrees of identity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

Sequence identity or percent similarity of a DNA or peptide sequence can be determined, for example, by comparing sequence information using the GAP computer program, available from the University of Wisconsin Geneticist Computer Group. The GAP program utilizes the alignment method of Needleman et al. (1970) *J Mol Biol* 48:443, as revised by Smith et al. (1981) *Adv Appl Math* 2:482. Briefly, the GAP program defines similarity as the number of aligned symbols (i.e., nucleotides or amino acids) that are similar, divided by the total number of symbols in the shorter of the two sequences. The preferred parameters for the GAP program are the default parameters, which do not impose a penalty for end gaps. See Schwartz et al. (1979) *Nuc Acids Res* 6(2):745-755; Gribskov et al. (1986) *Nuc Acids Res* 14(1):327-334.

In certain embodiments, the present subject matter concerns the use of the enzyme genes and gene products that include within their respective sequences a sequence that is essentially that of an enzyme gene, or the corresponding protein. For example, the term "a sequence essentially as that of an OST gene", means that the sequence is substantially identical or substantially similar to a portion of an OST gene and contains a minority of bases or amino acids (whether DNA or protein) which are not identical to those of an OST protein or an OST gene, or which are not a biologically functional equivalent. The terms "a sequence essentially as that of an epimerase gene", "a sequence essentially as that of a glycosyl transferase gene", and "a sequence essentially as that of a heparosan synthase gene" have similar meanings. The term "biologically functional equivalent" is well understood in the art and is further defined in detail herein. Nucleotide sequences are "essentially the same" where they have between about 75% and about 85% or more preferably, between about 86% and about 90%, or more preferably greater than 90%, or more preferably between about 91% and about 95%, or even more preferably, between about 96% and about 99%; of nucleic acid residues which are identical to the nucleotide sequence of the enzyme gene. Similarly, peptide sequences which have about 60%, 70%, 80%, or 90%, or preferably from 90-95%, or more preferably greater than 96%, or more preferably 95-98%, or most preferably 96%, 97%, 98%, or 99% amino acids which are identical or functionally equivalent or biologically functionally equivalent to the amino acids of the enzyme polypeptide will be sequences which are "essentially the same".

Gene products and encoding nucleic acid sequences for the enzymes employed in the disclosed methods, which have functionally equivalent codons, are also covered by the presently disclosed subject matter. The term "functionally equivalent codon" is used herein to refer to codons that encode the same amino acid, such as the ACG and AGU codons for serine. Applicants contemplate substitution of functionally equivalent codons of Table 1 into sequences of the enzymes disclosed herein as equivalents.

TABLE 2

Functionally Equivalent Codons

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |

TABLE 2 -continued

Functionally Equivalent Codons

| Amino Acids | | | Codons |
|---|---|---|---|
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood by those of skill in the art that amino acid and nucleic acid sequences can include additional residues, such as additional N- or C-terminal amino acids or 5' or 3' nucleic acid sequences, and yet still be encompassed by the enzymes disclosed herein, so long as the sequence retains biological protein activity where protein expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

The present subject matter also encompasses the use of nucleotide segments that are complementary to the sequences of the present subject matter, in one embodiment, segments that are fully complementary, i.e. complementary for their entire length. Nucleic acid sequences that are "complementary" are those, which are base-paired according to the standard Watson-Crick complementarity rules. As used herein, the term "complementary sequences" means nucleic acid sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

One technique in the art for assessing complementary sequences and/or isolating complementary nucleotide sequences is hybridization. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000 mM, typically less than about 500 mM, and preferably less than about 200 mM. However, the combination of parameters is much more important than the measure of any single parameter. See e.g., Wethmur & Davidson (1968) *J Mol Biol* 31:349-370. Determining appropriate hybridization conditions to identify and/or isolate sequences containing high levels of homology is well known in the art. See e.g., Sambrook et al. (2001) *Molecular Cloning: A Laboratory Manual*, Third Edition, Cold Spring Harbor Laboratory Press, Cold Spring Harbor, N.Y.

For the purposes of specifying conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another exemplary stringent hybridization scheme uses 50% formamide, 4×SSC at 42° C. Another example of "stringent conditions" refers to conditions of high stringency, for example 6×SSC, 0.2% polyvinylpyrrolidone, 0.2% Ficoll, 0.2% bovine serum albumin, 0.1% sodium dodecyl sulfate, 100 µg/ml salmon sperm DNA and 15% formamide at 68° C. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate).

Nucleic acids that are substantially identical to the provided enzymes, e.g., allelic variants, genetically altered versions of the gene, etc., bind to the disclosed OSTs under stringent hybridization conditions. By using probes, particularly labeled probes of DNA sequences, one can isolate homologous or related genes. The source of homologous genes can be any species, e.g., primate species, particularly human; rodents, such as rats and mice; canines; felines; bovines; ovines; equines; insects; yeasts; nematodes; etc.

Between mammalian species, e.g., human, mouse and rat, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nucleotides long, more usually at least about 30 nucleotides long, and can extend to the complete sequence that is being compared. Algorithms for sequence analysis are known in the art, such as BLAST, described in Altschul et al. (1990) *J Mol Biol* 215:403-410. The sequences provided herein are essential for recognizing enzymes related and homologous proteins in database searches.

At a biological level, identity is just that, i.e. the same amino acid at the same relative position in a given family member of a gene family. Homology and similarity are generally viewed as broader terms. For example, biochemically similar amino acids, for example leucine and isoleucine or glutamate/aspartate, can be present at the same position—these are not identical per se, but are biochemically "similar". As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine. When percentages are referred to herein, it is meant to refer to percent identity. The percent identities referenced herein can be generated by alignments with the program GENEWORKS™ (Oxford Molecular, Inc. of Campbell, Calif., U.S.A.) and/or the BLAST program at the NCBI website. Another commonly used alignment program is entitled CLUSTAL W and is described in Thompson et al. (1994) *Nucleic Acids Res* 22(22):4673-4680, among other places.

The term "gene" is used for simplicity to refer to a functional protein, polypeptide or peptide encoding unit. As will be understood by those in the art, this functional term includes both genomic sequences and cDNA sequences.

As noted above, modifications and changes can be made in the structure of enzyme proteins and peptides described herein and still constitute a molecule having like or otherwise desirable characteristics. For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the native protein, but this need not be the case, and the biological activity of the presently disclosed subject matter is not limited to a particular mechanism of action. It is thus contemplated in accordance with the present subject matter that various changes can be made in the sequence of the enzyme proteins and peptides or underlying nucleic acid sequence without appreciable loss of their biological utility or activity.

Biologically functional equivalent peptides, as used herein, are peptides in which certain, but not most or all, of the amino acids can be substituted. Thus, applicants contemplate substitution of codons that encode biologically equivalent amino acids as described herein into the sequences of the disclosed enzymes, but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged. Changes designed by man can be introduced through the application of site-directed mutagenesis techniques, e.g., to introduce improvements to the antigenicity of the protein or to test enzyme mutants in order to examine enzyme activity, or other activity at the molecular level.

Amino acid substitutions, such as those which might be employed in modifying enzyme proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5);

methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al. (1982) *J Mol Biol* 157:105, incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those, which are within ±1 of the original value, are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those, which are within ±1 of the original value, are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that the presently disclosed subject matter is not limited to the particular nucleic acid and amino acid sequences of the enzymes disclosed herein, including sulfotransferases, epimerases, glycosyltransferases, and/or heprosan synthases. Recombinant vectors and isolated DNA segments can therefore variously include the enzyme polypeptide-encoding region itself, include coding regions bearing selected alterations or modifications in the basic coding region, or include larger polypeptides which nevertheless comprise the enzyme polypeptide-encoding regions or can encode biologically functional equivalent proteins or peptides which have variant amino acid sequences. Biological activity of an enzyme can be determined using techniques generally known in the art, for example as disclosed herein in the Examples.

The nucleic acid segments of the present subject matter, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of the enzymes disclosed herein, such as about 10 nucleotides, and which are up to 10,000 or 5,000 base pairs in length, with segments of 3,000 being preferred in certain cases. DNA segments with total lengths of about 4,000, 3,000, 2,000, 1,000, 500, 200, 100, and about 50 base pairs in length are also contemplated to be useful.

Recombinant vectors form further aspects of the present subject matter. Particularly useful vectors are those in which the coding portion of the DNA segment is positioned under the control of a promoter. The promoter can be that naturally associated with an enzyme gene, as can be obtained by isolating the 5' non-coding sequences located upstream of the coding segment or exon, for example, using recombinant cloning and/or polymerase chain reaction (PCR) technology and/or other methods known in the art, in conjunction with the compositions disclosed herein.

In other embodiments, it is provided that certain advantages will be gained by positioning the coding DNA segment under the control of a recombinant, or heterologous, promoter. As used herein, a recombinant or heterologous promoter is a promoter that is not normally associated with an enzyme gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See, e.g., Sambrook et al. (2001) *Molecular Cloning: A Laboratory Manual*, Third Edition, Cold Spring Harbor Laboratory Press, Cold Spring Harbor, New York). The promoters employed can be constitutive or inducible and can be used under the appropriate conditions to direct high level expression of the introduced DNA segment, such as is advantageous in the large-scale production of recombinant proteins or peptides.

In some embodiments of the method disclosed herein for sulfating polysaccharides, an enzyme of the presently disclosed subject matter (e.g. sulfotransferases, epimerases, glycosyltransferases, and/or heprosan synthases) can be immobilized on a substrate. This provides an advantage in that the substrate to which the enzymes are attached can be washed after a sulfation reaction to remove all components of the reaction except the bound enzymes. As such, the products of the reaction can be more easily separated from the enzymes catalyzing the reaction and the enzymes can be recycled and utilized again in multiple sulfation reactions. In some embodiments, the substrate is agarose. In particular embodiments, the agarose substrate is an agarose bead and the enzymes are linked to the beads.

V.B. Reduction of Inhibitory Effects of PAP

The presently disclosed methods for synthesizing heparin compounds can comprise the use of a PAPS regenerating enzyme and a sulfo donor compound. The PAPS regenerating enzyme catalyzes regeneration of the PAPS from the PAP utilizing the sulfo donor compound as a substrate. See, e.g., U.S. Pat. No. 6,255,088; and Burkart et al., (2000) *J. Org. Chem.* 65, 5565-5574, both of which are herein incorporated by reference in their entirety. Thus, the PAPS regeneration system provides the dual advantages of reducing the inhibitory effects of PAP accumulation on sulfotransferase activity while also constantly "recharging" the reaction mixture with the primary sulfo donor molecule, PAPS. In some embodiments, the PAPS regenerating enzyme is an estrogen sulfotransferase.

Thus, an aspect of the presently disclosed subject matter is directed to a sulfo donor compound (e.g., PAPS) regeneration process coupled with sulfation of a polysaccharide substrate. In particular, the process can be of a type wherein the sulfation of a polysaccharide substrate is catalyzed by a sulfotransferase, such as one or more OSTs, with a conversion of 3'-phosphoadenosine-5'-phosphosulfate (PAPS) to adenosine 3',5'-diphosphate (PAP). The sulfation process can be coupled with an enzymatic regeneration of the PAPS from the PAP. The enzymatic regeneration can employ an arylsulfotransferase as the catalyst and an aryl sulfate as a substrate. In some embodiments, the enzymatic regeneration can comprise a human or mouse estrogen sulfotransferase (EST). As disclosed elsewhere herein, preferred carbohydrate substrates can include GAGs, such as for example heparan sulfates, including heparin.

Coupling the sulfotransferase catalyzed sulfation reaction with a PAPS regeneration system can provide a further advantage of generating PAPS utilized in the reaction directly from PAP. That is, the reaction mixture can be formulated to combine PAP with a PAPS regenerating enzyme prior to or simultaneously with addition of a sulfotransferase to the reaction mixture. The PAPS regenerating enzyme can then generate PAPS from the PAP for use by the sulfotransferase, thereby alleviating the need of supplying any of the more expensive and unstable PAPS to the reaction mixture. For example, coupling the PAPS regeneration system to use PNPS as a sulfo donor can potentially reduce the cost of the synthesis of sulfated polysaccharides by as much as 1,000-fold. As such, in some embodiments of the presently disclosed subject matter a method of sulfating a polysaccharide is provided comprising providing a reaction mixture comprising therein adenosine 3',5'-diphosphate (PAP), a PAPS regenerating enzyme and a sulfo donor compound (other than PAPS, e.g., PNPS) and incubating the reaction mixture for a time period sufficient to catalyze the production of 3'-phosphoadenosine 5'-phosphosulfate (PAPS) from the PAP by the PAPS regenerating enzyme utilizing the sulfo donor compound as a substrate. The method further comprises incubating a polysaccharide substrate and at least one O-sulfotransferase (OST) enzyme with the reaction mixture, wherein production of a sulfated polysaccharide from the polysaccharide substrate is catalyzed by the OST enzyme with a conversion of the PAPS to PAP and wherein the PAPS regenerating enzyme then catalyzes regeneration of the PAPS from the PAP, again utilizing the sulfo donor compound as a substrate. An Appendix is included herewith and is intended to be part of the instant disclosure.

VI. Treatment Methods

In some embodiments, provided herein are methods of treating a subject by administering one or more of the heparin compounds disclosed herein. For example, in some aspects a method of treating a subject is provided, comprising providing a subject to be treated and administering to the subject a heparin compound having anticoagulant activity. In some aspects, the heparin compound is one of the following:

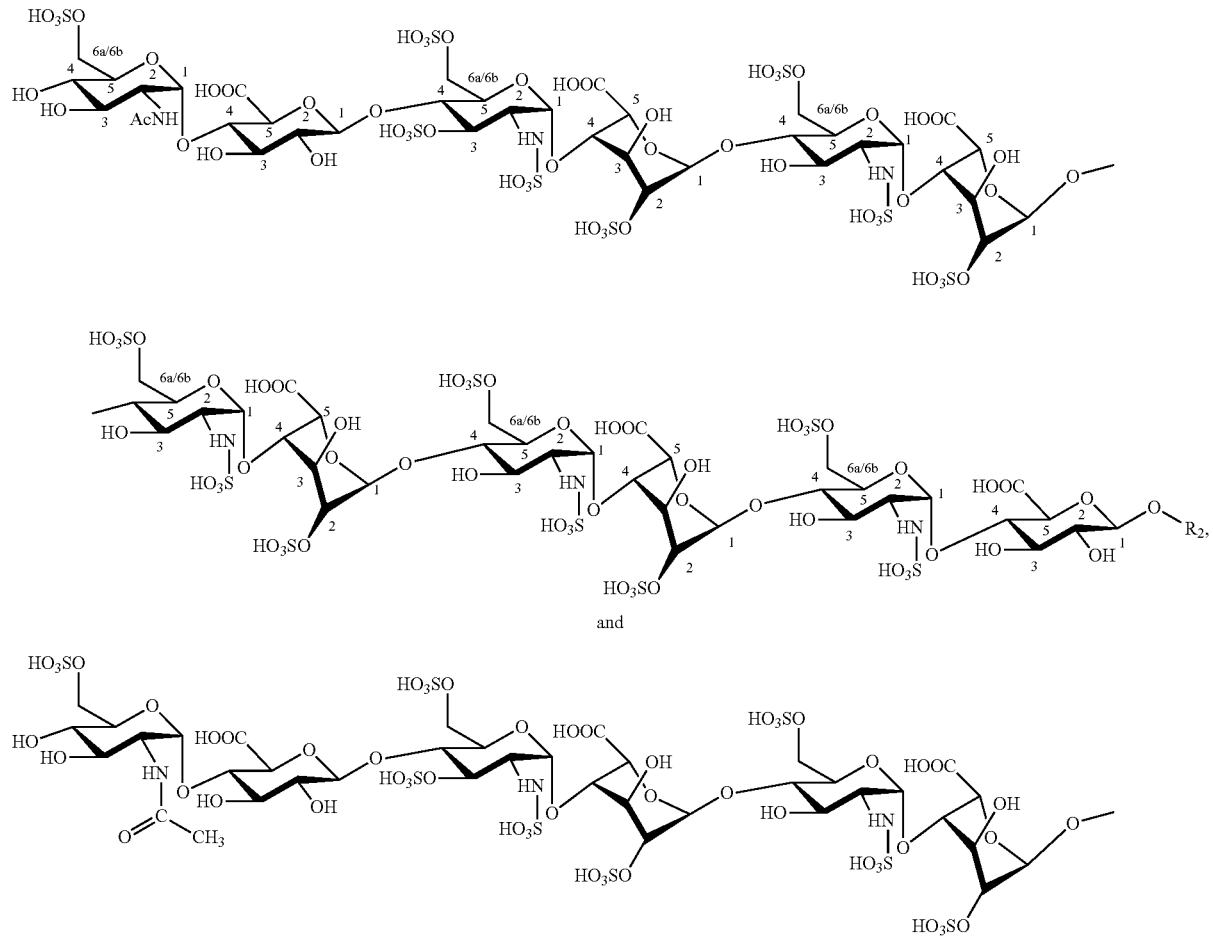

-continued

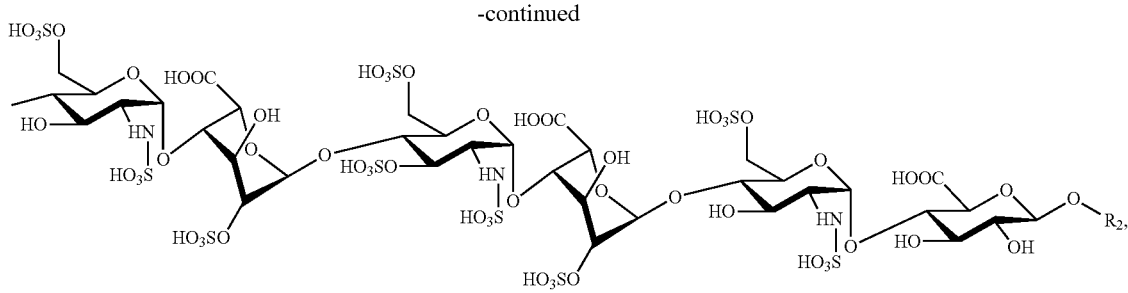

wherein $R_2$ is present or absent, and/or wherein when $R_2$ is present it comprises a detectable tag, optionally para-nitrophenyl. In some aspects, the heparin compound used in such treatments is a heparin compound comprising a synthetic, low-molecular weight heparin compound with reversible anticoagulant activity, wherein the anticoagulant activity of the heparin compound is reversible by protamine, wherein the anticoagulant activity is reversed by about 50% or more in the presence of 1 ug/ml of protamine, as disclosed herein.

In some embodiments, provided herein are methods of treating a subject in need of anticoagulant therapy. Such methods can comprise providing a subject in need of anticoagulant therapy, administering to the subject a heparin compound having anticoagulant activity, monitoring the subject for heparin-induced thrombocytopenia, and administering to the subject an antidote to reverse the anticoagulant activity of the heparin compound if the subject suffers from heparin-induced thrombocytopenia. In such methods the heparin compound can comprise for example a heparin compound comprising a structure selected from:

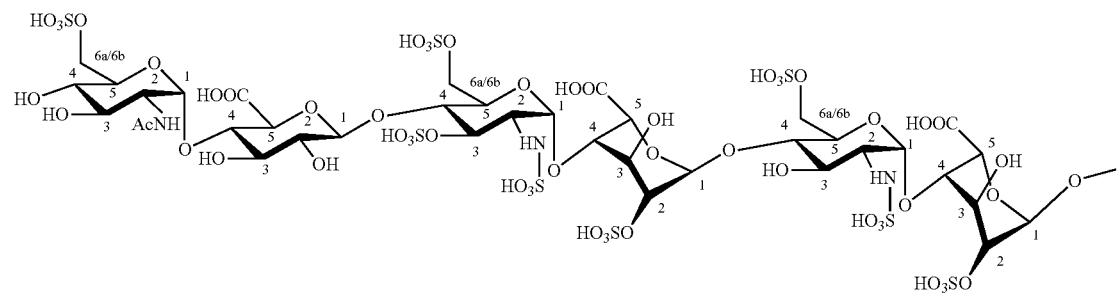

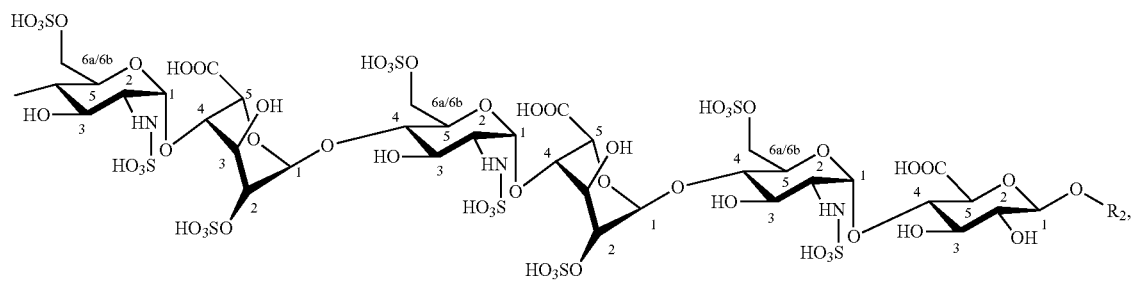

and

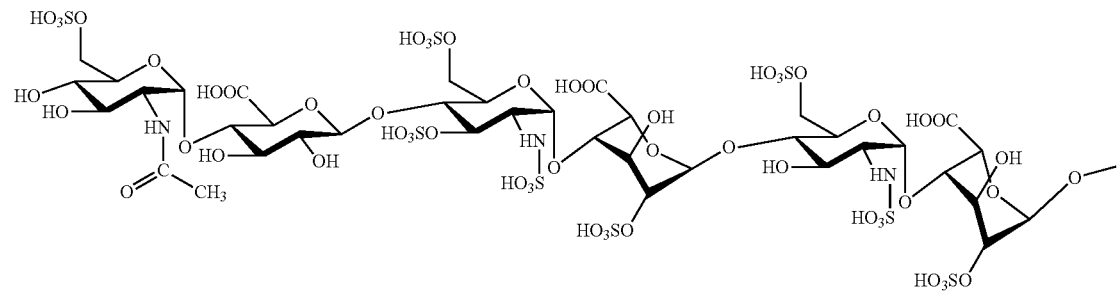

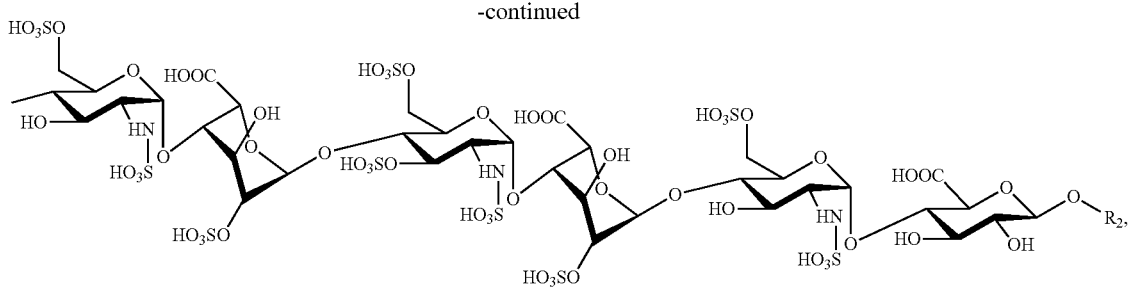

wherein R₂ is present or absent, wherein when R₂ is present it comprises a detectable tag, optionally para-nitrophenyl. In some aspects, the antidote to reverse the anticoagulant activity of the heparin compound is protamine.

In some embodiments, a subject to be treated in any of the methods of treatment disclosed herein can be a subject suffering from venous thromboembolism. In some embodiments, a subject to be treated can be a subject that is renal-impaired. In some embodiments, the subject is a human subject.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Materials and Methods for Examples 1-11

Expression of HS biosynthetic enzymes. A total of nine enzymes were used for the synthesis, including NST, $C_5$-epi, 2-OST, 6-OST-1, 6-OST-3, 3-OST-1, 3-OST-5, KfiA, and pmHS2. All enzymes were expressed in *E. coli* and purified by appropriate affinity chromatography as described previously (Liu, R. et al., *J Biol Chem* 285, 34240-34249, 2010; Xu, D., Moon, A., Song, D., Pedersen, L. C. & Liu, *J. Nat Chem Biol* 4, 200-202, 2008).

Preparation of enzyme cofactors. A sulfo donor, 3'-phosphoadenosine 5'-phosphosulfate (PAPS), was prepared from ATP and sodium sulfate using adenosine phosphokinase and ATP-sulfurylase (Zhou, X., Chandarajoti, K., Pham, T. Q., Liu, R. & Liu, J., *Glycobiology* 21, 771-780, 2011). The preparation of UDP-GlcNTFA was started from glucosamine (Sigma-Aldrich), which was first converted to GlcNTFA by reacting with S-ethyl trifluorothioacetate (Sigma-Aldrich) followed the protocol described previously (Liu, R. et al., *J Biol Chem* 285, 34240-34249, 2010). The resultant GlcNTFA was converted to GlcNTFA-1-phosphate using N-acetylhexoamine 1-kinase (Zhao, G., Guan, W., Cai, L. & Wang, P. G., *Nat. Protoc.* 5, 636-646, 2010). The plasmid expressing N-acetylhexoamine 1-kinase was a generous gift from Prof. Peng Wang (Georgia State University), and the expression of the enzyme was carried out in *E. coli* as reported (Zhao, G., Guan, W., Cai, L. & Wang, P. G., *Nat. Protoc.* 5, 636-646, 2010). The UDP-GlcNTFA synthesis was completed by transforming GlcNTFA-1-phosphate using glucosamine-1-phosphate acetyltransferase/N-acetyl-glucosamine-1-phosphate uridyltransferase (GlmU) as described (Liu, R. et al., *J Biol Chem* 285, 34240-34249, 2010). The resultant UDP-GlcNTFA was ready for the elongation reaction involved in using KfiA as described below.

Synthesis of compound 6. The conversion of a starting material GlcA-PNP to compound 6 involves seven steps, including five elongation steps, one detrifluoroacetylation/N-sulfation step and one $C_5$-epimerization/2-O-sulfation step. Elongation of GlcA-PNP (100 mg, from Sigma-Aldrich) to GlcA-GlcNTFA-GlcA-GlcNTFA-GlcA-PNP was completed in 4 steps using two bacterial glycosyl transferases, N-acetyl glucosaminyl transferase of *E. coli* K5 (KfiA) and heparosan synthase-2 (pmHS2) from *Pasteurella multocida*. To introduce a GlcNTFA residue, GlcA-pnp (1.2 mM) was incubated with KfiA (20 μgml⁻¹) in a buffer containing Tris (25 mM, pH 7.5), MnCl₂ (15 mM) and UDP-GlcNTFA (1.5 mM), at room temperature overnight. To introduce a GlcA residue, disaccharide substrate, GlcNTFA-GlcA-pnp (1.2 mM), was incubated with pmHS2 (20 μgml⁻¹) in a buffer containing Tris (25 mM, pH 7.5), MnCl₂ (15 mM) and UDP-GlcA (1.5 mM), at room temperature overnight. The product after each elongation step was purified using a $C_{18}$ column (0.75×20 cm; Biotage), which was eluted with a linear gradient of 0-100% acetonitrile in H₂O and 0.1% TFA in 60 min at a flow rate of 2 mlmin⁻¹. The eluent was monitored by the absorbance at 310 nm, and the identity of the product was confirmed by ESI-MS. The addition of GlcNTFA and GlcA residues was repeated one more time to form a pentasaccharide backbone for the subsequent N-detrifluoroacetylation/N-sulfation.

The pentasaccharide backbone was further subjected to detrifluoroacetylation, followed by N-sulfation with N-sulfotransferase (NST). The pentasaccharide backbones (280 mg) were dried and resuspended in 30 ml of 0.1 M LiOH on ice for 2 h. The degree of completion of the detrifluoroacetylation reaction was monitored by PAMN-HPLC analysis and ESI-MS. Upon the completion of detrifluoroacetylation, the pH of the reaction mixture decreased to 7.0 and incubated of MES 50 mM pH 7.0, N-sulfotransferase 10 μgml⁻¹ and 0.5 mM PAPS in 780 ml at 37° C. overnight, where the amount of PAPS was about 1.5-times molar amount of NH₂ groups in the pentasaccharide. N-sulfated product was purified by Q column, and the purified product with the structure of GlcA-GlcNS-GlcA-GlcNS-GlcA-PNP was dialyzed.

To GlcA-GlcNS-GlcA-GlcNS-GlcA-pnp pentasaccharide, another GlcNTFA was introduced using KfiA following the procedure as described above. The reaction was by PAMN-HPLC to observe a shift in retention time of the peak with the absorbance at 310 nm. The reaction mixture was incubated with MES 50 mM (pH 7.0), CaCl₂ 2 mM, 10 μgml⁻¹ $C_5$-epi, 2-OST 10 μgml⁻¹, 0.2 mM PAPS and 0.13 mM hexasaccharide substrate in 2 liter volume at 37° C. overnight. The reaction mixture was then purified by Q-Sepharose column to obtain Compound 6.

HPLC analysis. Both DEAE-HPLC and polyamine-based anion exchange (PAMN)-HPLC were used to analyze the purity of the products. The elution conditions for the HPLC analysis were described elsewhere (Liu, R. et al. *J Biol Chem* 285, 34240-34249, 2010).

Example 1

Synthesis of Compound 1, 2, 3, 4, and 5

The conversion of compound 6 to 1, compound 7 to 2 and compound 8 to 3 followed same reactions, including detrifluoroacetylation/N-sulfation, 6-O-sulfation and 3-O-sulfation by 3-OST-1 enzyme. The conversion of compound 9 to 4 involved 2 steps, including 6-O-sulfation and 3-OST-1 sulfation. The conversion of compound 4 to 5 was completed by 3-O-sulfation using 3-OST-5 enzyme. The 6-O-sulfation reaction contained 50 mM MES, pH 7.0, 1.5 mM PAPS and 0.3 mM substrate, 0.2 mgml$^{-1}$ 6-OST-1 and 0.2 mgml$^{-1}$ 6-OST-3 in 20 to 40 ml overnight at 37° C. The extent reaction was monitored by DEAE-HPLC. 3-OST-1 and 3-OST-5 sulfation reaction mixture contained 50 mM MES, pH 7.0, 10 mM MnCl$_2$, 5 mM MgCl$_2$, 0.5 mM PAPS, 0.25 mM substrate, 10 ugml$^{-1}$ 3-OST-1 or 10 ugml$^{-1}$ 3-OST-5 for overnight at 37° C. The extent reaction was also monitored by DEAE-HPLC. The products were purified by Q-Sepharose column.

Example 2

Purification of Intermediate and LMWH Compounds by Q-Sepharose

Purification of Compounds 6, 7, 8, and 9 as well as all the other earlier intermediate was conducted by a fast flow Q-Sepharose column (15×200 mm; GE Health Care, Wauwatosa, Wis., United States of America), which was eluted with a linear gradient of 20-100% 1M NaCl in 20 mM NaOAc at pH 5.0 in 2 h at a flow rate of 2 mlmin$^{-1}$. Purification of those highly sulfated oligosaccharides, i.e. LMWH Compounds 1-5, was carried out by a Q-Sepharose column, which was eluted with a linear gradient of 30-100% 2M NaCl in 20 mM NaOAc at pH 5.0 in 2 h at a flow rate of 2 mlmin$^{-1}$.

Determination of the in vitro and ex vivo anti-Xa activity. Assays were based on a previously published method (Zhang, L. et al., *J. Biol. Chem.* 276, 42311-42321, 2001; Duncan et al., *Biochim Biophys Acta* 1671, 34-43, 2004). Briefly, human factor Xa (Enzyme Research Laboratories, South Bend, Ind., United States of America) was diluted to 50 Uml$^{-1}$ with PBS. The chromogenic substrates, S-2765 was from Diapharma (Westchester, Ohio, United States of America) and made up at 1 mgml$^{-1}$ in water. UFH (from US Pharmacopea), LOVENOX® (from local pharmacy) and LMWH Compounds 1 to 5) was dissolved in PBS at various concentrations (3 to 600 μgml$^{-1}$). The reaction mixture, which consisted of 20 μl of human plasma (Sigma-Aldrich, St. Louis, Mo., United States of America) and 8 μl of the solution containing the sample, was incubated at room temperature for 5 min. Factor Xa (100 μl) was then added. After incubating at room temperature for 4 min, 30 μl of S-2765 substrate was added. The absorbance of the reaction mixture was measured at 405 nm continuously for 5 min. The absorbance values were plotted against the reaction time. The initial reaction rates as a function of concentration were used to calculate the IC$_{50}$ values.

Example 3

Preparation of 35S-Labeled LMWHS

UFH (from US Pharmacopea) and LOVENOX® (from local pharmacy) were modified by N-sulfotransferase. Reaction consisted of MES 50 mM pH 7.0, N-sulfotransferase 0.1 mgml$^{-1}$ and 0.5 nmol [$^{35}$S]PAPS (specificity activity of [$^{35}$S]PAPS was 2.2×10$^4$ cpm/pmol), UFH or LOVENOX® 50 μg in total 500 μl at 37° C. overnight. The products were purified by a DEAE-column. $^{35}$S-labeled LMWH Compounds 1 to 4 were prepared from the LMWH Compounds intermediates without 3-O-sulfo groups. Reaction consisted of MES 50 mM pH 7.0, 10 mM MnCl$_2$, 5 mM MgCl$_2$, 3-OST-1 0.1 mgml$^{-1}$ and 0.5 nmol [$^{35}$S]PAPS (specific activity of [$^{35}$S]PAPS was 2.2×10$^4$ cpm/pmol), oligosaccharide 5 μg in total 500 μl at 37° C. overnight. $^{35}$S-labeled LMWH Compounds 5 was prepared from LMWH Compounds 4. Reaction consisted of MES 50 mM pH 7.0, 10 mM MnCl$_2$, 5 mM MgCl$_2$, 3-OST-5 0.1 mgml$^{-1}$ and 0.5 nmol [$^{35}$S] PAPS (specific activity of [$^{35}$S]PAPS was 2.2× 10$^4$ cpm/pmol), oligosaccharide 5 μg in total 500 μl at 37° C. overnight. The $^{35}$S-labeled compound 5 was purified by a DEAE-HPLC column.

Example 4

Determination of the Binding Affinity of LMWHs to Antithrombin (AT)

The dissociation constant (K$_d$) of each sample and AT was determined using affinity co-electrophoresis (Lee, M. K. & Lander, A. D., *Proc. Natl. Acad. Sci. USA* 88, 2768-2772, 1991). Approximately 1500-2500 cpm of $^{35}$S-labeled LMWH Compounds 1 to 5 was loaded per lane with zones of AT at concentrations 0, 8, 16, 32, 60, 120, 250, 500 and 1000 nM. The gel was performed at 300 mA for 2 h, dried and analyzed on a PhosphoImager (Amersham Biosciences, Wauwatosa, Wis., United States of America Storm 860). The retardation coefficient was calculated at R=(M$_0$–M)/M$_0$, where M$_0$ is the mobility of the polysaccharide through the zone without AT, and M is the mobility of the sample through each separation zone. The retardation coefficient was then plotted against the retardation coefficient divided by its respective concentration of AT. The slope of the line represents –1/K$_d$.

Example 5

Neutralization of LMWHS by Protamine In Vitro

The procedures followed a previous publication (Sundaram, M. et al., *Proc. Natl. Acad. Sci.* 100, 651-656, 2003). The LMWH Compounds and protamine chloride (Sigma-Aldrich) were dissolved in PBS. The concentrations of the LMWH samples for each Compound were different because each Compound has different IC$_{50}$ value for the anti-Xa activity. The reaction mixture consisted of 20 μl of human plasma (Sigma-Aldrich), 2 μl of the stock solution of LMWHs (400×IC$_{50}$ of its anti-Xa activity) and 8 μl of protamine with various concentrations (from 0-90 μg/ml), and was incubated at room temperature for 5 min. The mixture (30 μl) was then subjected to anti-Xa activity measurement as described above.

Example 6

Neutralization of LMWHs by Protamine in Mice

The study was performed on eight week old male C57BL/6J mice (Jackson Laboratories, Bar Harbor, Me., United States of America) (n=4 per group). The mouse experiments were approved by the UNC Animal Care and Use Committees and complied with National Institutes of Health guidelines. Under isoflurane anesthesia, mice were subcutaneously administered with PBS, UFH (3 mgkg$^{-1}$), LOVENOX® (3 mgkg$^{-1}$) or Compound 5 (0.6 mgkg$^{-1}$) 30 min prior to a protamine administration. Protamine (15 mgkg$^{-1}$) or phosphate buffer saline (PBS) was administered intravenously via retro-orbital plexus injection, and 5 min later blood samples were drawn from the inferior vena cava into syringes preloaded with 3.2% solution of sodium citrate (final volume ratio 9:1). To obtain mouse plasma, blood samples were centrifuged at 4,000 g for 15 min at 4° C. Mouse plasma was then used to determine anti-Xa activity. Ex vivo analysis of anti-Xa activity was done similar to the in vitro study described above. Briefly, plasma (10 μl) from different groups of mice was incubated with 80 nM human factor Xa (10 μl) at room temperature for 4 minutes and S-2765 (1 mgml$^{-1}$, 30 μl) was then added. The anti-Xa activity in the mouse plasma from the PBS injected mice was defined as 100%. Statistical analysis for multiple comparisons was performed by two-way ANOVA with Bonferroni's post-hoc test (GraphPad Prism Software, La Jolla, Calif., United States of America).

Example 7

Mouse Model of Tail Bleeding

Under isoflurane anesthesia, mice (n=8 per group) were administered with PBS or Compound 5 (0.6 mgkg$^{-1}$) subcutaneously, 30 min later PBS or protamine (15 mgkg$^{-1}$) was administered via retro-orbital intravenous injection. After 5 minutes the distal part of the tail was transected at the constant diameter (1.5 mm), approximately 3-4 mm from the end. That results in both arterial and venous bleeding. The tail was immediately placed in 15 ml falcon tube containing 13 ml of pre-warm PBS (37° C.) and blood loss was observed for 30 min. The primary bleeding time was defined as the time to the first cessation of bleeding. Subsequently, time for each reinitiated bleeding was also recorded, and used to calculate total bleeding time. One mouse in Compound 5/protamine group received an inaccurate protamine injection and was excluded from the study. The blood collected in PBS was used to calculate total blood volume loss. Formic acid was added to samples (70:30 ratio) and absorbance was measured at 405 nm. A standard curve was generated by mixing 13 ml of PBS with known amounts of blood. Statistical analysis between each group was performed by one-way ANOVA (GraphPad Prism Software, La Jolla, Calif., United States of America) followed by Bonferroni's multiple comparison test.

Example 8

MS Analysis

The low-resolution analyses were performed at a Thermo LCQ-Deca. LMWH Compounds and intermediates were directly diluted in 200 μl of 9:1 MeOH/H$_2$O. A syringe pump (Harvard Apparatus, Holliston, Mass., United States of America) was used to introduce the sample by direct infusion (35 μlmin$^{-1}$). Experiments were carried out in negative ionization mode with the electrospray source set to 5 KV and 275° C. Sulfated oligosaccharide (1 μl) was diluted in a different working solution containing 200 μl of 70% acetonitrile and 10 mM imidazole. Experiments for sulfated oligosaccharides were carried out in negative ionization mode with the electrospray source set to 2 KV and 200° C. The automatic gain control was set to 1×10$^7$ for full scan MS. The MS data were acquired and processed using Xcalibur 1.3.

High resolution ESI-MS analysis was conducted on Thermo LTQ XL Orbitrap (Breman, Germany) under the following conditions. A Luna hydrophilic liquid interaction chromatography (HILIC) column (2.0×150 mm$^2$, 200 Å, Phenomenex, Torrance, Calif., United States of America) was used to separate the oligosaccharide mixture. Mobile phase A was 5 mM ammonium acetate prepared with high performance liquid chromatography (HPLC) grade water. Mobile B was 5 mM ammonium acetate prepared in 98% HPLC grade acetonitrile with 2% of HPLC grade water. After injection of 8.0 μL oligosaccharide mixture (1.0 μgμL$^-$$_1$) through an Agilent 1200 autosampler, HPLC binary pump was used to deliver the gradient from 10% A to 35% A over 40 min at a flow rate of 150 μLmin$^{-1}$. The LC column was directly connected online to the standard electrospray ionization source of LTQ-Orbitrap XL Fourier transform (FT) mass spectrometer (MS) (Thermo Fisher Scientific, San-Jose, Calif., United States of America). The source parameters for FT-MS detection were optimized using Arixtra® (purchased at a pharmacy) to minimize the insource fragmentation and sulfate loss and maximize the signal/noise in the negative-ion mode. The optimized parameters, used to prevent in-source fragmentation, included a spray voltage of 4.2 kV, a capillary voltage of −40 V, a tube lens voltage of −50 V, a capillary temperature of 275° C., a sheath flow rate of 30, and an auxiliary gas flow rate of 6. External calibration of mass spectra routinely produced a mass accuracy of better than 3 ppm. All FT mass spectra were acquired at a resolution 60,000 with 300-2000 Da mass range.

Example 9

NMR Analysis

LMWH Compounds and intermediates were analyzed by 1D $^1$H-NMR and 2D NMR ($^1$H-$^1$H COSY, $^1$H-$^{13}$C HMQC). All NMR experiments were performed at 298 K on Bruker Avance II 800 MHz spectrometer with Topsin 2.1 software. Samples (3.0 to 6.0 mg) were each dissolved in 0.5 ml D$_2$O (99.996%, Sigma-Aldrich) and lyophilized three times to remove the exchangeable protons. The samples were re-dissolved in 0.4 ml D$_2$O and transferred to NMR microtubes (OD 5 mm, Norrell NMR tubes from Sigma Aldrich). 1D $^1$H NMR experiments were performed with 256 scans and an acquisition time of 850 msec. 2D $^1$H-$^1$H COSY experiments were performed with 16 scans, 1.5 sec relaxation delay, and 500 millisecond acquisition time. 2D $^1$H-$^{13}$C HMQC experiments were performed with 16 scans, 1.5 sec relaxation delay, and 250 millisecond acquisition time.

The LMWH Compounds and intermediates were also analyzed by 1D $^1$H-NMR, 1D $^{13}$C-NMR and 2D NMR ($^1$H-$^1$H COSY, $^1$H-$^{13}$C HSQC) on Varian Inova 500 MHz spectrometer with VnmrJ 2.2D software. Samples (2.0 to 5.0 mg) were dissolved in 0.5 ml D$_2$O (99.994%, Sigma-Aldrich) and lyophilized three times to remove the exchangeable protons. The samples were re-dissolved in 0.5 ml $D_2O$ and transferred to NMR microtubes (OD 5 mm, Norrell). 1D $^1$H-NMR experiments were performed with 256 scans and an acquisition time of 768 msec. 1D $^{13}$C-NMR experiments were performed with 40,000 scans, 1.0 sec relaxation delay, and an acquisition time of 1,000 msec. 2D $^1$H-$^1$H COSY experiments were performed with 48 scans, 1.8 sec relaxation delay, and 204 msec acquisition time. 2D $^1$H-$^{13}$C HSQC experiments were performed with 48 scans, 1.5 sec relaxation delay, and 256 msec acquisition time.

Example 10

Determination of the Binding of LMWHs to Stabilin-2

The Stabilin-2 cell line expressing the 190-HARE (Harris et al., *J. Biol. Chem.* 279, 36201-36209, 2004) was grown to 90% confluency with DMEM+8% FBS+50 µgml$^{-1}$ Hygromycin B in 24-well plates for at least 2 days prior to the experiment in a standard tissue culture incubator. Endocytosis medium (DMEM+0.05% BSA) containing a known amount of $^{35}$S-labeled LMWH Compound, LOVENOX®, or UFH was added to each well in triplicate and allowed to incubate with the cells for 3 h at 37° C., 5% $CO_2$. Receptor specific internalization was assessed by incubating each radiolabeled ligand with at least a 100-fold excess of unlabeled UFH. The cells were then washed with Hank's Balanced Salt Solution (1.26 mM $CaCl_2$, 5.33 mM KCl, 0.44 mM $KH_2PO_4$, 0.5 mM $MgCl_2$-$6H_2O$, 0.41 mM $MgSO_4$-$7H_2O$, 138 mM NaCl, 4.0 mM $NaHCO_3$, 0.3 $Na_2HPO_4$, 0.3 mM phenol red, pH 7.2) three-times, and cells were lysed in 0.4 ml 0.3 N NaOH. 0.35 ml of the cell lysate mixture was mixed with 4 ml scintillation fluid (Perkin Elmer, Waltham, Mass., United States of America) and radioactivity was measured by a Beckman Coulter LS6500 scintillation counter. The remaining 0.05 ml cell lysate was used to determine protein levels using the Bradford reagent (Sigma-Aldrich). The data was calculated as the percentage of specific CPM internalized of the total amount added per µg cell lysate protein±standard deviation.

Example 11

Determination of the Clearance of LMWHs In Vivo

The mouse experiment was approved by the University of Nebraska Animal Care and Use Committees. Five to six week old BALB/c mice (Harlan Laboratories, Indianapolis, Ind., United States of America) weighing 18-20 g were anesthetized in a small 34° C. chamber with a flow of oxygen containing 4% isoflurane. Once the mice were unconscious, they were individually placed on a heated pad with a nose cone fitted over their snout with a constant flow of oxygen containing 2% isoflurane. A specific amount of $^{35}$S-labeled LMWH Compound, LMWH, or UFH was injected via the lateral tail vein using a 27G1/2 needle mounted on a 1 ml syringe. The labeled material was allowed to circulate in the blood for 12 min while the mouse lay unconscious. The abdominal cavity was exposed by incision and the liver was collected, washed, and weighed. Approximately 100 mg from each of the lobes was homogenized in 0.75 ml 1% NP-40 and then centrifuged at 12,000×g for 2 min to pellet insoluble material. The supernatant was then added to 4 ml scintillation fluid, mixed for 30 min by rocking and then radioactivity was assessed by a Beckman Coulter LS6500 scintillation counter. The data is presented as the percentage of CPM in total liver divided by total CPM injected±standard error of 3-5 mice per ligand.

REFERENCES

The references listed below as well as all references cited in the specification are incorporated herein by reference to the extent that they supplement, explain, provide a background for or teach methodology, techniques and/or compositions employed herein.

Aikawa et al., (1999) *J. Biol. Chem.* 274, 2690.
Aikawa, J.-I., et al., (2001) *J. Biol. Chem.* 276, 5876-5882.
Alexander, C. M., et al., (2000) *Nat. Genet.* 25, 329-332.
Altschul et al. (1990) *J Mol Biol* 215, 403-410.
Atha, D. H., et al., (1985) *Biochemistry* 24, 6723-6729.
Avci, F. Y., et al., (2003) *Curr. Pharm. Des.* 9, 2323-2335.
Balagurunathan, K., et al., (2003) *J. Biol. Chem.* 278, 52613-52621.
Balagurunathan, K., et al., (2003) *Nat. Biotechnol.* 21, 1343-1346.
Bernfield, M., et al., (1999) *Annu. Rev. Biochem.* 68, 729-777.
Bjornsson, S. (1993) *Anal. Biochem.* 210, 282-291.
Bowman et al., (1999) *Chem. Biol.* 6, R9-R22.
Burkart, M. D., et al., (2000) *J. Org. Chem.* 65, 5565-5574.
Capila, I., and Linhardt, R. J. (2002) *Angew. Chem. Int. Ed.* 41, 390-412.
Carfi, A., et al., (2001) *Mol. Cell* 8:169-179.
Chen et al., (1992) *Protein Expression Purif.* 3, 421-6.
Chen, J., et al., (2003) *Glycobiology* 13, 785-794.
Chen et al., (2005) *J. Biol. Chem.* 280, 42817-42825.
Conrad, H. (1998) *Heparin-binding Proteins*, Academic Press, San Diego, Calif.
Copeland et al., (2008) *Biochemistry* 47: 5774-5783.
Das et al. (2001) *Chemistry* 7, 4821-4834.
Dementiev, A., et al., (2004) *Nat. Struct. Biol.* 11, 867-863.
Dooley (1998) *Chemico-Biol. Interact.* 109, 29.
Duncan, M. B., et al., (2004) *Biochim. Biophys. Acta* 1671, 34-43.
Edavettal, S. C., et al., (2004) *J. Biol. Chem.* 279, 25789-25797.
Esko, J. D., and Lindahl, U. (2001) *J. Clin. Invest.* 108:169-173.
Esko, J. D., and Selleck, S. B. (2002) *Annu. Rev. Biochem.* 71, 435-471.
Falany (1997) *FASEB J.* 11, 1-2.
Feyerabend et al. (2006) *Nat. Chem. Biol.* 2, 195-196.
Fukuta et al. (1998) *Biochim. Biophys. Act.* 1399, 57.
Fuster et al. (2005) *Nat. Rev. Cancer* 5, 526-542.
Gama et al. (2006) *Nat. Chem. Biol.* 2, 467-473.
Gribskov et al. (1986) *Nuc Acids Res* 14(1), 327-334.
Guo et al. (1994) *Chem.-Biol. Interact.* 92, 25-31.
Habuchi et al., (1998) *J. Biol. Chem.* 273, 9208.
Habuchi, H., et al., (2000) *J. Biol. Chem.* 275, 2859-2868.
Harris, E. N. et al., *J. Biol. Chem.* 279, 36201-36209 (2004).
Kakuta et al. (2003) *Biochem. Soc. Trans.* 31 (pt2), 331-334.
Kreuger et al. (2006) *J. Cell Biol.* 174, 323-327.
Krummenacher, C., et al., (1999) *J. Virol.* 73, 8127-8137.
Kuberan, B., et al., (2003) *J. Am. Chem. Soc.* 125, 12424-12425.
Kyte et al. (1982) *J Mol Biol* 157, 105.
Lee, M. K., and Lander, A. D., (1991) *Proc. Natl. Acad. Sci. USA* 88, 2768-2772.
Li et al. (1997) *J. Biol. Chem.* 272, 28158-28163
Lin et al. (1995) *J. Am. Chem. Soc.* 117, 8031.
Lin et al. (1998) *Anal. Biochem.* 264, 111-117.
Lindahl, U., et al., (1998) *J. Biol. Chem.* 273, 24979-24982.

Lindahl, U. et al., (2005) *J. Med. Chem.* 48, 349-352.
Linhardt, R. J. (2003) *J. Med. Chem.* 46, 2551-2564.
Liu, J., and Thorp, S. C. (2002) *Med. Res. Rev.* 22, 1-25.
Liu, J., et al., (1996) *J. Biol. Chem.* 271, 27072-27082.
Liu, J., et al., (1999) *J. Biol. Chem.* 274, 38155-38162.
Liu, J., et al., (1999) *J. Biol. Chem.* 274, 5185-5192.
Liu, J., et al., (1999) *J. Biol. Chem.* 274, 5185-5192.
Liu, J., et al., (1999) *J. Biol. Chem.* 274, 38155-38162.
Liu, J., et al., (2002) *J. Biol. Chem.* 277, 33456-33467.
Liu, R. et al. *J Biol Chem* 285, 34240-34249 (2010).
Liu et al. (2007) *Appl. Microbiol. Biotechnol.* 74, 263-272.
Marcus et al. (1980) *Aial. Biochem.* 107, 296.
Marshall et al., (1997) *J. Biol. Chem.* 272, 9153-9160.
Marshall et al., (1998) *Chem.-Biol. Interact.* 109, 107-116.
Mazany et al., (1998) *Biochim. Biophys. Act.* 1407, 92.
Moon, A., et al., (2004) *J. Biol. Chem.* 279, 45185-45193.
Muñoz et al. (2006) *Biochemistry* 45, 5122-5128.
Muñoz et al. (2006) *Biochem. Biophys. Res. Commun.* 339, 597-602
Nastuk et al. (1998) *J. Neuroscience* 18, 7167.
Needleman et al. (1970) *J Mol Biol* 48, 443.
Ong et al., (1998) *J. Biol. Chem.* 273, 5190.
Ornitz, D. M., et al., (1996) *J. Biol. Chem.* 271, 15292-15297.
Ouyang et al., (1998) *J. Biol. Chem.* 273, 24770.
Ozawa et al., (1990) *Nucleic Acids Res.* 18, 4001z.
Pempe et al., (2012) *J. Biol. Chem.* 287, 20774-20783.
Petitou, M., et al., (1999) *Nature* 398, 417-422.
Petitou, M., and van Boeckel, C. A. A. (2004) *Angew. Chem. Int. Ed.* 43, 3118-3133.
Reizes, O., et al., (2001) *Cell* 106:105-116.
Rosenberg, R. D., et al., (1997) *J. Clin. Invest.* 99, 2062-2070.
Saeki et al. (1998) *J. Biochem.* 124, 55.
Sambrook et al. (2001) *Molecular Cloning: A Laboratory Manual*, Third Edition, Cold Spring Harbor Laboratory Press, Cold Spring Harbor, New York.
Sasisekharan, R., et al., (2002) *Nat. Rev. Cancer* 2, 521-528.
Schwartz et al. (1979) *Nuc Acids Res* 6(2), 745-755.
Shively, J. E., and Conrad, H. E. (1976) *Biochemistry* 15, 3932-3942.
Shriver et al. (2004) *Nat. Rev. Drug Discov.* 863-873.
Shukla, D., et al. (1999) *Cell* 99, 13-22.
Shukla, D., and Spear, P. G. (2001) *J. Clin. Invest.* 108, 503-510.
Shworak, N. W., et al., (1997) *J. Biol. Chem.* 272, 28008-28019.
Smith et al. (1981) *Adv Appl Math* 2, 482.
Sundaram, M. et al., *Proc. Natl. Acad. Sci.* 100, 651-656 (2003)
Thompson et al. (1994) *Nucleic Acids Res* 22(22), 4673-4680.
U.S. Pat. No. 6,255,088.
U.S. Pat. No. 4,554,101.
Uchimura et al. (1998) *J. Biol. Chem.* 273, 22577.
Vann et al., (1981) *Eur. J. Biochem.* 116, 359-364.
Wethmur & Davidson (1968) *J Mol Biol* 31, 349-370.
Willis, S. H., et al., (1998) *J. Virol.* 72, 5938-5947.
WuDunn, D., and Spear, P. G. (1989) *J. Virol.* 63, 52-58.
Xu, D. et al., *Nat Chem Biol* 4, 200-202 (2008).
Xu, Y. et al. *Science* 334, 498-501 (2011).
Xu, Y. et. al., *Nat Chem Biol* 4, 248-252 (2014).
Yang et al. (1996) *Protein Expression Purif.* 8, 423-429.
Yang et al. (1997) *Protein Eng.* 10, 70.
Yang et al., (1998) *Chem.-Biol. Interact.* 109, 129-135.
Yoshinari et al., (1998) *J. Biochem.* 123, 740.
Zhang, L., et al., (2001) *J. Biol. Chem.* 276, 42311-42321.
Zhang, L., et al., (2001) *J. Biol. Chem.* 276, 28806-28813.
Zhao, G., et al., *Glycobiology* 21, 771-780 (2011)

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of synthesizing a heparin compound, comprising: providing a monosaccharide substrate;
elongating the monosaccharide substrate to a hexasaccharide using enzymes N-acetyl glucosaminyl transferase and heparosan synthase-2, and substrates glucuronic acid (GlcUA) and N-trifluoroacetyl glucosamine (GlcNTFA);
converting N-trifluoroacetyl glucosamine (GlcNTFA) residue(s) on the hexasaccharide to N-sulfo glucosamine (GlcNS) residues using N-sulfotransferase (NST), 3'-phosphoadenosine 5'-phosphosulfate (PAPS), and a base to provide an N-sulfated hexasaccharide substrate;
epimerizing the N-sulfated hexasaccharide substrate using $C_5$-epimerase ($C_5$-epi); sulfating the resultant epimerized hexasaccharide using 2-O-sulfotransferase (2-OST) and 3'-phosphoadenosine 5'-phosphosulfate (PAPS) to provide the following hexasaccharide substrate:

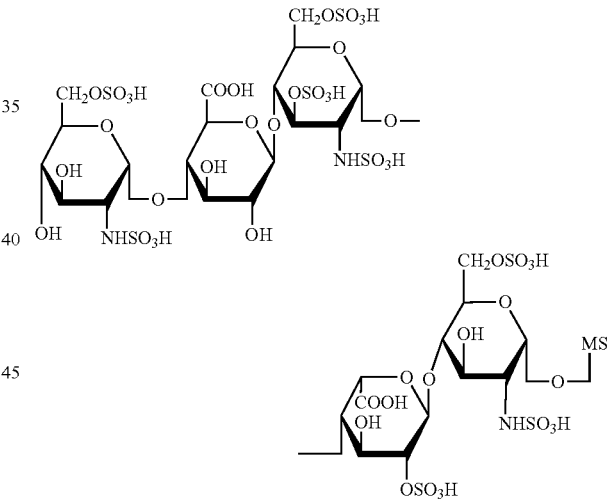

wherein MS is a monosaccharide;
elongating the hexasaccharide substrate to a heptasaccharide using heparosan synthase-2 and glucuronic acid (GlcUA);
elongating the heptasaccharide to an octasaccharide using N-acetyl glucosaminyl transferase and-N-trifluoroacetyl glucosamine (GlcNTFA); epimerizing the resultant octasaccharide using $C_5$-epimerase ($C_5$-epi); sulfating the resultant epimerized octasaccharide using 2-O-sulfotransferase (2-OST) and 3'-phosphoadenosine 5'-phosphosulfate (PAPS);
converting N-trifluoroacetyl glucosamine (GlcNTFA) residue(s) to N-sulfo glucosamine (GlcNS) residues using N-sulfotransferase (NST), 3'-phosphoadenosine 5'-phosphosulfate (PAPS), and a base to produce an octasaccharide substrate;

elongating the octasaccharide substrate to a decasaccharide using in the following order:
(1) heparosan synthase-2 and glucuronic acid (GlcUA); and
(2) N-acetyl glucosaminyl transferase and N-trifluoroacetyl glucosamine (GlcNTFA);
epimerizing the decasaccharide using $C_5$-epimerase ($C_5$-epi); sulfating the resultant epimerized decasaccharide using 2-O-sulfotransferase (2-OST) and 3'-phosphoadenosine 5'-phosphosulfate (PAPS);
converting N-trifluoroacetyl glucosamine (GlcNTFA) residue(s)on the resultant sulfated decasaccharide to N-sulfo glucosamine (GlcNS) residues using N-sulfotransferase (NST), 3'-phosphoadenosine 5'-phosphosulfate (PAPS), and a base to produce a decasaccharide substrate;
elongating the decasaccharide substrate to a dodecasaccharide using in the following order:
1) heparosan synthase-2 and glucuronic acid (GlcUA); and
(2) N-acetyl glucosaminyl transferase and N-trifluoroacetyl glucosamine (GlcNTFA) or N-acetylglucosamine (NAcGlc);
epimerizing the dodecasaccharide using $C_5$-epimerase ($C_5$-epi); sulfating the epimerized dodecasaccharide by the following reactions:
(1) using 2-O-sulfotransferase (2-OST) and 3'-phosphoadenosine 5'-phosphosulfate (PAPS);
(2) using a 6-O-sulfotransferase (6-OST) and 3'-phosphoadenosine 5'-phosphosulfate (PAPS); and
(3) using a 3-O-sulfotransferase (3-OST) and 3'-phosphoadenosine 5'-phosphosulfate (PAPS);
wherein a heparin compound is synthesized.

2. The method of claim 1, wherein the base is lithium hydroxide.

3. The method of claim 1, wherein the 6-O-sulfotransferase (6-OST) is 6-O-sulfotransferase 1 and/or 3 (6-OST-1and/or 6-OST-3).

4. The method of claim 1, wherein the 3-OST is 3-O-sulfotransferase-5 (3-OST-5).

5. The method of claim 1, wherein the glycosyl transferase is selected from the group consisting of N-acetyl glucosaminyl transferase of *E. coli* K5 (KfiA) and/or heparosan synthase-2 (pmHS2) from *Pasteurella multocida*.

6. A method of synthesizing a heparin compound, comprising: providing a hexasaccharide represented by the following structure:

wherein $R_2$ is H or a detectable tag,
elongating the hexasaccharide to a heptasaccharide using heparosan synthase-2 and glucuronic acid (GlcUA);
elongating the heptasaccharide to an octasaccharide using N-acetyl glucosaminyl transferase and N-trifluoroacetyl glucosamine (GlcNTFA);
epimerizing the octasaccharide using $C_5$-epimerase ($C_5$-epi); sulfating the resultant epimerized octasaccharide using 2-O-sulfotransferase (2-OST) and 3'-phosphoadenosine 5'-phosphosulfate (PAPS);
converting N-trifluoroacetyl glucosamine (GlcNTFA) residue(s) on the resultant sulfated octasaccharide to N-sulfo glucosamine (GlcNS) residues using N-sulfotransferase (NST), 3'-phosphoadenosine 5'-phosphosulfate (PAPS), and a base to provide an octasaccharide substrate;
elongating the octasaccharide substrate to a decasaccharide using heparosan synthase-2 and N-acetyl glucosaminyl transferase and substrates glucuronic acid (GlcUA) and N-trifluoroacetyl glucosamine (GlcNTFA);
epimerizing the decasaccharide using $C_5$-epimerase ($C_5$-epi); sulfating the resultant epimerized decasaccharide using 2-O-sulfotransferase (2-OST) and 3'-phosphoadenosine 5'-phosphosulfate (PAPS);
converting N-trifluoroacetyl glucosamine (GlcNTFA) residue(s) on the resultant sulfated decasaccharide to N-sulfo glucosamine (GlcNS) residues using N-sulfotransferase (NST), 3'-phosphoadenosine 5'-phosphosulfate (PAPS), and a base to provide a decasaccharide substrate;
elongating the decasaccharide substrate to a dodecasaccharide using heparosan synthase-2 and N-acetyl glucosaminyl transferase and substrates glucuronic acid (GlcUA) and N-acetyl glucosamine (NAcGlc);
epimerizing the dodecasaccharide using $C_5$-epimerase ($C_5$-epi); sulfating the resultant epimerized dodecasaccharide using:
(1) 2-O-sulfotransferase (2-OST) and 3'-phosphoadenosine 5'-phosphosulfate PAPS);
(2) 6-O-sulfotransferase 1 and/or 3 (6-OST-1 and/or 6-OST-3), and 3'-phosphoadenosine 5'-phosphosulfate (PAPS); and
(3) 3-O-sulfotransferase 1 (3-OST-1), and 3'-phosphoadenosine 5'-phosphosulfate (PAPS);
wherein a heparin compound represented by the following structure is synthesized:

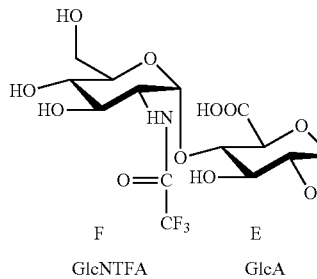
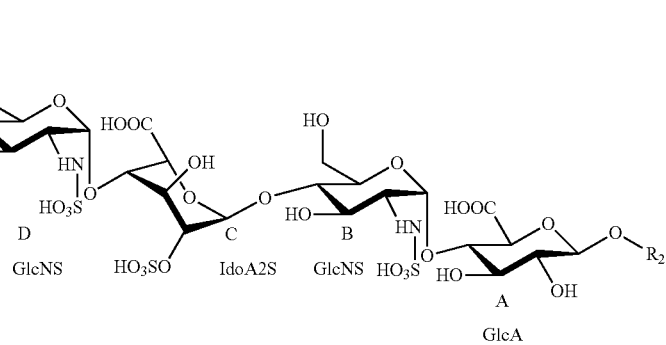

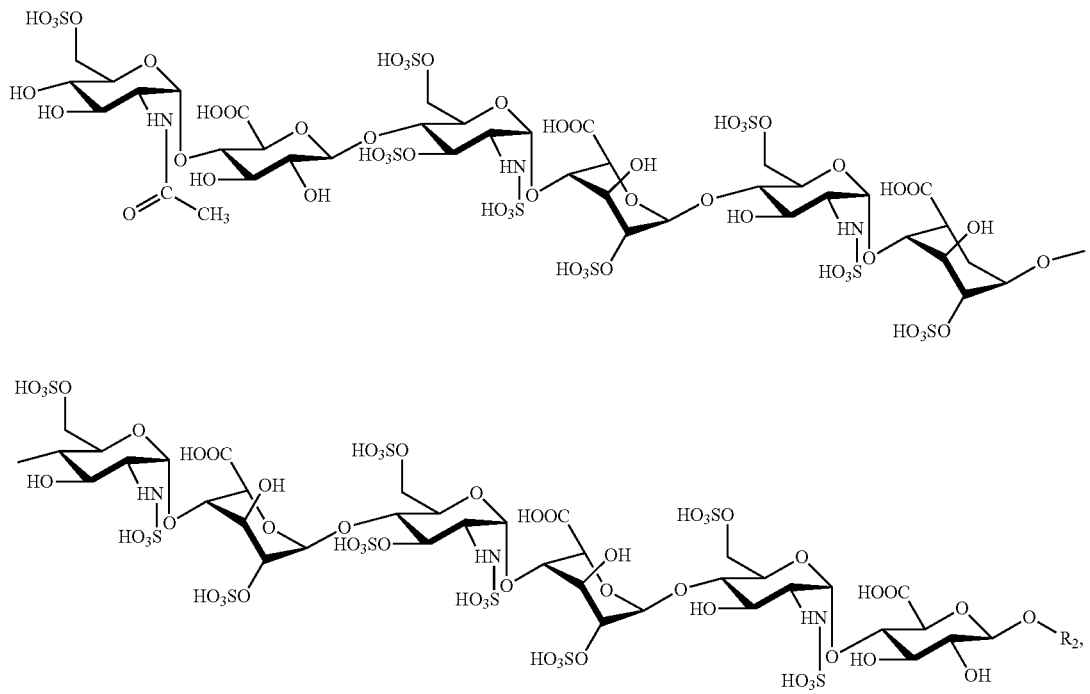

wherein $R_2$ is H or a detectable tag.

7. The method of claim 6, wherein the synthesized heparin compound is a synthetic, low-molecular weight heparin compound with reversible anticoagulant activity, wherein the anticoagulant activity of the heparin compound is reversible by protamine.

8. The method of claim 6, wherein the base is lithium hydroxide.

9. The method of claim 6, wherein the glycosyl transferase is selected from the group consisting of N-acetyl glucosaminyl transferase of *E. coli* K5 (KfiA) and/or heparosan synthase-2 (pmHS2) from *Pasteurella multocida*.

10. The method of claim 6, wherein the detectable tag is para-nitrophenyl.

11. A low-molecular weight heparin compound, which is a synthesized material, with reversible anticoagulant activity, represented by the following formula:

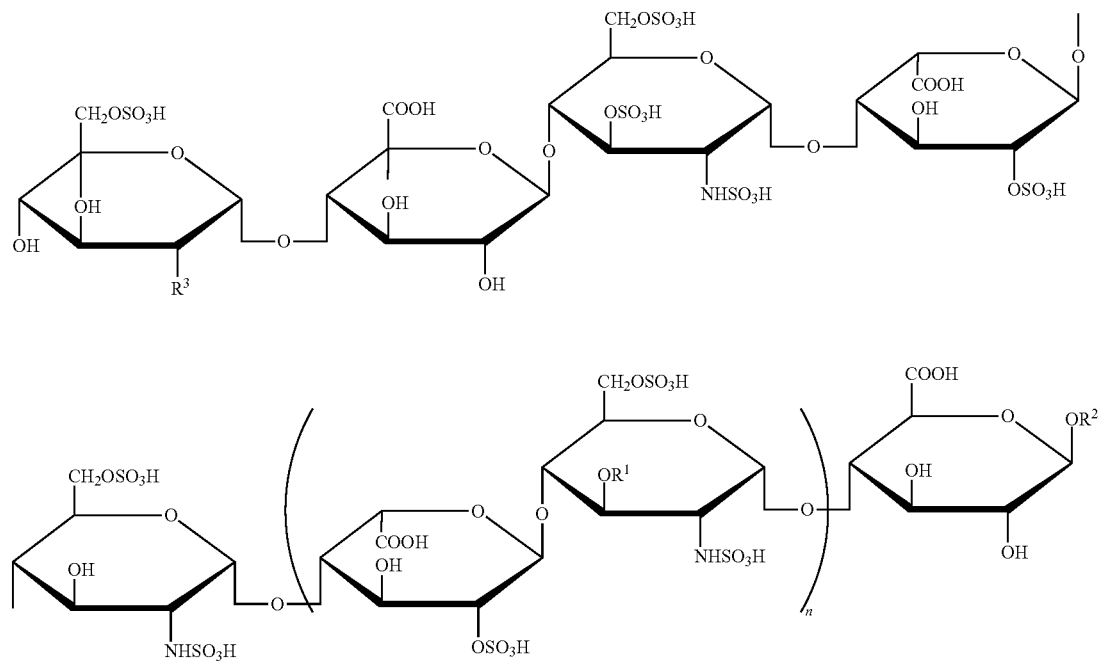

wherein $R^1$ is independently H or —SO$_3$H, $R^2$ is H or a detectable tag, $R^3$ is —NHSO$_3$H or —NHCOCH$_3$, and n is an integer of 0-3.

12. The heparin compound of claim 11, wherein the heparin compound is represented by the following structure:

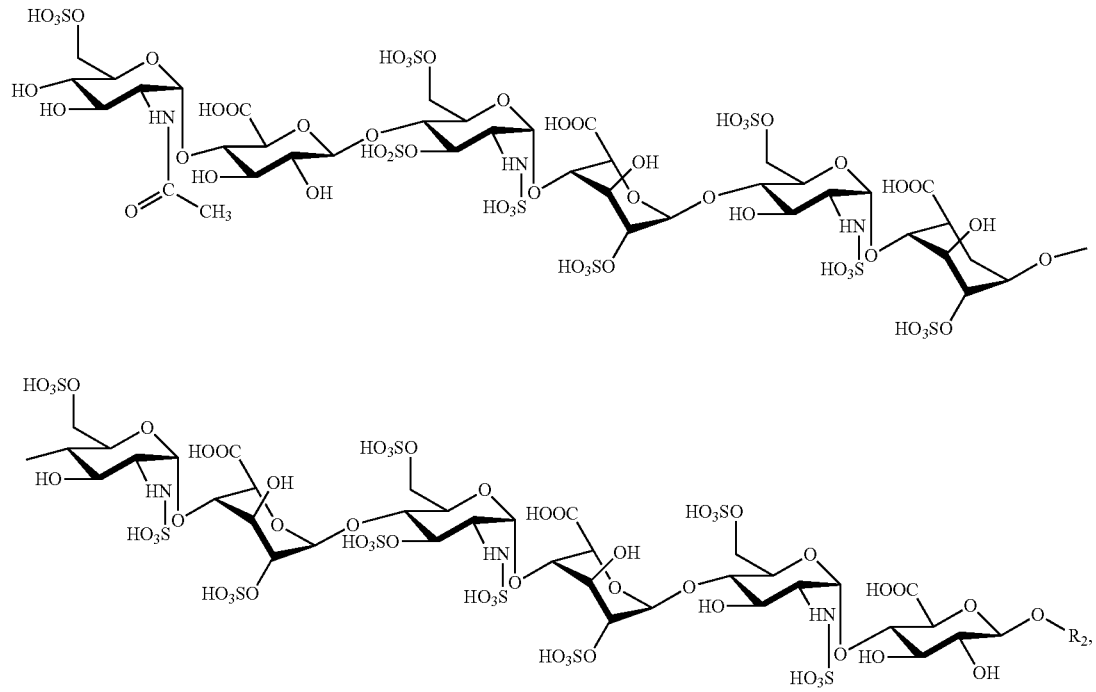

wherein $R_2$ is H or a detectable tag.

13. The heparin compound of claim 11, wherein the heparin compound is represented by the following structure:

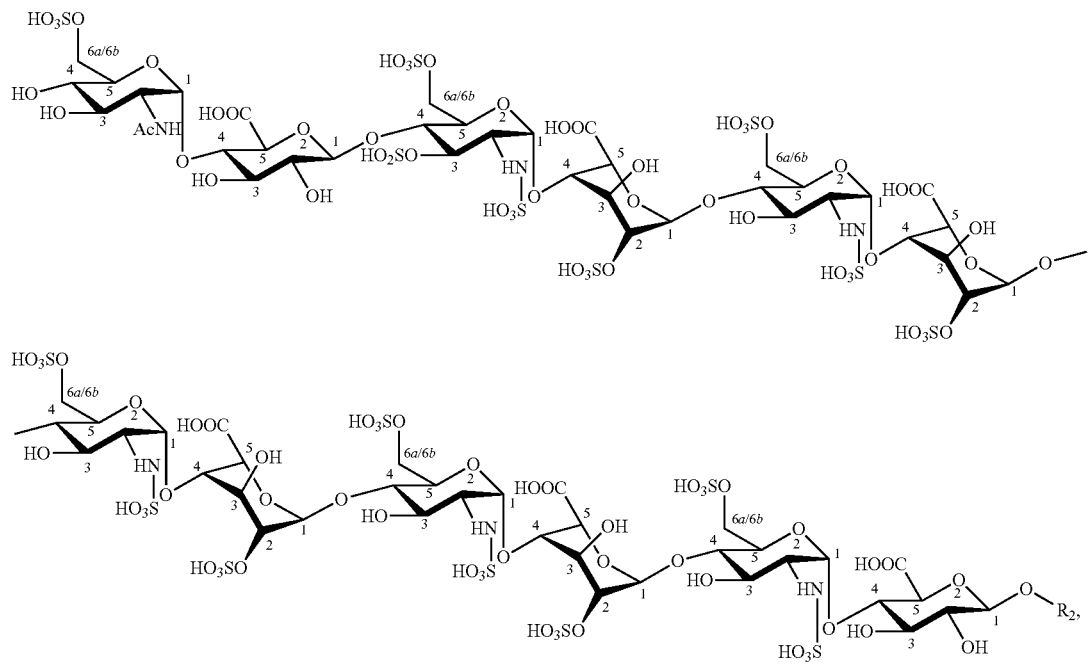

wherein $R_2$ is H or a detectable tag.

14. The heparin compound of claim 11, wherein the heparin compound comprises at least one 3-O sulfate.

15. The heparin compound of claim 11, wherein the heparin compound is a dodecamer.

16. The heparin compound of claim 11, wherein the detectable tag is paranitrophenyl.

17. A method of treating a subject, the method comprising:
providing a subject to be treated;
administering to the subject a heparin compound having anticoagulant activity, wherein the heparin compound is selected from:

18. The method of claim 17, wherein the subject suffers from venous thromboembolism.

19. The method of claim 17, wherein the subject is renal-impaired.

20. A method of treating a subject in need of anticoagulant therapy, the method comprising:
providing a subject in need of anticoagulant therapy;
administering to the subject a heparin compound having anticoagulant activity; monitoring the subject for heparin-induced thrombocytopenia; and administering to the subject an antidote to reverse the anticoagulant

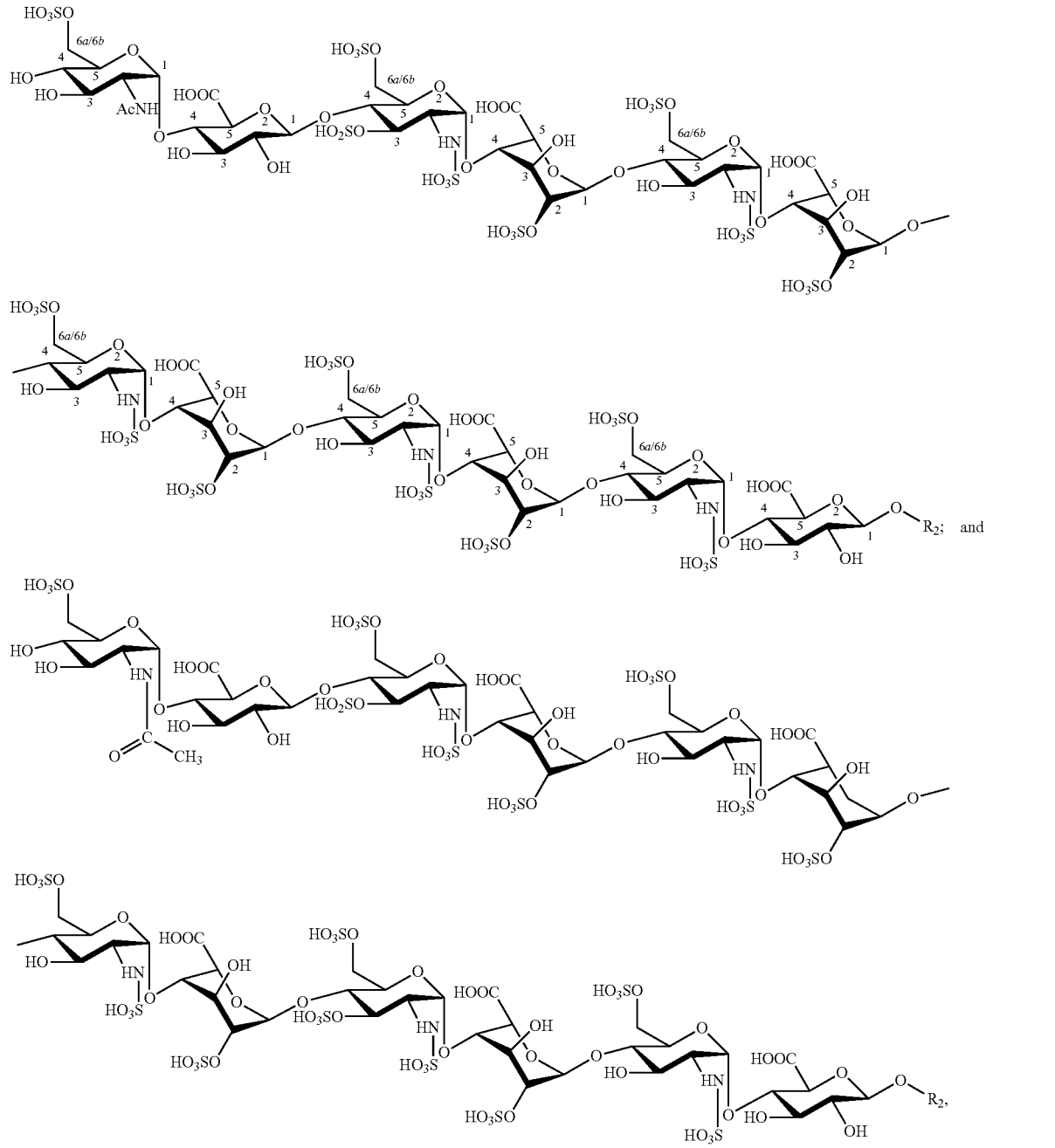

wherein $R_2$ is H or a detectable tag, and wherein the anticoagulant activity of the heparin compound is reversible by protamine.

activity of the heparin compound if the subject suffers from heparin-induced thrombocytopenia, wherein the heparin compound is selected from:

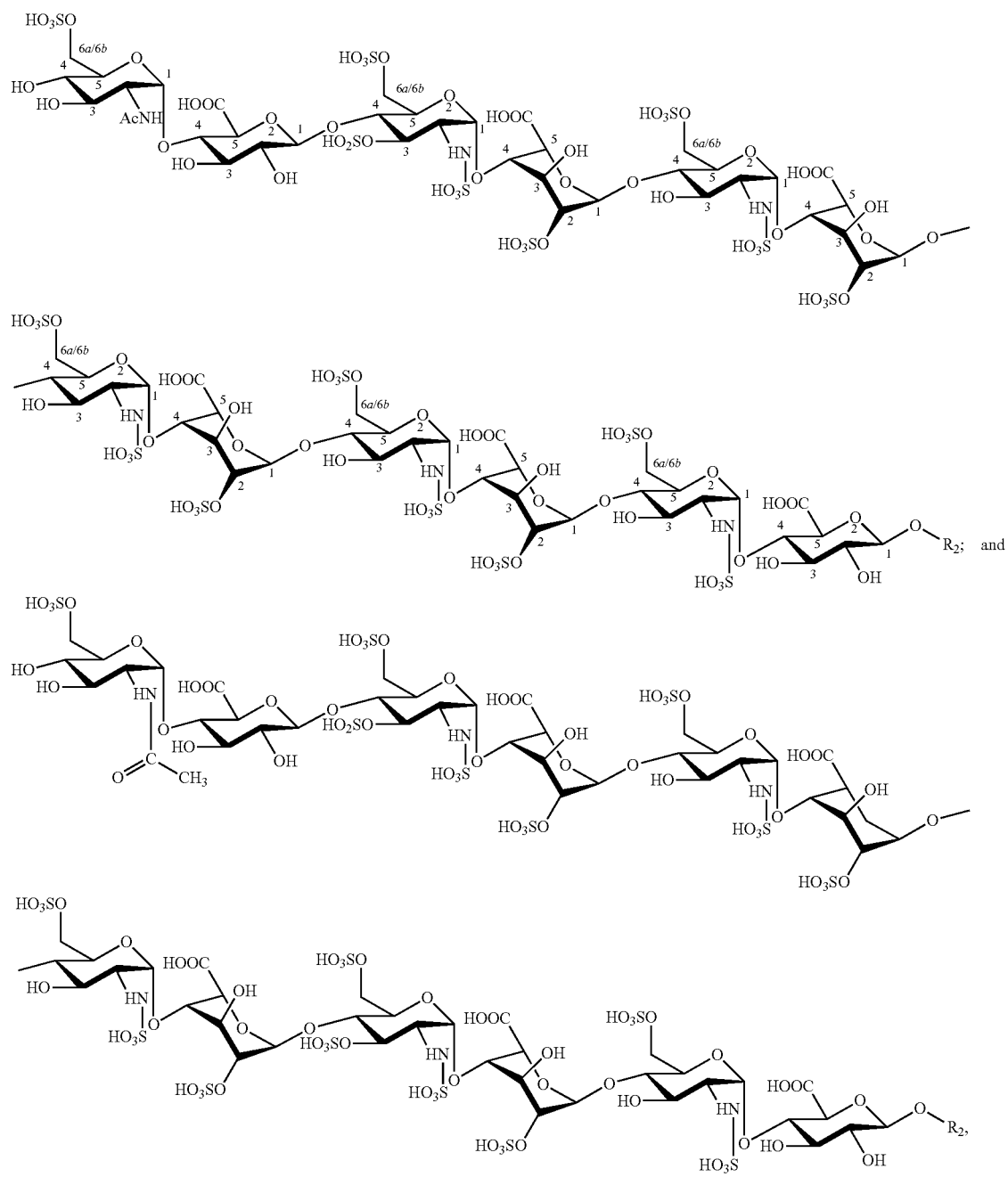
wherein $R_2$ is H or a detectable tag.
21. The method of claim 20, wherein the antidote to reverse the anticoagulant activity of the heparin compound is protamine.
* * * * *